United States Patent
Robb et al.

(10) Patent No.: US 12,398,173 B2
(45) Date of Patent: Aug. 26, 2025

(54) ENZYMATIC RNA CAPPING METHOD

(71) Applicant: New England Biolabs, Inc., Ipswich, MA (US)

(72) Inventors: G. Brett Robb, Somerville, MA (US); Siu-Hong Chan, Georgetown, MA (US); Bijoyita Roy, Medford, MA (US)

(73) Assignee: New England Biolabs, Inc., Ipswich, MA (US)

( * ) Notice: Subject to any disclaimer, the term of this patent is extended or adjusted under 35 U.S.C. 154(b) by 1053 days.

(21) Appl. No.: 17/001,236

(22) Filed: Aug. 24, 2020

(65) Prior Publication Data

US 2021/0054016 A1 Feb. 25, 2021

Related U.S. Application Data

(63) Continuation of application No. PCT/US2020/047521, filed on Aug. 21, 2020, and a continuation of application No. PCT/US2020/047533, filed on Aug. 21, 2020.

(60) Provisional application No. 62/890,821, filed on Aug. 23, 2019.

(51) Int. Cl.
| | |
|---|---|
| *C07H 19/20* | (2006.01) |
| *C07H 21/04* | (2006.01) |
| *C12P 19/34* | (2006.01) |
| *C12Q 1/6816* | (2018.01) |

(52) U.S. Cl.
CPC ............ *C07H 19/20* (2013.01); *C07H 21/04* (2013.01); *C12P 19/34* (2013.01); *C12Q 1/6816* (2013.01)

(58) Field of Classification Search
CPC ......... C07H 21/02; C07H 21/04; C12P 19/34; C12Y 201/01056
See application file for complete search history.

(56) References Cited

U.S. PATENT DOCUMENTS

| | | |
|---|---|---|
| 8,846,348 B2 † | 9/2014 | Jendrisak |
| 8,962,292 B2 | 2/2015 | Jais |
| 9,005,930 B2 | 4/2015 | Jendrisak et al. |
| 9,115,380 B2 | 8/2015 | Jendrisak et al. |
| 9,512,456 B2 | 12/2016 | Wang et al. |
| 9,540,671 B2 | 1/2017 | Jais |
| 9,629,804 B2 | 4/2017 | Heartlein et al. |

(Continued)

FOREIGN PATENT DOCUMENTS

| | | |
|---|---|---|
| AU | 2007238624 B2 | 5/2012 |
| EP | 2010659 B1 | 1/2009 |

(Continued)

OTHER PUBLICATIONS

Uniprot A01142BZT8 UniProtKB/TrEMBL information.*

(Continued)

*Primary Examiner* — Terra C Gibbs
(74) *Attorney, Agent, or Firm* — New England Biolabs, Inc

(57) ABSTRACT

Provided herein is a method for efficiently capping RNA in vitro. In some embodiments the capping reaction may be done at high temperature using Vaccinia capping enzyme or a variant thereof. In other embodiments, the capping reactions may comprise a capping enzyme from a large virus of amoeba, e.g., Faustovirus, mimivirus or moumouvirus, or a variant thereof. Compositions and kits for practicing the method are also provided.

18 Claims, 22 Drawing Sheets

Specification includes a Sequence Listing.

| substrate | RNA1 | RNA2 | RNA3 | RNA4 |
|---|---|---|---|---|
| number of nucleotide | 25 | 23 | 24 | 25 |
| MFE (kcal/mol) at 37°C | -1.5 | -7.2 | -7.2 | -7.2 |
| MFE (kcal/mol) at 45°C | -0.73 | -5.4 | -5.4 | -5.4 |

(56) References Cited

U.S. PATENT DOCUMENTS

| | | |
|---|---|---|
| 9,790,531 B2 | 10/2017 | Wang et al. |
| 10,428,368 B2 | 10/2019 | Schildkraut et al. |
| 10,519,431 B2 | 12/2019 | Ong et al. |
| 11,788,074 B2 | 10/2023 | Vainauskas et al. |
| 2012/0251618 A1 | 10/2012 | Schrum et al. |
| 2013/0042334 A1 | 2/2013 | Eukarys |
| 2014/0152211 A1 | 6/2014 | Ko |
| 2016/0038432 A1 | 2/2016 | DeRosa et al. |
| 2017/0253911 A1 | 9/2017 | Schildkraut et al. |
| 2018/0195061 A1 | 7/2018 | Schildkraut et al. |
| 2018/0237817 A1 | 8/2018 | Roos et al. |

FOREIGN PATENT DOCUMENTS

| | | |
|---|---|---|
| EP | 2558579 B1 | 8/2013 |
| EP | 3077406 B1 | 7/2019 |
| WO | 2017123748 A1 | 7/2017 |
| WO | 2018236617 A1 | 12/2018 |
| WO | 2019020811 A1 | 1/2019 |

OTHER PUBLICATIONS

Warren et al. (2010) Cell Stem Cell, vol. 7:618-630.*
Sutton et al. (Nature Structural & Molecular Biology vol. 14, pp. 449-451 (2007)).*
Ramadevi et al. (PNAS, 1998 vol. 95:13537-13542).*
UniProt A0A0H3TMA9 (entry version 10, dated Dec. 5, 2018).*
UniProt A0A1X7C035 (entry version 8, dated Jul. 31, 2019).*
UniProt A0A1X7QHRO (entry version 8, dated Dec. 5, 2018).*
Pichlmair, et al., Science 2006 314: 997-1001.
Diamond, et al., Cytokine & Growth Factor Reviews, 2014 25: 543-550.
Fuchs, RNA, 2016 22: 1454-66.
Li, et al J. Org. Chem. 2012 77: 9889-9892.
Cong, et al, Molecular and Cellular Biology, 6222-6231, 15, 11, 1995.
New England Biolabs, M2080 Capping System product information Feb. 26, 2020.
Cong, et al (1993). "Covalent catalysis in nucleotidyl transfer. A KTDG motif essential for enzyme-GMP complex formation by mRNA capping enzyme is conserved at the active sites of RNA and DNA ligases." J Biol Chem 268(10): 7256-60.
Niles, et al (1993). "Identification of the vaccinia virus mRNA guanyltransferase active site lysine." J Biol Chem 268 (33): 24986-9.
Higman, et al (1994). "Location of the S-adenosyl-L-methionine binding region of the vaccinia virus mRNA (guanine-7-)methyltransferase." J Biol Chem 269(21): 14982-7.
Mao, et al (1994). "Intrinsic RNA (guanine-7) methyltransferase activity of the vaccinia virus capping enzyme D1 subunit is stimulated by the D12 subunit. Identification of amino acid residues in the D1 protein required for subunit association and methyl group transfer." J Biol Chem 269(39): 24472-9.
Gong, et al (2003). "Mapping the active site of vaccinia virus RNA triphosphatase." Virology 309(1): 125-34.
Higman, et al (1992). "The vaccinia virus mRNA (guanine-N-7-)-methyltransferase requires both subunits of the mRNA capping enzyme for activity." J Biol Chem 267(23): 16430-7.
Higman, et al. (1994). "The mRNA (guanine-7) methyltransferase domain of the vaccinia virus mRNA capping enzyme. Expression in *Escherichia coli* and structural and kinetic comparison to the intact capping enzyme." J Biol Chem 269(21): 14974-81.
Osborn, et al., A picornaviral 2A-like sequence-based tricistronic vector allowing for high-level therapeutic gene expression coupled to a dual-reporter system. Mol Ther. 2005; 12:569-574.
Donnelly, et al Analysis of the aphthovirus 2A/2B polyprotein 'cleavage' mechanism indicates not a proteolytic reaction, but a novel translational effect: a putative ribosomal 'skip' J Gen Virol. 2001; 82:1013-1025.
Donnelly, et al., The 'cleavage' activities of foot-and-mouth disease virus 2A site-directed mutants and naturally occurring '2A-like' sequences. J Gen Virol. 2001; 82:1027-1041. doi: 10.1099/0022-1317-82-5-1027.
Lee, et al., Synergistic effects of 2A-mediated polyproteins on the production of lignocellulose degradation enzymes in tobacco plants. J Exp Bot. 2012; 63:4797-4810.
Rasala, et al. (2012). Robust expression and secretion of Xylanase1 in Chlamydomonas reinhardtii by fusion to a selection gene and processing with the FMDV 2A peptide. PLoS One. 7:e43349.
Chng, et al., (2015). Cleavage efficient 2A peptides for high level monoclonal antibody expression in CHO cells. MAbs. 7:403-412.
Sun, et al. (2012). Double Candida antarctica lipase B co-display on Pichia pastoris cell surface based on a self-processing foot-and-mouth disease virus 2A peptide. Appl Microbiol Biotechnol. 96:1539-1550.
De Amorim Araujo, et al., (2015). Coexpression of cellulases in Pichia pastoris as a self-processing protein fusion. AMB Express, 5(1), 84.
De Felipe, et al. (2003). Co-translational, intraribosomal cleavage of polypeptides by the foot-and-mouth disease virus 2A peptide. J Chem. 278:11441-11448.
Crasto, et al. (2000). LINKER: a program to generate linker sequences for fusion proteins. Protein engineering, 13 (5), 309-312.
Wu, et al. (2004). High efficiency transformation by electroporation of Pichia pastoris pretreated with lithium acetate and dithiothreitol. BioTechniques, 36(1), 152-154.
Looke, et al.,(2011). Extraction of genomic DNA from yeasts for PCR-based applications. BioTechniques, 50(5), 325-328.
Ryan, et. al., 1991, Cleavage of foot-and-mouth disease virus polyprotein is mediated by residues located within a 19 amino acid sequence. J Gen Virol. 72:2727-2732.
Beverly, et al., Analytical and Bioanalytical Chemistry, 408, 5021-2030, 2016.
Wulf, et al., Scientific Reports, 9, 8594, 2019.
Uniprot A0A142BZT8.A0 A142BZT8_9VIRU, Jun. 8, 2016.
Benarroch, et al., Structure, 16, 501-512, 2008.
Shuman, JBC, 265, 20, 11960-11966, 1990.
Guo, et al., Proc Natl Acad Sci USA. 87, 11:4023-7, 1990.
Paoletti, et al., Journal of Virology, 33, 1, 208-19, 1980.
Furuichi, et al., Nature, 266, 235-237, 1977.
Lewis, et al., Eur. J. Biochem. 247, 461-469, 1977.
Izuka, et al., Mol. Cell. Biol. 14, 7322-7330, 1994.
Rubenstein, et al., JCB, 96, 1464-1469, 1983.
Shuman, Methods in Enzymology, 181, 170-180, 1990.
Benamar, et al., Frontiers in Microbiology, 7, 3, 2016.
Du, et al., Journal of Virology, 95, 5, e02029-20, 2021.
Dunyak, et al., Eukaryotic Cell, 1, 6, 1010-1020, 2002.
Hausmann, et al., The Journal of Biological Chemistry, 277, 1, 96-103, 2022.
Jais, et al., Nucleic Acids Research, 47, 5, 2681-2698, 2019.
Pena, et al., Virology, 193, 319-328, 1993.
Reteno, et al., Journal of Virology, 89, 13, 6585-6594, 2015.
Schneider, et al., Molecular and Cellular Biology, 30, 2353-2364, 2010.
Takizawa, et al., PLoS ONE, 8, 10, e78000, 2013.
Johnson, et al., bioRxiv 2023.03.04.531015; doi: https://doi.org/10.1101/2023.03.04.531015.
Fisher, et al., ACS Cent. Sci. 2019, 5, 1844-1856.
Higman, et al., The Journal of Biological Checmistry, 267, 23, 16430-16437, 1992.
Mao, et al., The Journal of Biological Chemistry, 269, 39, 24472-24479, 1994.
Uniprot A01142BZT8 version 11 dated Jul. 31, 2019.
UniProt Accession No. A0A142BZT8 version 1, listing a release date of Jun. 8, 2016 (archived text file accessed at <https://www.uniprot.org> on Aug. 27, 2024).
UniProt Accession No. A0A142BZT8 version 2, listing a release date of Jul. 6, 2016 (archived text file accessed at <https://www.uniprot.org> on Aug. 27, 2024).
UniProt Accession No. A0A142BZT8 version 3, listing a release date of Sep. 7, 2016 (archived text file accessed at <https://www.uniprot.org> on Aug. 27, 2024).

(56) References Cited

OTHER PUBLICATIONS

UniProt Accession No. A0A142BZT8 version 4, listing a release date of May 10, 2017 (archived text file accessed at <https://www.uniprot.org> on Aug. 27, 2024).
UniProt Accession No. A0A142BZT8 version 5, listing a release date of Oct. 25, 2017 (archived text file accessed at <https://www.uniprot.org> on Aug. 27, 2024).
UniProt Accession No. A0A142BZT8 version 6, listing a release date of Feb. 28, 2018 (archived text file accessed at <https://www.uniprot.org> on Aug. 27, 2024).
UniProt Accession No. A0A142BZT8 version 7, listing a release date of Mar. 28, 2018 (archived text file accessed at <https://www.uniprot.org> on Aug. 27, 2024).
UniProt Accession No. A0A142BZT8 version 8, listing a release date of Jul. 18, 2018 (archived text file accessed at <https://www.uniprot.org> on Aug. 27, 2024).
UniProt Accession No. A0A142BZT8 version 9, listing a release date of Nov. 7, 2018 (archived text file accessed at <https://www.uniprot.org> on Aug. 27, 2024).
UniProt Accession No. A0A142BZT8 version 10, listing a release date of Dec. 5, 2018 (archived text file accessed at <https://www.uniprot.org> on Aug. 27, 2024).
UniProt Accession No. A0A142BZT8 version 11, listing a release date of Jul. 31, 2019 (archived text file accessed at <https://www.uniprot.org> on Aug. 27, 2024).
UniProt Accession No. A0A142BZT8 version 12, listing a release date of Dec. 11, 2019 (archived text file accessed at <https://www.uniprot.org> on Aug. 27, 2024).
UniProt Accession No. A0A142BZT8 version 13, listing a release date of Aug. 12, 2020 (archived text file accessed at <https://www.uniprot.org> on Aug. 27, 2024).
UniProt Accession No. A0A142BZT8 version 14, listing a release date of Oct. 7, 2020 (archived text file accessed at <https://www.uniprot.org> on Aug. 27, 2024).
UniProt Accession No. A0A142BZT8 version 15, listing a release date of Dec. 2, 2020 (archived text file accessed at <https://www.uniprot.org> on Aug. 27, 2024).
UniProt Accession No. A0A142BZT8 version 16, listing a release date of Feb. 10, 2021 (archived text file accessed at <https://www.uniprot.org> on Aug. 27, 2024).
UniProt Accession No. A0A142BZT8 version 17, listing a release date of Jun. 2, 2021 (archived text file accessed at <https://www.uniprot.org> on Aug. 27, 2024).
UniProt Accession No. A0A142BZT8 version 18, listing a release date of Sep. 29, 2021 (archived text file accessed at <https://www.uniprot.org> on Aug. 27, 2024).
UniProt Accession No. A0A142BZT8 version 19, listing a release date of Feb. 23, 2022 (archived text file accessed at <https://www.uniprot.org> on Aug. 27, 2024).
UniProt Accession No. A0A142BZT8 version 20, listing a release date of May 25, 2022 (archived text file accessed at <https://www.uniprot.org> on Aug. 27, 2024).
UniProt Accession No. A0A142BZT8 version 21, listing a release date of Aug. 3, 2022 (archived text file accessed at <https://www.uniprot.org> on Aug. 27, 2024).
UniProt Accession No. A0A142BZT8 version 22, listing a release date of Dec. 14, 2022 (archived text file accessed at <https://www.uniprot.org> on Aug. 27, 2024).
UniProt Accession No. A0A142BZT8 version 23, listing a release date of Feb. 22, 2023 (archived text file accessed at <https://www.uniprot.org> on Aug. 27, 2024).
UniProt Accession No. A0A142BZT8 version 24, listing a release date of Jun. 28, 2023 (html accessed at <https://www.uniprot.org> on or around Sep. 15, 2023).
UniProt Accession No. A0A142BZT8 version 25, listing a release date of Jan. 24, 2024 (archived text file accessed at <https://www.uniprot.org> on Aug. 27, 2024).
UniProt Accession No. A0A142BZT8 version 26, listing a release date of May 29, 2024 (archived text file accessed at <https://www.uniprot.org> on Aug. 27, 2024).
UniProt Accession No. A0A142BZT8 version 26, listing a release date of May 29, 2024 (html accessed at <https://www.uniprot.org> on Aug. 27, 2024).
UniProt Accession No. A0A142BZT8, Compare version 1 vs version 11 (accessed at <https://www.uniprot.org> on Aug. 27, 2024).
UniProt Accession No. A0A142BZT8, Compare version 1 vs version 24 (accessed at <https://www.uniprot.org> on Aug. 27, 2024).
UniProt Accession No. A0A142BZT8, Compare version 11 vs version 24 (accessed at <https://www.uniprot.org> on Aug. 27, 2024).
UniProt Accession No. A0A142BZT8, History tab (accessed at <https://www.uniprot.org> on Aug. 27, 2024).
European Nucleotide Archive Accession No. AMN83561 version1, listing a creation date of Mar. 18, 2016 (archived EMBL text file accessed at https://www.ebi.ac.uk/ena/browser/home on Aug. 27, 2024).
UniProt Online Training Materials, Sections 1, 1.1, 2, 2.1, 2.2, 2.3, 2.3.1, 10.1, 10.1.1, 10.1.9, and 10.5 (Accessed at https://www.ebi.ac.uk/training/online/courses/uniprot-exploring-protein-sequence-and-functional-info/ on Jun. 26, 2024).
Sutton et al. ("Sutton"), "Bluetongue virus VP4 is an RNA-capping assembly line", p. 449-451, Apr. 8, 2007, Nature Structural.†
Ramavadi et al. ("Ramavadi"), "Capping and methylation of mRNA by purified recombinant VP4 protein of bluetongue virus", p. 13537- 13542, Nov. 10, 1998, Proc. Natl. Acad. Sci. USA.†

\* cited by examiner
† cited by third party

- substrate RNA

- substrate RNA

- substrate RNA

- substrate RNA

- substrate RNA

```
                     10        20        30        40        50        60        70
                     ....|....|....|....|....|....|....|....|....|....|....|....|....|....|
AMN83561       1     --------------MAKRLQRCQDVNQVCEIYNSKGGIGELELRFDKLPQNLFAGV FDKLKPDGEI QTTMR
AIB52055       1     --------MRRVFNSAKKQQRCDSVEQVCEFYNADNKTNELELRFDKLNRELFVVL FDKLKPDGEI TTTMR
SME65026       1     --------MRRVSNSAKKQQRCDSVEQVCEFYNADNKTNELELRFDKLNRELFVAL FDKLKPDGEI TTTMR
SMH63629       1     LEYQYYKYILVNIMSRRLQRCRDVDQVCEYYNAKGAIGELELRFDKLTPDLFAHV  FDKLKPDGEI STTMR
Fausto_CR_01   1     -------------------------------------------------------- FDKLKPDGEI TTTMR

|---------------- TPase ----------------
                        80        90       100       110       120       130       140
                     ....|....|....|....|....|....|....|....|....|....|....|....|....|....|
AMN83561       58    VSNRDGV AREITFGGGVKT NELF VK QNICVFDVVL FSYKVAVS TEETVVEKPTMETTAGVRFKIRLSV
AIB52055       64    VSNADGV AREITFGGGVKT GEMF VK QNICVFDVVL FSYKVAVS SEDEIKDKPKMDTNASVRFKIRLSC
SME65026       64    VSNADGV AREITFGGGVKT GEMF VK QNICVFDVVL FSYKVAVS SEDEVKDKPKMDTNASVRFKIRLSC
SMH63629       71    VSNSDGT AREITFGGGVKT GETF VK QNICVFDVVD FSYKVAVS TEETLVDKPAMEKDASVRFKIRMSV
Fausto_CR_01   16    VSNADGV AREITFGGGVKT GEMF VK QNICVFDVVL FSYKVAVS --------------------------

--- TPase -----|
                       150       160       170       180       190       200       210
                     ....|....|....|....|....|....|....|....|....|....|....|....|....|....|
AMN83561       128   EDVVKDWRIDLTAVKTAELGKIAQHTASIVQRTFPDNLLKLTGAEVAKLAADSYELELEYTGKSPATNEK
AIB52055       134   DTLIPDWRIDLTAVKVADLGKIAQHTSTVVLQTFPENLLRMKGAEVAALATNSYELELEYIGKSAASKEK
SME65026       134   DTLIPDWRIDLTAVKVADLGKIAQHTSTVVLQTFPENLLRMKGAEVAALATNSYELELEYIGKSTAGKEK
SMH63629       141   EGAVPNWRIDLTAVKTAELGKIAQHTASLVLQTFPPNLLKMSGAEVAKLANNSYELELEYIGKTPATKER 220       230       240       250       260       270       280
                     ....|....|....|....|....|....|....|....|....|....|....|....|....|....|
AMN83561       198   VNVAAKYAVELLSSVRNANSTAAASFGESVSDLCRVAKIIHTHEYANVVCRTPSFKMLLPQVVSLTKSSY
AIB52055       204   VLAAAEYAMELLTNSRNAISPAAATLGESVSDICRIAKLIHPAEYANVICRTPSFKNLPQVISLTKSSY
SME65026       204   VLKAAEYAIELLTNLRNAVSPVAATLGESVSDICRIAKLIHPAEYANVICRTPSFKNLLPQVISLTKSSY
SMH63629       211   VDAAAKYAVDLLAGIKNANSAVGAVLGESISDICRVAKVIHTPDYATVVCRNPSFKMLLPQVISLTKSSY

|---------------- GTase ----------------
                       290       300       310       320       330       340       350
                     ....|....|....|....|....|....|....|....|....|....|....|....|....|....|
AMN83561       268   YGGLYPPENLWLAGKTDGVRALVVCEDGVAKVITAESVDITHGVCSATTILDCELNVD-------AKILY
AIB52055       274   YGGIYPPVDMYIAGKTDGVRALVLCENGVAKIITATTVDTTTVGNTPITILDCELSTSGHNGATDNKHLY
SME65026       274   YGGIYPPVDMYITGKTDGVRALVLCENGVAKIITATTVDTTTVGDTPITILDCELSTSGHNGATDNKHLY
SMH63629       281   YGGIYPPEGMYVAGKTDGVRALVLCEDGVAKVITAESVDITTGTCTGTTILDCELSTGKS----GATLH
```

FIG. 5

```
                   |------------------------------ GTase ----------------------------------|
                           360        370        380        390        400        410        420
                     ....|....|....|....|....|....|....|....|....|....|....|....|....|....|
AMN83561       331   VFDVIISNNTQVYTQPFSTRITTDISDIKIDGYKIEMKPFVKVVK---ADEATFKSAYKAPHNEGLIMIE
AIB52055       344   IFDVIMNRGVHSHREGFNKRIDIDLSDLTPAGYTLELKPFTKLVDAASVNETTFKSVKPPHNEGLVLVE
SME65026       344   VFDVIMNRGAHSHRDGFNKRIDIDLSDLTPAGYTLELKPFTKVADAASVNETTFKSVFKPPHNEGLVLVE
SMH63629       346   VFDIIMHNSKPIHSQPFSTRIATDISDVKIPEYKIAIKPFVKIQAT--ALEAAFKEVYKAPHNEGLILIM 430        440        450        460        470        480        490
                     ....|....|....|....|....|....|....|....|....|....|....|....|....|....|
AMN83561       398   DGAAYAATKTYKWKPLSHNTIDFLIKACPKQLINVDPYKPRAGYKLWLLFTTISLDQQRELGIEFIPAWK
AIB52055       414   SGPPYALTKTYKWKPITHNTIDFLIKACPKQLINVDPFKPRNGHDLWLLFTTISLDQQRELGIDLIPAWK
SME65026       414   SGPPYALTKTYKWKPITHNTIDFLIKACPKQLINVDPFKPRNGHDLWLLFTTISLDQQRELGIDLIPAWK
SMH63629       414   DGNDYAMTKTYKWKPLSHNTIDFLIKACPKQLLNIDPYKPRPGHKLWLLFTTISLDQQRELGIEFIPAWK 500        510        520        530        540        550        560
                     ....|....|....|....|....|....|....|....|....|....|....|....|....|....|
AMN83561       468   ILFTDINMFGSRVPIQFQPAINPLAYVCYLPEDVN------VNDGDIVEMRAVDGYDTIPKWELVRSRND
AIB52055       484   LLFTDVNLFGNKIPIQFMPAINPLAYICYLPSSTG------VNDGDIVEMRAVDGFDGIPTWELVRTRPD
SME65026       484   LLFTDVNLFGNKIPIQFMPAINPLAYICYLPSSTG------VNDGDIVEMRAVDGFDGIPTWELVRTRPD
SMH63629       484   MLFTDINLFGSRVPIQFMPAINPLAYICYLPEAATCANGDAINDGDIVEMRAVDGFDTVPKWEPIRVRSD

|---------- MTase -
                          570        580        590        600        610        620        630
                     ....|....|....|....|....|....|....|....|....|....|....|....|....|....|
AMN83561       532   RKNEPGFYGNNYKIASDIYLNYIDMFHFEDLYKYNPGYFEKNKSDIYVAPNKYRRMLIKSLFCGYLRDAK
AIB52055       548   RKDERGFYGNNYKIASDIYLNYIDMFNFDDLWKYNPGYFEKNKSDIYIAPNKYRRMLIKSLFNYEKNAK
SME65026       548   RKDERGFYGNNYKIASDIYLNYIDMFNFDDLWKYNPGYFEKNKSDIYIAPNKYRRMLIKSLFNYEKNAK
SMH63629       554   RKDEPGFYGNNYKIASDIYLNYIDIFQFEDLWKYNPGYFEKNKSDIYVAPNKYRRELIKNIFSKYLKNAK
Fausto_CR_03     1   -----GFYGNNYKIASDIYLNYIDMFNFEDLWKYNPGYFEKNKSDIYIAPNKYRRMLIKSLFNYEKNAK
```

FIG. 5 (Cont. 1)

```
                     ---------------------------------- MTase ----------------------------------
                            640        650        660        670        680        690        700
                       ....|....|....|....|....|....|....|....|....|....|....|....|....|....|
AMN83561      602  WVIDAAAGRGADLHLYKAECVERLLAIDIDPTAISELVRRRNEITGYNKSHRGGR---NMHSHRGQSH----
AIB52055      618  WVIDAAAGRGADLHLYKQECVERLLAIDIDPTAISELIRRRNEITGWQQRGRGG----NTRHNARHN----
SME65026      618  WVIDAAAGRGADLHLYKQECVERLLAIDIDPTAISELIRRRNEITGWQQRGRGGNMHHNSRHNTRHN---
SMH63629      624  WVIDAAAGRGADLHLYKAECVERLLAIDIDPTAISELVRRRNEITGYNRGHRGHRGGSMRAHMGASHHGA
Fausto_CR_03   66  WVIDAAAGRGADLHLYKAECVERLLAIDIDPTAISELIRRRNEITG------------------------

---------------------------------- MTase ----------------------------------
                            710        720        730        740        750        760        770
                       ....|....|....|....|....|....|....|....|....|....|....|....|....|....|
AMN83561      666  --CAKSTSLHALVADLRENPDVLIPKIIQSRPHERCYDAIVINFAIHYLCDTDEHIRDFLITVSRLLAPN
AIB52055      681  THCASSTSLHALVADLRTEPNMLIPKIIQSRPPERGYDAIVINFAIHYLCETDDYIRNFLITVSRLLAPD
SME65026      685  THCASSTSLHALVADLRTEPNMLIPKIIQSRPPERGYDALVINFAIHYLCETDDYIRNFLITVSRLLAHD
SMH63629      694  QNCAKSTTLHALVADLRTDPDVLIPKIIQSRPPERGYDAIVINFAIHYLCDTDEHIRDFLITVSRLLAPN ---------------------------------- MTase ----------------------------------
                            780        790        800        810        820        830        840
                       ....|....|....|....|....|....|....|....|....|....|....|....|....|....|
AMN83561      735  GVFIFTTMDGESIVKLLADHKVRPGEAWTIHTGD-VNSPDSTVPKYSIRRLYDSDKLTKTGQILVLLPM
AIB52055      751  GVFIFTTMDGEAIVNLLAEHKVAPGASWVVHTDGNANATDANVVKYSIRRLYDSDKLTKTGQKIAVLLPM
SME65026      755  GVFIFTTMDGEAIVNLLTEHKVAPGASWVVHTDGNTNATDANVVKYSIKRLYDSDKLTKTGQKIAVLLPM
SMH63629      764  GIFMFTTMDGESIVKLLETHKVKSGESWTVHTG--ADDPEAGVIKYSIRRLYDSDKLTKTGQIAVLLPM
Fausto_CR_05    1  ----------------------------------------------KYSIKRLYDSDKLTKTGQKIAVLLPM ---------------------------- MTase -----|
                            850        860        870        880        890        900        910
                       ....|....|....|....|....|....|....|....|....|....|....|....|....|....|
AMN83561      804  SGEMAEPLCNIKNISMARKMGLDLVESANFSVLYEAYARDYPDIYARMTPDDKLYNDLHTYAVFKRKK
AIB52055      821  SGEMEEPLCNIKNIVSMARKMGLDLVESANFSVLYGAYAKDYPEIYAKLTPDDKLYND LHAFAVFKRKK
SME65026      825  SGEMEEPLCNIKNIVSMARKMGLDLVESANFSVLYGAYAKDYPEIYAKLTPDDKLYNDLHAFAVFKRKK
SMH63629      832  SGEMKTEPLCNIKNISTARKMGLDLVESADFSVMYDAFARAYPEISARLTPDDKLYNDLHSYAVFKRKK
Fausto_CR_05   27  SGEMEEPLCNIKNISMARKMGLDLVESANFSV-----------------------------------
```

FIG. 5 (Cont. 2)

```
                              |---------- TPase ----------
             10        20        30        40        50        60        70
             ....|....|....|....|....|....|....|....|....|....|....|....|....|....|
AAV50651   1 MGTKLKKSNNDITIFSENEYNEIVEMLRDYSNGDNLEFEVSFKNINYPNFMRITEHYINITPENKIESNN
YP_007354410 1 MVTKNK-SENIRDILGSDNVSRVEEMINNFRKNRNTEFEISVRKINYSNYIRISEYYVNTS--SDIQQVT -------- TPase --------
             80        90       100       110       120       130       140
             ....|....|....|....|....|....|....|....|....|....|....|....|....|....|
AAV50651    71 YLDISLIFPDKNVYRVSLFNQEQIGEFITKFSKASSNDISRYIVSLDPSDDIEIVYKNRGSGKLIGIDNW
YP_007354410 68 SLDISIILEDGNTYRVSFLNENLINDFLSKYSNMKYGDIVKYILALNPNDDIEIIYKNRGSADRLSIEDL -------- TPase --------
             150       160       170       180       190       200       210
             ....|....|....|....|....|....|....|....|....|....|....|....|....|....|
AAV50651   141 AITIKSTEEIPLVAGKSKISKPKITGSERIMYRYKTRYSFTINKNSRIDITDVKSSPIIWKLMTVPSNYE
YP_007354410 138 NLVVKLTEEVPVLN---NTTKPKLSGREKILYRYKNRYSFIIDDITRIDITDVKETPNIWELSRKISNYE --- TPase ---|
             220       230       240       250       260       270       280
             ....|....|....|....|....|....|....|....|....|....|....|....|....|....|
AAV50651   211 LELELIN-KIDINTLESELLNVFMIIQDTKIPISKAESDTVVEEYRNLLNVRQTNNLDSRNVISVNSNHI
YP_007354410 205 IELEFTNNKIKSNQVFEKIFDLLRIVQNTEIPIGIRESKQVITDYQNLLNLRSSNHLDSRNVVSIETQHI --------------------- GTase ---------------------
             290       300       310       320       330       340       350
             ....|....|....|....|....|....|....|....|....|....|....|....|....|....|
AAV50651   280 INFIPNRYAVTDKADGERYFLFSLNSGIYLLSINLTVKKLNIPVLEKRYQNMLIDGEYIKTTGHDLFMVF
YP_007354410 275 VKFVPNRYAITDKADGERYFLFSTPNGVYLLSTNLTVKKVNIPVLQKDFQNMLLDGELIDIDGKELFMVF --------------------- GTase ---------------------
             360       370       380       390       400       410       420
             ....|....|....|....|....|....|....|....|....|....|....|....|....|....|
AAV50651   350 DVIFAEGTDYRYDNTYSLPKRIIINNIIDKCFGNLIPFNDYTDKHNNLELDSIKTYYKSELSNYWKNFK
YP_007354410 345 DVVYHNGIDYRYDTNYTLTHRIIIINDIIDKAFNNLIPFTDYTDKYNNLELDKIKEFYSNEIKTYWKNFS --------------------- GTase ---------------------
             430       440       450       460       470       480       490
             ....|....|....|....|....|....|....|....|....|....|....|....|....|....|
AAV50651   420 NRLNKSTDLFITRKLYLVPYGIDSSEIFMYADMIWKLYVYNELTPYQLDGIIYTPINSPYLIRGGIDAYD
YP_007354410 415 KKLKNYSGLFISRKLYFVPYGIDSSEVFMYADLVWKLCVYDQLTPYKLDGIIYTPIASPYMIKTSANELD

|
             500       510       520       530       540       550       560
             ....|....|....|....|....|....|....|....|....|....|....|....|....|....|
AAV50651   490 TIPMEYKWKPPSQNSIDFYIRFKKDVSGADAVYYDNSVERAEGKPYKICLLYVGLNKQGQEIPIQFKVNG
YP_007354410 485 SVPMEYKWKPPSQNSIDFYVKFDKDARGNEAIYYDNAVVRGEGRPYKVCGLFVGLNKGGEEKPIAFKVAG 570       580       590       600       610       620       630
             ....|....|....|....|....|....|....|....|....|....|....|....|....|....|
AAV50651   560 VEQTANIYTKDGEATDINGNAINDNTVVEEVFDTLKHDMDDSYKWIPLRTRYDKTESVQKYHKIYGNNLQ
YP_007354410 555 VEQKAFIYLTNDEALDLSGNVINDNTVVEEIFDNFKIDMDDEYKWIPMRTRYDKTESVQKYPKKYGNNLH
moumou_CR_03   1 --------------------INDNTVVEEIFDNFKIDMDDEYKWIPMRTRYDKTESVQKYHKKYGNNLH
```

FIG. 6

```
                                                        |-------------- MTase -----------
                           640        650        660        670        680        690        700
                           ....|....|....|....|....|....|....|....|....|....|....|....|....|....|
AAV50651       630         IANRIMKTITNPIIEDIISSLGDPTTFNKEITLLSDFRDTKYNKQALTYYQKNTSNAAGMRAFNNELKSN
YP_007354410   625         IAIRIWRTITNPVEEIIAALGNASTFEKEMSKLVKMNES-YNKQSFSYYQKNTSNAIGMRAFNNELKSN
moumou_CR_03    50         IANRIMKTITNPIIEDII---------------------------------------------------
moumou_CR_04     1         ------------------------------------------------YYQKNTSNAAGMRAFNNELKSN --------------------------- MTase ----------------------------------
                           710        720        730        740        750        760        770
                           ....|....|....|....|....|....|....|....|....|....|....|....|....|....|
AAV50651       700         MITTYQRDGSKVLDIGCGRGGDLIKFINAQMEIYVQIDIDNNGLYVINDSANNRYKNLKKTIQNIPPMIF
YP_007354410   694         MITTYQKIKDSVLDIGCGRGGDLIKFIHANIREYVQIDIDNNGLYVINDSAFNRYKNLKKTNKNIPPMIF
moumou_CR_04    23         MITTYQKDGDKVLDIGCGRGGDLIKFIHAGIEEYVQIDIDNNGLYVINDSAFNRYKNLKKTIKNIPPMIF -------------------------- MTase ---------------------------
                           780        790        800        810        820        830        840
                           ....|....|....|....|....|....|....|....|....|....|....|....|....|....|
AAV50651       770         INADARGLEDIEAQEKILPGMPDFNKSLINKYLVGN-KYDTINCQFTIHYYLSDELSWNNFCKNINNQLK
YP_007354410   764         INADARGLENIEAQEKILPNMSESNKKLINNYLSSNKKYDAINCQFTIHYYLSDDISWNNFCQNINNHLK
moumou_CR_04    93         INADARGLENIEAQEKILP---------------------------------------------------

------------------------- MTase ----------------------------
                           850        860        870        880        890        900        910
                           ....|....|....|....|....|....|....|....|....|....|....|....|....|....|
AAV50651       839         DNGYLLITSPDGNLIHNKLKGKQKLSSSYTDNRGNKNIFFEINKIYSDTDKVGLGMAIDLYNSLISNPGT
YP_007354410   834         DNGYLLITCFDGQLIYDKLKGKQKYSSSYTDNFGKKNIFFEINKIYSDEEIKPVGMAIDIYNSLISNPGT ------------- MTase -----------------|
                           920        930        940        950        960        970        980
                           ....|....|....|....|....|....|....|....|....|....|....|....|....|....|
AAV50651       909         YIREYLVFPEFLEKSLKEKCGLELVESDLFYNIFNTYKNYFKKTYNEYGMTDVSSKKHSEIREFYLSLEG
YP_007354410   904         YQREYLVFPDFLQKSLKDQCGLELVETDMFYNIFNLYRNYFTINNGIFSTGEISSKRYNEIKDFYLALEG 990       1000       1010       1020       1030       1040       1050
                           ....|....|....|....|....|....|....|....|....|....|....|....|....|....|
AAV50651       979         NANNDIEIDIARASFKLAMLNRYYVERKTSTINITEPSRIVNELNNRIDLGKFIMPYFRTNNMFIDLDNV
YP_007354410   974         KSSSVIESDIARASFKLAMLNRYYIFKKKTVINITEPSHIVSGVNKKIDLGKVLMPYFITNNMIIDYSLG 1060       1070       1080       1090       1100       1110       1120
                           ....|....|....|....|....|....|....|....|....|....|....|....|....|....|
AAV50651      1049         DTDINRVYRNIRNKYRTTRPHVYLIKHNINENRLEDIYLSNNKLDFSKIKNGSDPKVLLIYKSPDKQFYP
YP_007354410  1044         NNDVNKIYHFIRKKYSPIKPSVYIVRHNIIDNPMDGITFSRNKLEFIKIKNGTDPKVLLIYKSPEKIFYP 1130       1140       1150       1160       1170
                           ....|....|....|....|....|....|....|....|....|
AAV50651      1119         LYYQNYQSMPFDLD----QIYIPDKKKYLLDSDRIINDLNILINLTEKIKNIPQLS
YP_007354410  1114         FYYQRLENHDYSEDYLKNNIYIKDNGTYLLDSNKILNDLNMLVNISGKV-------
```

FIG. 6 (Cont.)

SEQUENCE LISTING

<160> NUMBER OF SEQ ID NOS: 21

<210> SEQ ID NO 1
<211> LENGTH: 844
<212> TYPE: PRT
<213> ORGANISM: Vaccinia virus
<220> FEATURE:
<221> NAME/KEY: misc_feature
<223> OTHER INFORMATION: FL VCE capping enzyme; >YP_232988.1 large
      subunit of mRNA capping enzyme

<400> SEQUENCE: 1

```
Met Asp Ala Asn Val Val Ser Ser Thr Ile Ala Thr Tyr Ile Asp
1               5                   10                  15

Ala Leu Ala Lys Asn Ala Ser Glu Leu Glu Gln Arg Ser Thr Ala Tyr
                20                  25                  30

Glu Ile Asn Asn Glu Leu Glu Leu Val Phe Ile Lys Pro Pro Leu Ile
            35                  40                  45

Thr Leu Thr Asn Val Val Asn Ile Ser Thr Ile Gln Glu Ser Phe Ile
        50                  55                  60

Arg Phe Thr Val Thr Asn Lys Glu Gly Val Lys Ile Arg Thr Lys Ile
65                  70                  75                  80

Pro Leu Ser Lys Val His Gly Leu Asp Val Lys Asn Val Gln Leu Val
                85                  90                  95

Asp Ala Ile Asp Asn Ile Val Trp Glu Lys Lys Ser Leu Val Thr Glu
                100                 105                 110

Asn Arg Leu His Lys Glu Cys Leu Leu Arg Leu Ser Thr Glu Glu Arg
            115                 120                 125

His Ile Phe Leu Asp Tyr Lys Lys Tyr Gly Ser Ser Ile Arg Leu Glu
        130                 135                 140

Leu Val Asn Leu Ile Gln Ala Lys Thr Lys Asn Phe Thr Ile Asp Phe
145                 150                 155                 160

Lys Leu Lys Tyr Phe Leu Gly Ser Gly Ala Gln Ser Lys Ser Ser Leu
                165                 170                 175

Leu His Ala Ile Asn His Pro Lys Ser Arg Pro Asn Thr Ser Leu Glu
            180                 185                 190

Ile Glu Phe Thr Pro Arg Asp Asn Glu Thr Val Pro Tyr Asp Glu Leu
        195                 200                 205
```

```
Ile Lys Glu Leu Thr Thr Leu Ser Arg His Ile Phe Met Ala Ser Pro
    210                 215                 220

Glu Asn Val Ile Leu Ser Pro Pro Ile Asn Ala Pro Ile Lys Thr Phe
225                 230                 235                 240

Met Leu Pro Lys Gln Asp Ile Val Gly Leu Asp Leu Glu Asn Leu Tyr
                245                 250                 255

Ala Val Thr Lys Thr Asp Gly Ile Pro Ile Thr Ile Arg Val Thr Ser
                260                 265                 270

Asn Gly Leu Tyr Cys Tyr Phe Thr His Leu Gly Tyr Ile Ile Arg Tyr
            275                 280                 285

Pro Val Lys Arg Ile Ile Asp Ser Glu Val Val Phe Gly Glu Ala
290                 295                 300

Val Lys Asp Lys Asn Trp Thr Val Tyr Leu Ile Lys Leu Ile Glu Pro
305                 310                 315                 320

Val Asn Ala Ile Asn Asp Arg Leu Glu Glu Ser Lys Tyr Val Glu Ser
                325                 330                 335

Lys Leu Val Asp Ile Cys Asp Arg Ile Val Phe Lys Ser Lys Lys Tyr
            340                 345                 350

Glu Gly Pro Phe Thr Thr Thr Ser Glu Val Val Asp Met Leu Ser Thr
            355                 360                 365

Tyr Leu Pro Lys Gln Pro Glu Gly Val Ile Leu Phe Tyr Ser Lys Gly
370                 375                 380

Pro Lys Ser Asn Ile Asp Phe Lys Ile Lys Lys Glu Asn Thr Ile Asp
385                 390                 395                 400

Gln Thr Ala Asn Val Val Phe Arg Tyr Met Ser Ser Glu Pro Ile Ile
                405                 410                 415

Phe Gly Glu Ser Ser Ile Phe Val Glu Tyr Lys Lys Phe Ser Asn Asp
                420                 425                 430

Lys Gly Phe Pro Lys Glu Tyr Gly Ser Gly Lys Ile Val Leu Tyr Asn
            435                 440                 445

Gly Val Asn Tyr Leu Asn Asn Ile Tyr Cys Leu Glu Tyr Ile Asn Thr
450                 455                 460

His Asn Glu Val Gly Ile Lys Ser Val Val Pro Ile Lys Phe Ile
465                 470                 475                 480

Ala Glu Phe Leu Val Asn Gly Glu Ile Leu Lys Pro Arg Ile Asp Lys
                485                 490                 495

Thr Met Lys Tyr Ile Asn Ser Glu Asp Tyr Tyr Gly Asn Gln His Asn
                500                 505                 510

Ile Ile Val Glu His Leu Arg Asp Gln Ser Ile Lys Ile Gly Asp Ile
            515                 520                 525

Phe Asn Glu Asp Lys Leu Ser Asp Val Gly His Gln Tyr Ala Asn Asn
530                 535                 540

Asp Lys Phe Arg Leu Asn Pro Glu Val Ser Tyr Phe Thr Asn Lys Arg
545                 550                 555                 560

Thr Arg Gly Pro Leu Gly Ile Leu Ser Asn Tyr Val Lys Thr Leu Leu
                565                 570                 575

Ile Ser Met Tyr Cys Ser Lys Thr Phe Leu Asp Asp Ser Asn Lys Arg
                580                 585                 590

Lys Val Leu Ala Ile Asp Phe Gly Asn Gly Ala Asp Leu Glu Lys Tyr
            595                 600                 605

Phe Tyr Gly Glu Ile Ala Leu Leu Val Ala Thr Asp Pro Asp Ala Asp
610                 615                 620

Ala Ile Ala Arg Gly Asn Glu Arg Tyr Asn Lys Leu Asn Ser Gly Ile
```

```
                625                 630                 635                 640
Lys Thr Lys Tyr Tyr Lys Phe Asp Tyr Ile Gln Glu Thr Ile Arg Ser
                    645                 650                 655

Asp Thr Phe Val Ser Ser Val Arg Glu Val Phe Tyr Phe Gly Lys Phe
                    660                 665                 670

Asn Ile Ile Asp Trp Gln Phe Ala Ile His Tyr Ser Phe His Pro Arg
                    675                 680                 685

His Tyr Ala Thr Val Met Asn Asn Leu Ser Glu Leu Thr Ala Ser Gly
                    690                 695                 700

Gly Lys Val Leu Ile Thr Thr Met Asp Gly Asp Lys Leu Ser Lys Leu
705                 710                 715                 720

Thr Asp Lys Lys Thr Phe Ile Ile His Lys Asn Leu Pro Ser Ser Glu
                    725                 730                 735

Asn Tyr Met Ser Val Glu Lys Ile Ala Asp Asp Arg Ile Val Val Tyr
                    740                 745                 750

Asn Pro Ser Thr Met Ser Thr Pro Met Thr Glu Tyr Ile Ile Lys Lys
                    755                 760                 765

Asn Asp Ile Val Arg Val Phe Asn Glu Tyr Gly Phe Val Leu Val Asp
                    770                 775                 780

Asn Val Asp Phe Ala Thr Ile Ile Glu Arg Ser Lys Lys Phe Ile Asn
785                 790                 795                 800

Gly Ala Ser Thr Met Glu Asp Arg Pro Ser Thr Arg Asn Phe Phe Glu
                    805                 810                 815

Leu Asn Arg Gly Ala Ile Lys Cys Glu Gly Leu Asp Val Glu Asp Leu
                    820                 825                 830

Leu Ser Tyr Tyr Val Val Tyr Val Phe Ser Lys Arg
                    835                 840

<210> SEQ ID NO 2
<211> LENGTH: 60
<212> TYPE: PRT
<213> ORGANISM: Faustovirus
<220> FEATURE:
<221> NAME/KEY: MISC_FEATURE
<223> OTHER INFORMATION: Fausto_CR_01

<400> SEQUENCE: 2

Phe Asp Lys Leu Lys Pro Asp Gly Glu Ile Thr Thr Thr Met Arg Val
1               5                   10                  15

Ser Asn Ala Asp Gly Met Ala Arg Glu Ile Thr Phe Gly Gly Gly Val
                20                  25                  30

Lys Thr Gly Glu Met Phe Val Lys Lys Gln Asn Ile Cys Val Phe Asp
            35                  40                  45

Val Val Asp Ile Phe Ser Tyr Lys Val Ala Val Ser
        50                  55                  60

<210> SEQ ID NO 3
<211> LENGTH: 111
<212> TYPE: PRT
<213> ORGANISM: Faustovirus
<220> FEATURE:
<221> NAME/KEY: misc_feature
<223> OTHER INFORMATION: Fausto_CR_03

<400> SEQUENCE: 3

Gly Phe Tyr Gly Asn Asn Tyr Lys Ile Ala Ser Asp Ile Tyr Leu Asn
1               5                   10                  15

Tyr Ile Asp Val Phe Asn Phe Asp Asp Leu Trp Lys Tyr Asn Pro Gly
```

```
                20                  25                  30

Tyr Phe Glu Lys Asn Lys Ser Asp Ile Tyr Ile Ala Pro Asn Lys Tyr
            35                  40                  45

Arg Arg Tyr Leu Ile Lys Ser Leu Phe Asn Lys Tyr Ile Lys Asn Ala
        50                  55                  60

Lys Trp Val Ile Asp Ala Ala Ala Gly Arg Gly Ala Asp Leu His Leu
 65                  70                  75                  80

Tyr Lys Ala Glu Cys Val Glu Asn Leu Leu Ala Ile Asp Ile Asp Pro
                85                  90                  95

Thr Ala Ile Ser Glu Leu Ile Arg Arg Arg Asn Glu Ile Thr Gly
            100                 105                 110

<210> SEQ ID NO 4
<211> LENGTH: 60
<212> TYPE: PRT
<213> ORGANISM: Faustovirus
<220> FEATURE:
<221> NAME/KEY: MISC_FEATURE
<223> OTHER INFORMATION: Fausto_CR_05

<400> SEQUENCE: 4

Lys Tyr Ser Ile Lys Arg Leu Tyr Asp Ser Asp Lys Leu Thr Lys Thr
 1               5                   10                  15

Gly Gln Lys Ile Ala Val Leu Leu Pro Met Ser Gly Glu Met Lys Glu
            20                  25                  30

Glu Pro Leu Cys Asn Ile Lys Asn Ile Ile Ser Met Ala Arg Lys Met
        35                  40                  45

Gly Leu Asp Leu Val Glu Ser Ala Asn Phe Ser Val
    50                  55                  60

<210> SEQ ID NO 5
<211> LENGTH: 67
<212> TYPE: PRT
<213> ORGANISM: Mimivirus
<220> FEATURE:
<221> NAME/KEY: MISC_FEATURE
<223> OTHER INFORMATION: 5: mimi_CR_03

<400> SEQUENCE: 5

Ile Asn Asp Asn Thr Val Val Glu Phe Ile Phe Asp Asn Phe Lys Ile
 1               5                   10                  15

Asp Met Asp Asp Pro Tyr Lys Trp Ile Pro Ile Arg Thr Arg Tyr Asp
            20                  25                  30

Lys Thr Glu Ser Val Gln Lys Tyr His Lys Lys Tyr Gly Asn Asn Leu
        35                  40                  45

His Ile Ala Asn Arg Ile Trp Lys Thr Ile Thr Asn Pro Ile Thr Glu
    50                  55                  60

Asp Ile Ile
65

<210> SEQ ID NO 6
<211> LENGTH: 111
<212> TYPE: PRT
<213> ORGANISM: Mimivirus
<220> FEATURE:
<221> NAME/KEY: MISC_FEATURE
<223> OTHER INFORMATION: mimi_CR_04

<400> SEQUENCE: 6

Tyr Tyr Gln Lys Asn Thr Ser Asn Ala Ala Gly Met Arg Ala Phe Asn
 1               5                   10                  15
```

-continued

```
Asn Phe Ile Lys Ser Asn Met Ile Thr Thr Tyr Cys Lys Asp Gly Asp
             20                  25                  30

Lys Val Leu Asp Ile Gly Cys Gly Arg Gly Asp Leu Ile Lys Phe
         35                  40                  45

Ile His Ala Gly Ile Glu Glu Tyr Val Gly Ile Asp Ile Asp Asn Asn
 50                  55                  60

Gly Leu Tyr Val Ile Asn Asp Ser Ala Phe Asn Arg Tyr Lys Asn Leu
 65                  70                  75                  80

Lys Lys Thr Ile Lys Asn Ile Pro Pro Met Thr Phe Ile Asn Ala Asp
             85                  90                  95

Ala Arg Gly Leu Phe Asn Leu Glu Ala Gln Lys Ile Leu Pro
            100                 105                 110

<210> SEQ ID NO 7
<211> LENGTH: 873
<212> TYPE: PRT
<213> ORGANISM: Faustovirus
<220> FEATURE:
<221> NAME/KEY: MISC_FEATURE
<223> OTHER INFORMATION: Faustovirus D5b RNA capping enzyme Genbank
      accession no. AMN83561

<400> SEQUENCE: 7

Met Ala Lys Arg Leu Gln Arg Cys Gln Asp Val Asn Gln Val Cys Glu
1               5                  10                  15

Ile Tyr Asn Ser Lys Gly Gly Ile Gly Glu Leu Glu Leu Arg Phe Asp
             20                  25                  30

Lys Leu Pro Gln Asn Leu Phe Ala Gly Val Phe Asp Lys Leu Lys Pro
         35                  40                  45

Asp Gly Glu Ile Gln Thr Thr Met Arg Val Ser Asn Arg Asp Gly Val
 50                  55                  60

Ala Arg Glu Ile Thr Phe Gly Gly Val Lys Thr Asn Glu Ile Phe
 65                  70                  75                  80

Val Lys Lys Gln Asn Ile Cys Val Phe Asp Val Val Asp Ile Phe Ser
             85                  90                  95

Tyr Lys Val Ala Val Ser Thr Glu Glu Thr Val Val Glu Lys Pro Thr
            100                 105                 110

Met Glu Thr Thr Ala Gly Val Arg Phe Lys Ile Arg Leu Ser Val Glu
            115                 120                 125

Asp Val Val Lys Asp Trp Arg Ile Asp Leu Thr Ala Val Lys Thr Ala
        130                 135                 140

Glu Leu Gly Lys Ile Ala Gln His Thr Ala Ser Ile Val Gln Arg Thr
145                 150                 155                 160

Phe Pro Asp Asn Leu Leu Lys Leu Thr Gly Ala Glu Val Ala Lys Leu
                165                 170                 175

Ala Ala Asp Ser Tyr Glu Leu Glu Leu Glu Tyr Thr Gly Lys Ser Pro
            180                 185                 190

Ala Thr Asn Glu Lys Val Asn Val Ala Ala Lys Tyr Ala Val Glu Leu
        195                 200                 205

Leu Ser Ser Val Arg Asn Ala Asn Ser Thr Ala Ala Ala Ser Phe Gly
    210                 215                 220

Glu Ser Val Ser Asp Leu Cys Arg Val Ala Lys Ile Ile His Thr His
225                 230                 235                 240

Glu Tyr Ala Asn Val Val Cys Arg Thr Pro Ser Phe Lys Met Leu Leu
                245                 250                 255
```

```
Pro Gln Val Val Ser Leu Thr Lys Ser Ser Tyr Gly Gly Leu Tyr
            260                 265                 270

Pro Pro Glu Asn Leu Trp Leu Ala Gly Lys Thr Asp Gly Val Arg Ala
        275                 280                 285

Leu Val Val Cys Glu Asp Gly Val Ala Lys Val Ile Thr Ala Glu Ser
    290                 295                 300

Val Asp Ile Thr His Gly Val Cys Ser Ala Thr Thr Ile Leu Asp Cys
305                 310                 315                 320

Glu Leu Asn Val Asp Ala Lys Ile Leu Tyr Val Phe Asp Val Ile Ile
                325                 330                 335

Ser Asn Asn Thr Gln Val Tyr Thr Gln Pro Phe Ser Thr Arg Ile Thr
            340                 345                 350

Thr Asp Ile Ser Asp Ile Lys Ile Asp Gly Tyr Lys Ile Glu Met Lys
        355                 360                 365

Pro Phe Val Lys Val Val Lys Ala Asp Glu Ala Thr Phe Lys Ser Ala
    370                 375                 380

Tyr Lys Ala Pro His Asn Glu Gly Leu Ile Met Ile Glu Asp Gly Ala
385                 390                 395                 400

Ala Tyr Ala Ala Thr Lys Thr Tyr Lys Trp Lys Pro Leu Ser His Asn
                405                 410                 415

Thr Ile Asp Phe Leu Ile Lys Ala Cys Pro Lys Gln Leu Ile Asn Val
            420                 425                 430

Asp Pro Tyr Lys Pro Arg Ala Gly Tyr Lys Leu Trp Leu Leu Phe Thr
        435                 440                 445

Thr Ile Ser Leu Asp Gln Gln Arg Glu Leu Gly Ile Glu Phe Ile Pro
    450                 455                 460

Ala Trp Lys Ile Leu Phe Thr Asp Ile Asn Met Phe Gly Ser Arg Val
465                 470                 475                 480

Pro Ile Gln Phe Gln Pro Ala Ile Asn Pro Leu Ala Tyr Val Cys Tyr
                485                 490                 495

Leu Pro Glu Asp Val Asn Val Asn Asp Gly Asp Ile Val Glu Met Arg
            500                 505                 510

Ala Val Asp Gly Tyr Asp Thr Ile Pro Lys Trp Glu Leu Val Arg Ser
        515                 520                 525

Arg Asn Asp Arg Lys Asn Glu Pro Gly Phe Tyr Gly Asn Asn Tyr Lys
    530                 535                 540

Ile Ala Ser Asp Ile Tyr Leu Asn Tyr Ile Asp Val Phe His Phe Glu
545                 550                 555                 560

Asp Leu Tyr Lys Tyr Asn Pro Gly Tyr Phe Glu Lys Asn Lys Ser Asp
                565                 570                 575

Ile Tyr Val Ala Pro Asn Lys Tyr Arg Arg Tyr Leu Ile Lys Ser Leu
            580                 585                 590

Phe Gly Arg Tyr Leu Arg Asp Ala Lys Trp Val Ile Asp Ala Ala Ala
        595                 600                 605

Gly Arg Gly Ala Asp Leu His Leu Tyr Lys Ala Glu Cys Val Glu His
    610                 615                 620

Leu Leu Ala Ile Asp Ile Asp Pro Thr Ala Ile Ser Glu Leu Val Arg
625                 630                 635                 640

Arg Arg Asn Glu Ile Thr Gly Tyr Asn Lys Ser His Arg Gly Gly Arg
                645                 650                 655

Asn Met His Ser His Arg Gly Gln Ser His Cys Ala Lys Ser Thr Ser
            660                 665                 670

Leu His Ala Leu Val Ala Asp Leu Arg Glu Asn Pro Asp Val Leu Ile
```

-continued

```
                675                 680                 685
Pro Lys Ile Ile Gln Ser Arg Pro His Glu Arg Cys Tyr Asp Ala Ile
            690                 695                 700

Val Ile Asn Phe Ala Ile His Tyr Leu Cys Asp Thr Asp Glu His Ile
705                 710                 715                 720

Arg Asp Phe Leu Ile Thr Val Ser Arg Leu Leu Ala Pro Asn Gly Val
                725                 730                 735

Phe Ile Phe Thr Thr Met Asp Gly Glu Ser Ile Val Lys Leu Leu Ala
                740                 745                 750

Asp His Lys Val Arg Pro Gly Glu Ala Trp Thr Ile His Thr Gly Asp
                755                 760                 765

Val Asn Ser Pro Asp Ser Thr Val Pro Lys Tyr Ser Ile Arg Arg Leu
770                 775                 780

Tyr Asp Ser Asp Lys Leu Thr Lys Thr Gly Gln Gln Ile Glu Val Leu
785                 790                 795                 800

Leu Pro Met Ser Gly Glu Met Lys Ala Glu Pro Leu Cys Asn Ile Lys
                805                 810                 815

Asn Ile Ile Ser Met Ala Arg Lys Met Gly Leu Asp Leu Val Glu Ser
                820                 825                 830

Ala Asn Phe Ser Val Leu Tyr Glu Ala Tyr Ala Arg Asp Tyr Pro Asp
                835                 840                 845

Ile Tyr Ala Arg Met Thr Pro Asp Asp Lys Leu Tyr Asn Asp Leu His
                850                 855                 860

Thr Tyr Ala Val Phe Lys Arg Lys Lys
865                 870
```

<210> SEQ ID NO 8
<211> LENGTH: 890
<212> TYPE: PRT
<213> ORGANISM: Faustovirus
<220> FEATURE:
<221> NAME/KEY: MISC_FEATURE
<223> OTHER INFORMATION: Faustovirus E12 RNA capping enzyme; Genbank
      accession no. AIB52055

<400> SEQUENCE: 8

```
Met Arg Arg Val Phe Asn Ser Ala Lys Lys Gln Gln Arg Cys Asp Ser
1               5                   10                  15

Val Glu Gln Val Cys Glu Phe Tyr Asn Ala Asp Asn Lys Thr Asn Glu
            20                  25                  30

Leu Glu Leu Arg Phe Asp Lys Leu Asn Arg Glu Leu Phe Val Val Leu
        35                  40                  45

Phe Asp Lys Leu Lys Pro Asp Gly Glu Ile Thr Thr Thr Met Arg Val
    50                  55                  60

Ser Asn Ala Asp Gly Met Ala Arg Glu Ile Thr Phe Gly Gly Gly Val
65                  70                  75                  80

Lys Thr Gly Glu Met Phe Val Lys Lys Gln Asn Ile Cys Val Phe Asp
                85                  90                  95

Val Val Asp Val Phe Ser Tyr Lys Val Ala Val Ser Ser Glu Asp Glu
            100                 105                 110

Ile Lys Asp Lys Pro Lys Met Asp Thr Asn Ala Ser Val Arg Phe Lys
        115                 120                 125

Ile Arg Leu Ser Cys Asp Thr Leu Ile Pro Asp Trp Arg Ile Asp Leu
    130                 135                 140

Thr Ala Val Lys Val Ala Asp Leu Gly Lys Ile Ala Gln His Thr Ser
145                 150                 155                 160
```

```
Thr Val Val Leu Gln Thr Phe Pro Glu Asn Leu Leu Arg Met Lys Gly
                165                 170                 175

Ala Glu Val Ala Ala Leu Ala Thr Asn Ser Tyr Glu Leu Glu Leu Glu
            180                 185                 190

Tyr Ile Gly Lys Ser Ala Ser Lys Glu Lys Val Leu Ala Ala Ala
        195                 200                 205

Glu Tyr Ala Met Glu Leu Leu Thr Asn Ser Arg Asn Ala Ile Ser Pro
    210                 215                 220

Ala Ala Ala Thr Leu Gly Glu Ser Val Ser Asp Ile Cys Arg Ile Ala
225                 230                 235                 240

Lys Leu Ile His Pro Ala Glu Tyr Ala Asn Val Ile Cys Arg Thr Pro
                245                 250                 255

Ser Phe Lys Asn Leu Leu Pro Gln Val Ile Ser Leu Thr Lys Ser Ser
            260                 265                 270

Tyr Tyr Gly Gly Ile Tyr Pro Pro Val Asp Met Tyr Ile Ala Gly Lys
        275                 280                 285

Thr Asp Gly Val Arg Ala Leu Val Leu Cys Glu Asn Gly Val Ala Lys
    290                 295                 300

Ile Ile Thr Ala Thr Thr Val Asp Thr Thr Val Gly Asn Thr Pro
305                 310                 315                 320

Ile Thr Ile Leu Asp Cys Glu Leu Ser Thr Ser Gly His Asn Gly Ala
                325                 330                 335

Thr Asp Asn Lys His Leu Tyr Ile Phe Asp Val Ile Met Asn Arg Gly
            340                 345                 350

Val His Ser His Arg Glu Gly Phe Asn Lys Arg Ile Asp Ile Asp Leu
        355                 360                 365

Ser Asp Leu Thr Pro Ala Gly Tyr Thr Leu Glu Leu Lys Pro Phe Thr
    370                 375                 380

Lys Leu Val Asp Ala Ala Ser Val Asn Glu Thr Thr Phe Lys Ser Val
385                 390                 395                 400

Phe Lys Pro Pro His Asn Glu Gly Leu Val Leu Val Glu Ser Gly Pro
                405                 410                 415

Pro Tyr Ala Leu Thr Lys Thr Tyr Lys Trp Lys Pro Ile Thr His Asn
            420                 425                 430

Thr Ile Asp Phe Leu Ile Lys Ala Cys Pro Lys Gln Leu Ile Asn Val
    435                 440                 445

Asp Pro Phe Lys Pro Arg Asn Gly His Asp Leu Trp Leu Leu Phe Thr
450                 455                 460

Thr Ile Ser Leu Asp Gln Gln Arg Glu Leu Gly Ile Asp Leu Ile Pro
465                 470                 475                 480

Ala Trp Lys Leu Leu Phe Thr Asp Val Asn Leu Phe Gly Asn Lys Ile
                485                 490                 495

Pro Ile Gln Phe Met Pro Ala Ile Asn Pro Leu Ala Tyr Ile Cys Tyr
            500                 505                 510

Leu Pro Ser Ser Thr Gly Val Asn Asp Gly Asp Ile Val Glu Met Arg
    515                 520                 525

Ala Val Asp Gly Phe Asp Gly Ile Pro Thr Trp Glu Leu Val Arg Thr
530                 535                 540

Arg Pro Asp Arg Lys Asp Glu Arg Gly Phe Tyr Gly Asn Asn Tyr Lys
545                 550                 555                 560

Ile Ala Ser Asp Ile Tyr Leu Asn Tyr Ile Asp Val Phe Asn Phe Asp
                565                 570                 575
```

```
Asp Leu Trp Lys Tyr Asn Pro Gly Tyr Phe Glu Lys Asn Lys Ser Asp
            580                 585                 590

Ile Tyr Ile Ala Pro Asn Lys Tyr Arg Arg Tyr Leu Ile Lys Ser Leu
        595                 600                 605

Phe Asn Lys Tyr Ile Lys Asn Ala Lys Trp Val Ile Asp Ala Ala Ala
    610                 615                 620

Gly Arg Gly Ala Asp Leu His Leu Tyr Lys Gln Glu Cys Val Glu Asn
625                 630                 635                 640

Leu Leu Ala Ile Asp Ile Pro Thr Ala Ile Ser Glu Leu Ile Arg
                645                 650                 655

Arg Arg Asn Glu Ile Thr Gly Trp Gln Gln Arg Gly Arg Gly Gly Asn
                660                 665                 670

Thr Arg His Asn Ala Arg His Asn Thr His Cys Ala Ser Ser Thr Ser
        675                 680                 685

Leu His Ala Leu Val Ala Asp Leu Arg Thr Glu Pro Asn Met Leu Ile
    690                 695                 700

Pro Lys Ile Ile Gln Ser Arg Pro Glu Arg Gly Tyr Asp Ala Ile
705                 710                 715                 720

Val Ile Asn Phe Ala Ile His Tyr Leu Cys Glu Thr Asp Asp Tyr Ile
                725                 730                 735

Arg Asn Phe Leu Ile Thr Val Ser Arg Leu Leu Ala Pro Asp Gly Val
                740                 745                 750

Phe Ile Phe Thr Thr Met Asp Gly Glu Ala Ile Val Asn Leu Leu Ala
            755                 760                 765

Glu His Lys Val Ala Pro Gly Ala Ser Trp Val Val His Thr Asp Gly
    770                 775                 780

Asn Ala Asn Ala Thr Asp Ala Asn Val Val Lys Tyr Ser Ile Lys Arg
785                 790                 795                 800

Leu Tyr Asp Ser Asp Lys Leu Thr Lys Thr Gly Gln Lys Ile Ala Val
                805                 810                 815

Leu Leu Pro Met Ser Gly Glu Met Arg Glu Pro Leu Cys Asn Ile
                820                 825                 830

Lys Asn Ile Val Ser Met Ala Arg Lys Met Gly Leu Asp Leu Val Glu
            835                 840                 845

Ser Ala Asn Phe Ser Val Leu Tyr Gly Ala Tyr Ala Lys Asp Tyr Pro
850                 855                 860

Glu Ile Tyr Ala Lys Leu Thr Pro Asp Asp Lys Leu Tyr Asn Asp Leu
865                 870                 875                 880

His Ala Phe Ala Val Phe Lys Arg Lys Lys
                885                 890

<210> SEQ ID NO 9
<211> LENGTH: 894
<212> TYPE: PRT
<213> ORGANISM: Faustovirus
<220> FEATURE:
<221> NAME/KEY: MISC_FEATURE
<223> OTHER INFORMATION: Faustovirus ST1 RNA capping enzyme; Genbank
      accession no. SME65026

<400> SEQUENCE: 9

Met Arg Arg Val Ser Asn Ser Ala Lys Lys Gln Gln Arg Cys Asp Ser
1               5                   10                  15

Val Glu Gln Val Cys Glu Phe Tyr Asn Ala Asp Asn Lys Thr Asn Glu
            20                  25                  30

Leu Glu Leu Arg Phe Asp Lys Leu Asn Arg Glu Leu Phe Val Ala Leu
```

```
            35                  40                  45
Phe Asp Lys Leu Lys Pro Asp Gly Glu Ile Thr Thr Thr Met Arg Val
 50                  55                  60
Ser Asn Ala Asp Gly Met Ala Arg Glu Ile Thr Phe Gly Gly Gly Val
 65                  70                  75                  80
Lys Thr Gly Glu Met Phe Val Lys Lys Gln Asn Ile Cys Val Phe Asp
                 85                  90                  95
Val Val Asp Val Phe Ser Tyr Lys Val Ala Val Ser Ser Glu Asp Glu
                100                 105                 110
Val Lys Asp Lys Pro Lys Met Asp Thr Asn Ala Ser Val Arg Phe Lys
            115                 120                 125
Ile Arg Leu Ser Cys Asp Thr Leu Ile Pro Asp Trp Arg Ile Asp Leu
            130                 135                 140
Thr Ala Val Lys Val Ala Asp Leu Gly Lys Ile Ala Gln His Thr Ser
145                 150                 155                 160
Thr Val Val Leu Gln Thr Phe Pro Glu Asn Leu Leu Arg Met Lys Gly
                165                 170                 175
Ala Glu Val Ala Ala Leu Ala Thr Asn Ser Tyr Glu Leu Glu Leu Glu
                180                 185                 190
Tyr Ile Gly Lys Ser Thr Ala Gly Lys Glu Lys Val Leu Lys Ala Ala
            195                 200                 205
Glu Tyr Ala Ile Glu Leu Leu Thr Asn Leu Arg Asn Ala Val Ser Pro
210                 215                 220
Val Ala Ala Thr Leu Gly Glu Ser Val Ser Asp Ile Cys Arg Ile Ala
225                 230                 235                 240
Lys Leu Ile His Pro Ala Glu Tyr Ala Asn Val Ile Cys Arg Thr Pro
                245                 250                 255
Ser Phe Lys Asn Leu Leu Pro Gln Val Ile Ser Leu Thr Lys Ser Ser
                260                 265                 270
Tyr Tyr Gly Gly Ile Tyr Pro Pro Val Asp Met Tyr Ile Thr Gly Lys
            275                 280                 285
Thr Asp Gly Val Arg Ala Leu Val Leu Cys Glu Asn Gly Val Ala Lys
            290                 295                 300
Ile Ile Thr Ala Thr Thr Val Asp Thr Thr Thr Val Gly Asp Thr Pro
305                 310                 315                 320
Ile Thr Ile Leu Asp Cys Glu Leu Ser Thr Ser Gly His Asn Gly Ala
                325                 330                 335
Thr Asp Asn Lys His Leu Tyr Val Phe Asp Val Ile Met Asn Arg Gly
            340                 345                 350
Ala His Ser His Arg Asp Gly Phe Asn Lys Arg Ile Asp Ile Asp Leu
            355                 360                 365
Ser Asp Leu Thr Pro Ala Gly Tyr Thr Leu Glu Leu Lys Pro Phe Thr
            370                 375                 380
Lys Val Ala Asp Ala Ala Ser Val Asn Glu Thr Thr Phe Lys Ser Val
385                 390                 395                 400
Phe Lys Pro Pro His Asn Glu Gly Leu Val Leu Val Glu Ser Gly Pro
                405                 410                 415
Pro Tyr Ala Leu Thr Lys Thr Tyr Lys Trp Lys Pro Ile Thr His Asn
            420                 425                 430
Thr Ile Asp Phe Leu Ile Lys Ala Cys Pro Lys Gln Leu Ile Asn Val
            435                 440                 445
Asp Pro Phe Lys Pro Arg Asn Gly His Asp Leu Trp Leu Leu Phe Thr
450                 455                 460
```

Thr Ile Ser Leu Asp Gln Gln Arg Glu Leu Gly Ile Asp Leu Ile Pro
465                 470                 475                 480

Ala Trp Lys Leu Leu Phe Thr Asp Val Asn Leu Phe Gly Asn Lys Ile
                485                 490                 495

Pro Ile Gln Phe Met Pro Ala Ile Asn Pro Leu Ala Tyr Ile Cys Tyr
            500                 505                 510

Leu Pro Ser Ser Thr Gly Val Asn Asp Gly Asp Ile Val Glu Met Arg
        515                 520                 525

Ala Val Asp Gly Phe Asp Gly Ile Pro Thr Trp Glu Leu Val Arg Thr
530                 535                 540

Arg Pro Asp Arg Lys Asp Glu Arg Gly Phe Tyr Gly Asn Asn Tyr Lys
545                 550                 555                 560

Ile Ala Ser Asp Ile Tyr Leu Asn Tyr Ile Asp Val Phe Asn Phe Asp
                565                 570                 575

Asp Leu Trp Lys Tyr Asn Pro Gly Tyr Phe Glu Lys Asn Lys Ser Asp
            580                 585                 590

Ile Tyr Ile Ala Pro Asn Lys Tyr Arg Arg Tyr Leu Ile Lys Ser Leu
        595                 600                 605

Phe Asn Lys Tyr Ile Lys Asn Ala Lys Trp Val Ile Asp Ala Ala Ala
610                 615                 620

Gly Arg Gly Ala Asp Leu His Leu Tyr Lys Gln Glu Cys Val Glu Asn
625                 630                 635                 640

Leu Leu Ala Ile Asp Ile Asp Pro Thr Ala Ile Ser Glu Leu Ile Arg
                645                 650                 655

Arg Arg Asn Glu Ile Thr Gly Trp Gln Gln Arg Gly Arg Gly Gly Asn
            660                 665                 670

Met His His Asn Ser Arg His Asn Thr Arg His Asn Thr His Cys Ala
        675                 680                 685

Ser Ser Thr Ser Leu His Ala Leu Val Ala Asp Leu Arg Thr Glu Pro
690                 695                 700

Asn Met Leu Ile Pro Lys Ile Ile Gln Ser Arg Pro Pro Glu Arg Gly
705                 710                 715                 720

Tyr Asp Ala Leu Val Ile Asn Phe Ala Ile His Tyr Leu Cys Glu Thr
                725                 730                 735

Asp Asp Tyr Ile Arg Asn Phe Leu Ile Thr Val Ser Arg Leu Leu Ala
            740                 745                 750

His Asp Gly Val Phe Ile Phe Thr Thr Met Asp Gly Glu Ala Ile Val
        755                 760                 765

Asn Leu Leu Thr Glu His Lys Val Ala Pro Gly Ala Ser Trp Val Val
770                 775                 780

His Thr Asp Gly Asn Thr Asn Ala Thr Asp Ala Asn Val Val Lys Tyr
785                 790                 795                 800

Ser Ile Lys Arg Leu Tyr Asp Ser Asp Lys Leu Thr Lys Thr Gly Gln
                805                 810                 815

Lys Ile Ala Val Leu Leu Pro Met Ser Gly Glu Met Arg Glu Pro
            820                 825                 830

Leu Cys Asn Ile Lys Asn Ile Val Ser Met Ala Arg Lys Met Gly Leu
        835                 840                 845

Asp Leu Val Glu Ser Ala Asn Phe Ser Val Leu Tyr Gly Ala Tyr Ala
850                 855                 860

Lys Asp Tyr Pro Glu Ile Tyr Ala Lys Leu Thr Pro Asp Asp Lys Leu
865                 870                 875                 880

Tyr Asn Asp Leu His Ala Phe Ala Val Phe Lys Arg Lys Lys
            885                 890

<210> SEQ ID NO 10
<211> LENGTH: 901
<212> TYPE: PRT
<213> ORGANISM: Faustovirus
<220> FEATURE:
<221> NAME/KEY: MISC_FEATURE
<223> OTHER INFORMATION: Faustovirus ST1 RNA capping enzyme; Genbank
      accession no. SMH63629

<400> SEQUENCE: 10

Leu Glu Tyr Gln Tyr Tyr Lys Tyr Ile Leu Val Asn Ile Met Ser Arg
1               5                   10                  15

Arg Leu Gln Arg Cys Arg Asp Val Asp Gln Val Cys Glu Tyr Tyr Asn
            20                  25                  30

Ala Lys Gly Ala Ile Gly Glu Leu Glu Leu Arg Phe Asp Lys Leu Thr
        35                  40                  45

Pro Asp Leu Phe Ala His Val Phe Asp Lys Leu Lys Pro Asp Gly Glu
    50                  55                  60

Ile Ser Thr Thr Met Arg Val Ser Asn Ser Asp Gly Thr Ala Arg Glu
65                  70                  75                  80

Ile Thr Phe Gly Gly Gly Val Lys Thr Gly Glu Thr Phe Val Arg Lys
                85                  90                  95

Gln Asn Ile Cys Val Phe Asp Val Val Asp Ile Phe Ser Tyr Lys Val
            100                 105                 110

Ala Val Ser Thr Glu Glu Thr Leu Val Asp Lys Pro Ala Met Glu Lys
        115                 120                 125

Asp Ala Ser Val Arg Phe Lys Ile Arg Met Ser Val Glu Gly Ala Val
    130                 135                 140

Pro Asn Trp Arg Ile Asp Leu Thr Ala Val Lys Thr Ala Glu Leu Gly
145                 150                 155                 160

Lys Ile Ala Gln His Thr Ala Ser Leu Val Leu Gln Thr Phe Pro Pro
                165                 170                 175

Asn Leu Leu Lys Met Ser Gly Ala Glu Val Ala Lys Leu Ala Asn Asn
            180                 185                 190

Ser Tyr Glu Leu Glu Leu Glu Tyr Ile Gly Lys Thr Pro Ala Thr Lys
        195                 200                 205

Glu Arg Val Asp Ala Ala Lys Tyr Ala Val Asp Leu Leu Ala Gly
    210                 215                 220

Ile Lys Asn Ala Asn Ser Ala Val Gly Ala Val Leu Gly Glu Ser Ile
225                 230                 235                 240

Ser Asp Ile Cys Arg Val Ala Lys Val Ile His Thr Pro Asp Tyr Ala
                245                 250                 255

Thr Val Val Cys Arg Asn Pro Ser Phe Lys Met Leu Leu Pro Gln Val
            260                 265                 270

Ile Ser Leu Thr Lys Ser Ser Tyr Tyr Gly Ile Tyr Pro Pro Glu
        275                 280                 285

Gly Met Tyr Val Ala Gly Lys Thr Asp Gly Val Arg Ala Leu Val Leu
    290                 295                 300

Cys Glu Asp Gly Val Ala Lys Val Ile Thr Ala Glu Ser Val Asp Ile
305                 310                 315                 320

Thr Thr Gly Thr Cys Thr Gly Thr Thr Ile Leu Asp Cys Glu Leu Ser
                325                 330                 335

Thr Gly Lys Ser Gly Ala Thr Leu His Val Phe Asp Ile Ile Met His

```
                    340                 345                 350
Asn Ser Lys Pro Ile His Ser Gln Pro Phe Ser Thr Arg Ile Ala Thr
        355                 360                 365

Asp Ile Ser Asp Val Lys Ile Pro Glu Tyr Lys Ile Ala Ile Lys Pro
    370                 375                 380

Phe Val Lys Ile Gln Ala Thr Ala Leu Glu Ala Ala Phe Lys Glu Val
385                 390                 395                 400

Tyr Lys Ala Pro His Asn Glu Gly Leu Ile Leu Ile Met Asp Gly Asn
                405                 410                 415

Asp Tyr Ala Met Thr Lys Thr Tyr Lys Trp Lys Pro Leu Ser His Asn
            420                 425                 430

Thr Ile Asp Phe Leu Ile Lys Ala Cys Pro Lys Gln Leu Leu Asn Ile
        435                 440                 445

Asp Pro Tyr Lys Pro Arg Pro Gly His Lys Leu Trp Leu Leu Phe Thr
    450                 455                 460

Thr Ile Ser Leu Asp Gln Gln Arg Glu Leu Gly Ile Glu Phe Ile Pro
465                 470                 475                 480

Ala Trp Lys Met Leu Phe Thr Asp Ile Asn Leu Phe Gly Ser Arg Val
                485                 490                 495

Pro Ile Gln Phe Met Pro Ala Ile Asn Pro Leu Ala Tyr Ile Cys Tyr
            500                 505                 510

Leu Pro Glu Ala Ala Thr Cys Ala Asn Gly Asp Ala Ile Asn Asp Gly
        515                 520                 525

Asp Ile Val Glu Met Arg Ala Val Asp Gly Phe Asp Thr Val Pro Lys
    530                 535                 540

Trp Glu Pro Ile Arg Val Arg Ser Asp Arg Lys Asp Glu Pro Gly Phe
545                 550                 555                 560

Tyr Gly Asn Asn Tyr Lys Ile Ala Ser Asp Ile Tyr Leu Asn Tyr Ile
                565                 570                 575

Asp Ile Phe Gln Phe Glu Asp Leu Tyr Lys Tyr Asn Pro Gly Tyr Phe
            580                 585                 590

Glu Lys Asn Lys Ser Asp Ile Tyr Val Ala Pro Asn Lys Tyr Arg Arg
        595                 600                 605

Phe Leu Ile Lys Asn Ile Phe Ser Lys Tyr Leu Lys Asn Ala Lys Trp
    610                 615                 620

Val Ile Asp Ala Ala Gly Arg Gly Ala Asp Leu His Leu Tyr Lys
625                 630                 635                 640

Ala Glu Cys Val Glu Asn Leu Leu Ala Ile Asp Ile Pro Thr Ala
                645                 650                 655

Ile Ser Glu Leu Val Arg Arg Arg Asn Glu Ile Thr Gly Tyr Asn Arg
            660                 665                 670

Gly His Arg Gly His Arg Gly Gly Ser Met Arg Ala His Met Gly Ala
        675                 680                 685

Ser His His Gly Ala Gln Asn Cys Ala Lys Ser Thr Thr Leu His Ala
    690                 695                 700

Leu Val Ala Asp Leu Arg Thr Asp Pro Asp Val Leu Ile Pro Lys Ile
705                 710                 715                 720

Ile Gln Ser Arg Pro Pro Glu Arg Gly Tyr Asp Ala Ile Val Ile Asn
                725                 730                 735

Phe Ala Ile His Tyr Leu Cys Asp Thr Asp Glu His Ile Arg Asp Phe
            740                 745                 750

Leu Ile Thr Val Ser Arg Leu Leu Ala Pro Asn Gly Ile Phe Met Phe
        755                 760                 765
```

```
Thr Thr Met Asp Gly Glu Ser Ile Val Lys Leu Leu Glu Thr His Lys
        770                 775                 780

Val Lys Ser Gly Glu Ser Trp Thr Val His Thr Gly Ala Asp Asp Pro
785                 790                 795                 800

Glu Ala Gly Val Ile Lys Tyr Ser Ile Arg Arg Leu Tyr Asp Ser Asp
                805                 810                 815

Lys Leu Thr Lys Thr Gly Gln Gln Ile Ala Val Leu Leu Pro Met Ser
                820                 825                 830

Gly Glu Met Lys Thr Glu Pro Leu Cys Asn Ile Lys Asn Ile Ile Ser
            835                 840                 845

Ile Ala Arg Lys Met Gly Leu Asp Leu Val Glu Ser Ala Asp Phe Ser
850                 855                 860

Val Met Tyr Asp Ala Phe Ala Arg Ala Tyr Pro Glu Ile Ser Ala Arg
865                 870                 875                 880

Leu Thr Pro Asp Asp Lys Leu Tyr Asn Asp Leu His Ser Tyr Ala Val
                885                 890                 895

Phe Lys Arg Lys Lys
            900

<210> SEQ ID NO 11
<211> LENGTH: 1170
<212> TYPE: PRT
<213> ORGANISM: Acanthamoeba polyphaga
<220> FEATURE:
<221> NAME/KEY: MISC_FEATURE
<223> OTHER INFORMATION: mimivirus RNA capping enzyme; Genbank accession
      no. AAV50651

<400> SEQUENCE: 11

Met Gly Thr Lys Leu Lys Lys Ser Asn Asn Asp Ile Thr Ile Phe Ser
1               5                   10                  15

Glu Asn Glu Tyr Asn Glu Ile Val Glu Met Leu Arg Asp Tyr Ser Asn
            20                  25                  30

Gly Asp Asn Leu Glu Phe Glu Val Ser Phe Lys Asn Ile Asn Tyr Pro
        35                  40                  45

Asn Phe Met Arg Ile Thr Glu His Tyr Ile Asn Ile Thr Pro Glu Asn
    50                  55                  60

Lys Ile Glu Ser Asn Asn Tyr Leu Asp Ile Ser Leu Ile Phe Pro Asp
65                  70                  75                  80

Lys Asn Val Tyr Arg Val Ser Leu Phe Asn Gln Glu Gln Ile Gly Glu
                85                  90                  95

Phe Ile Thr Lys Phe Ser Lys Ala Ser Ser Asn Asp Ile Ser Arg Tyr
            100                 105                 110

Ile Val Ser Leu Asp Pro Ser Asp Ile Glu Ile Val Tyr Lys Asn
        115                 120                 125

Arg Gly Ser Gly Lys Leu Ile Gly Ile Asp Asn Trp Ala Ile Thr Ile
130                 135                 140

Lys Ser Thr Glu Glu Ile Pro Leu Val Ala Gly Lys Ser Lys Ile Ser
145                 150                 155                 160

Lys Pro Lys Ile Thr Gly Ser Glu Arg Ile Met Tyr Arg Tyr Lys Thr
                165                 170                 175

Arg Tyr Ser Phe Thr Ile Asn Lys Asn Ser Arg Ile Asp Ile Thr Asp
            180                 185                 190

Val Lys Ser Ser Pro Ile Ile Trp Lys Leu Met Thr Val Pro Ser Asn
        195                 200                 205
```

-continued

Tyr Glu Leu Glu Leu Glu Leu Ile Asn Lys Ile Asp Ile Asn Thr Leu
    210             215                 220

Glu Ser Glu Leu Leu Asn Val Phe Met Ile Ile Gln Asp Thr Lys Ile
225             230                 235                 240

Pro Ile Ser Lys Ala Glu Ser Asp Thr Val Val Glu Glu Tyr Arg Asn
            245                 250                 255

Leu Leu Asn Val Arg Gln Thr Asn Asn Leu Asp Ser Arg Asn Val Ile
        260                 265                 270

Ser Val Asn Ser Asn His Ile Ile Asn Phe Ile Pro Asn Arg Tyr Ala
            275                 280                 285

Val Thr Asp Lys Ala Asp Gly Glu Arg Tyr Phe Leu Phe Ser Leu Asn
    290                 295                 300

Ser Gly Ile Tyr Leu Leu Ser Ile Asn Leu Thr Val Lys Lys Leu Asn
305             310                 315                 320

Ile Pro Val Leu Glu Lys Arg Tyr Gln Asn Met Leu Ile Asp Gly Glu
                325                 330                 335

Tyr Ile Lys Thr Thr Gly His Asp Leu Phe Met Val Phe Asp Val Ile
            340                 345                 350

Phe Ala Glu Gly Thr Asp Tyr Arg Tyr Asp Asn Thr Tyr Ser Leu Pro
        355                 360                 365

Lys Arg Ile Ile Ile Ile Asn Asn Ile Ile Asp Lys Cys Phe Gly Asn
    370                 375                 380

Leu Ile Pro Phe Asn Asp Tyr Thr Asp Lys His Asn Asn Leu Glu Leu
385                 390                 395                 400

Asp Ser Ile Lys Thr Tyr Tyr Lys Ser Glu Leu Ser Asn Tyr Trp Lys
                405                 410                 415

Asn Phe Lys Asn Arg Leu Asn Lys Ser Thr Asp Leu Phe Ile Thr Arg
            420                 425                 430

Lys Leu Tyr Leu Val Pro Tyr Gly Ile Asp Ser Ser Glu Ile Phe Met
        435                 440                 445

Tyr Ala Asp Met Ile Trp Lys Leu Tyr Val Tyr Asn Glu Leu Thr Pro
    450                 455                 460

Tyr Gln Leu Asp Gly Ile Ile Tyr Thr Pro Ile Asn Ser Pro Tyr Leu
465                 470                 475                 480

Ile Arg Gly Gly Ile Asp Ala Tyr Asp Thr Ile Pro Met Glu Tyr Lys
                485                 490                 495

Trp Lys Pro Pro Ser Gln Asn Ser Ile Asp Phe Tyr Ile Arg Phe Lys
            500                 505                 510

Lys Asp Val Ser Gly Ala Asp Ala Val Tyr Tyr Asp Asn Ser Val Glu
        515                 520                 525

Arg Ala Glu Gly Lys Pro Tyr Lys Ile Cys Leu Leu Tyr Val Gly Leu
    530                 535                 540

Asn Lys Gln Gly Gln Glu Ile Pro Ile Gln Phe Lys Val Asn Gly Val
545                 550                 555                 560

Glu Gln Thr Ala Asn Ile Tyr Thr Lys Asp Gly Glu Ala Thr Asp Ile
                565                 570                 575

Asn Gly Asn Ala Ile Asn Asp Asn Thr Val Val Glu Phe Val Phe Asp
            580                 585                 590

Thr Leu Lys Ile Asp Met Asp Asp Ser Tyr Lys Trp Ile Pro Ile Arg
        595                 600                 605

Thr Arg Tyr Asp Lys Thr Glu Ser Val Gln Lys Tyr His Lys Arg Tyr
    610                 615                 620

Gly Asn Asn Leu Gln Ile Ala Asn Arg Ile Trp Lys Thr Ile Thr Asn

```
                625                 630                 635                 640

Pro Ile Thr Glu Asp Ile Ile Ser Ser Leu Gly Asp Pro Thr Thr Phe
                        645                 650                 655

Asn Lys Glu Ile Thr Leu Leu Ser Asp Phe Arg Asp Thr Lys Tyr Asn
                        660                 665                 670

Lys Gln Ala Leu Thr Tyr Tyr Gln Lys Asn Thr Ser Asn Ala Ala Gly
                        675                 680                 685

Met Arg Ala Phe Asn Asn Trp Ile Lys Ser Asn Met Ile Thr Thr Tyr
                        690                 695                 700

Cys Arg Asp Gly Ser Lys Val Leu Asp Ile Gly Cys Gly Arg Gly Gly
    705                 710                 715                 720

Asp Leu Ile Lys Phe Ile Asn Ala Gly Val Glu Phe Tyr Val Gly Ile
                        725                 730                 735

Asp Ile Asp Asn Asn Gly Leu Tyr Val Ile Asn Asp Ser Ala Asn Asn
                        740                 745                 750

Arg Tyr Lys Asn Leu Lys Lys Thr Ile Gln Asn Ile Pro Pro Met Tyr
                        755                 760                 765

Phe Ile Asn Ala Asp Ala Arg Gly Leu Phe Thr Leu Glu Ala Gln Glu
                        770                 775                 780

Lys Ile Leu Pro Gly Met Pro Asp Phe Asn Lys Ser Leu Ile Asn Lys
    785                 790                 795                 800

Tyr Leu Val Gly Asn Lys Tyr Asp Thr Ile Asn Cys Gln Phe Thr Ile
                        805                 810                 815

His Tyr Tyr Leu Ser Asp Glu Leu Ser Trp Asn Asn Phe Cys Lys Asn
                        820                 825                 830

Ile Asn Asn Gln Leu Lys Asp Asn Gly Tyr Leu Leu Ile Thr Ser Phe
                        835                 840                 845

Asp Gly Asn Leu Ile His Asn Lys Leu Lys Gly Lys Gln Lys Leu Ser
    850                 855                 860

Ser Ser Tyr Thr Asp Asn Arg Gly Asn Lys Asn Ile Phe Phe Glu Ile
    865                 870                 875                 880

Asn Lys Ile Tyr Ser Asp Thr Asp Lys Val Gly Leu Gly Met Ala Ile
                        885                 890                 895

Asp Leu Tyr Asn Ser Leu Ile Ser Asn Pro Gly Thr Tyr Ile Arg Glu
                        900                 905                 910

Tyr Leu Val Phe Pro Glu Phe Leu Glu Lys Ser Leu Lys Glu Lys Cys
                        915                 920                 925

Gly Leu Glu Leu Val Glu Ser Asp Leu Phe Tyr Asn Ile Phe Asn Thr
    930                 935                 940

Tyr Lys Asn Tyr Phe Lys Lys Thr Tyr Asn Glu Tyr Gly Met Thr Asp
    945                 950                 955                 960

Val Ser Ser Lys Lys His Ser Glu Ile Arg Glu Phe Tyr Leu Ser Leu
                        965                 970                 975

Glu Gly Asn Ala Asn Asn Asp Ile Glu Ile Asp Ile Ala Arg Ala Ser
                        980                 985                 990

Phe Lys Leu Ala Met Leu Asn Arg Tyr Tyr Val Phe Arg Lys Thr Ser
                        995                 1000                1005

Thr Ile Asn Ile Thr Glu Pro Ser Arg Ile Val Asn Glu Leu Asn
                 1010                1015                1020

Asn Arg Ile Asp Leu Gly Lys Phe Ile Met Pro Tyr Phe Arg Thr
                 1025                1030                1035

Asn Asn Met Phe Ile Asp Leu Asp Asn Val Asp Thr Asp Ile Asn
                 1040                1045                1050
```

```
Arg Val Tyr Arg Asn Ile Arg Asn Lys Tyr Arg Thr Thr Arg Pro
1055              1060                1065

His Val Tyr Leu Ile Lys His Asn Ile Asn Glu Asn Arg Leu Glu
1070              1075                1080

Asp Ile Tyr Leu Ser Asn Asn Lys Leu Asp Phe Ser Lys Ile Lys
1085              1090                1095

Asn Gly Ser Asp Pro Lys Val Leu Leu Ile Tyr Lys Ser Pro Asp
1100              1105                1110

Lys Gln Phe Tyr Pro Leu Tyr Tyr Gln Asn Tyr Gln Ser Met Pro
1115              1120                1125

Phe Asp Leu Asp Gln Ile Tyr Leu Pro Asp Lys Lys Lys Tyr Leu
1130              1135                1140

Leu Asp Ser Asp Arg Ile Ile Asn Asp Leu Asn Ile Leu Ile Asn
1145              1150                1155

Leu Thr Glu Lys Ile Lys Asn Ile Pro Gln Leu Ser
1160              1165                1170

<210> SEQ ID NO 12
<211> LENGTH: 1162
<212> TYPE: PRT
<213> ORGANISM: Acanthamoeba polyphaga
<220> FEATURE:
<221> NAME/KEY: misc_feature
<223> OTHER INFORMATION: moumouvirus RNA capping enzyme; Genbank
      accession no. YP_007354410

<400> SEQUENCE: 12

Met Val Thr Lys Asn Lys Ser Glu Asn Ile Arg Asp Ile Leu Gly Ser
1               5                   10                  15

Asp Asn Val Ser Arg Val Glu Glu Met Ile Asn Asn Phe Arg Lys Asn
                20                  25                  30

Arg Asn Thr Glu Phe Glu Ile Ser Val Arg Lys Ile Asn Tyr Ser Asn
            35                  40                  45

Tyr Ile Arg Ile Ser Glu Tyr Tyr Val Asn Thr Ser Ser Asp Ile Gln
        50                  55                  60

Gln Val Thr Ser Leu Asp Ile Ser Ile Ile Leu Glu Asp Gly Asn Thr
65                  70                  75                  80

Tyr Arg Val Ser Phe Leu Asn Glu Asn Leu Ile Asn Asp Phe Leu Ser
                85                  90                  95

Lys Tyr Ser Asn Met Lys Tyr Gly Asp Ile Val Lys Tyr Ile Leu Ala
                100                 105                 110

Leu Asn Pro Asn Asp Asp Ile Glu Ile Ile Tyr Lys Asn Arg Gly Ser
            115                 120                 125

Ala Asp Arg Leu Ser Ile Glu Asp Leu Asn Leu Val Val Lys Leu Thr
130                 135                 140

Glu Glu Val Pro Val Leu Asn Asn Thr Thr Lys Pro Lys Leu Ser Gly
145                 150                 155                 160

Arg Glu Lys Ile Leu Tyr Arg Tyr Lys Asn Arg Tyr Ser Phe Ile Ile
                165                 170                 175

Asp Asp Ile Thr Arg Ile Asp Ile Thr Asp Val Lys Glu Thr Pro Asn
            180                 185                 190

Ile Trp Glu Leu Ser Arg Lys Ile Ser Asn Tyr Glu Ile Glu Leu Glu
        195                 200                 205

Phe Thr Asn Asn Lys Ile Lys Ser Asn Gln Val Phe Glu Lys Ile Phe
210                 215                 220
```

```
Asp Leu Leu Arg Ile Val Gln Asn Thr Glu Ile Pro Ile Gly Ile Arg
225                 230                 235                 240

Glu Ser Lys Gln Val Ile Thr Asp Tyr Gln Asn Leu Leu Asn Leu Arg
            245                 250                 255

Ser Ser Asn His Leu Asp Ser Arg Asn Val Val Ser Ile Glu Thr Gln
                260                 265                 270

His Ile Val Lys Phe Val Pro Asn Arg Tyr Ala Ile Thr Asp Lys Ala
            275                 280                 285

Asp Gly Glu Arg Tyr Phe Leu Phe Ser Thr Pro Asn Gly Val Tyr Leu
290                 295                 300

Leu Ser Thr Asn Leu Thr Val Lys Lys Val Asn Ile Pro Val Leu Gln
305                 310                 315                 320

Lys Asp Phe Gln Asn Met Leu Leu Asp Gly Glu Leu Ile Asp Ile Asp
                325                 330                 335

Gly Lys Glu Leu Phe Met Val Phe Asp Val Val Tyr His Asn Gly Ile
                340                 345                 350

Asp Tyr Arg Tyr Asp Thr Asn Tyr Thr Leu Thr His Arg Ile Ile Ile
                355                 360                 365

Ile Asn Asp Ile Ile Asp Lys Ala Phe Asn Asn Leu Ile Pro Phe Thr
370                 375                 380

Asp Tyr Thr Asp Lys Tyr Asn Asn Leu Glu Leu Asp Lys Ile Lys Glu
385                 390                 395                 400

Phe Tyr Ser Asn Glu Ile Lys Thr Tyr Trp Lys Asn Phe Ser Lys Lys
                405                 410                 415

Leu Lys Asn Tyr Ser Gly Leu Phe Ile Ser Arg Lys Leu Tyr Phe Val
                420                 425                 430

Pro Tyr Gly Ile Asp Ser Ser Glu Val Phe Met Tyr Ala Asp Leu Val
            435                 440                 445

Trp Lys Leu Cys Val Tyr Asp Gln Leu Thr Pro Tyr Lys Leu Asp Gly
            450                 455                 460

Ile Ile Tyr Thr Pro Ile Ala Ser Pro Tyr Met Ile Lys Thr Ser Ala
465                 470                 475                 480

Asn Glu Leu Asp Ser Val Pro Met Glu Tyr Lys Trp Lys Pro Pro Ser
                485                 490                 495

Gln Asn Ser Ile Asp Phe Tyr Val Lys Phe Asp Lys Asp Ala Arg Gly
            500                 505                 510

Asn Glu Ala Ile Tyr Tyr Asp Asn Ala Val Val Arg Gly Glu Gly Arg
            515                 520                 525

Pro Tyr Lys Val Cys Gly Leu Phe Val Gly Leu Asn Lys Gly Gly Glu
            530                 535                 540

Glu Lys Pro Ile Ala Phe Lys Val Ala Gly Val Glu Gln Lys Ala Phe
545                 550                 555                 560

Ile Tyr Leu Thr Asn Asp Glu Ala Leu Asp Leu Ser Gly Asn Val Ile
                565                 570                 575

Asn Asp Asn Thr Val Val Glu Phe Ile Phe Asp Asn Phe Lys Thr Asp
                580                 585                 590

Met Asp Asp Pro Tyr Lys Trp Ile Pro Val Arg Thr Arg Tyr Asp Lys
            595                 600                 605

Thr Glu Ser Val Gln Lys Tyr Arg Lys Lys Tyr Gly Asn Asn Leu His
            610                 615                 620

Ile Ala Thr Arg Ile Trp Arg Thr Ile Thr Asn Pro Val Thr Glu Glu
625                 630                 635                 640

Ile Ile Ala Ala Leu Gly Asn Ala Ser Thr Phe Glu Lys Glu Met Ser
```

-continued

```
                645                 650                 655
Lys Leu Val Lys Met Asn Glu Ser Tyr Asn Lys Gln Ser Phe Ser Tyr
                660                 665                 670

Tyr Gln Lys Asn Thr Ser Asn Ala Ile Gly Met Arg Ala Phe Asn Asn
                675                 680                 685

Phe Ile Lys Ser Asn Met Ile Thr Thr Tyr Cys Lys Asp Lys Asp Ser
    690                 695                 700

Val Leu Asp Ile Gly Cys Gly Arg Gly Gly Asp Leu Ile Lys Phe Ile
705                 710                 715                 720

His Ala Asn Ile Arg Glu Tyr Val Gly Leu Asp Ile Asp Asn Asn Gly
                725                 730                 735

Leu Tyr Val Ile Asn Asp Ser Ala Phe Asn Arg Tyr Lys Asn Leu Lys
                740                 745                 750

Lys Thr Asn Lys Asn Val Pro Pro Met Thr Phe Ile Asn Ala Asp Ala
                755                 760                 765

Arg Gly Leu Phe Asn Val Glu Ala Gln Glu Lys Ile Leu Pro Asn Met
                770                 775                 780

Ser Glu Ser Asn Lys Lys Leu Ile Asn Asn Tyr Leu Ser Ser Asn Lys
785                 790                 795                 800

Lys Tyr Asp Ala Ile Asn Cys Gln Phe Thr Ile His Tyr Tyr Leu Ser
                    805                 810                 815

Asp Asp Ile Ser Trp Asn Asn Phe Cys Gln Asn Ile Asn Asn His Ile
                820                 825                 830

Lys Asp Asn Gly Tyr Leu Leu Ile Thr Cys Phe Asp Gly Gln Leu Ile
                835                 840                 845

Tyr Asp Lys Leu Lys Gly Lys Gln Lys Tyr Ser Ser Ser Tyr Thr Asp
850                 855                 860

Asn Phe Gly Lys Lys Asn Ile Phe Phe Glu Ile Asn Lys Ile Tyr Ser
865                 870                 875                 880

Asp Glu Glu Ile Lys Pro Val Gly Met Ala Ile Asp Ile Tyr Asn Ser
                    885                 890                 895

Leu Ile Ser Asn Pro Gly Thr Tyr Gln Arg Glu Tyr Leu Val Phe Pro
                900                 905                 910

Asp Phe Leu Gln Lys Ser Leu Lys Asp Gln Cys Gly Leu Glu Leu Val
            915                 920                 925

Glu Thr Asp Met Phe Tyr Asn Ile Phe Asn Leu Tyr Arg Asn Tyr Phe
            930                 935                 940

Thr Ile Asn Asn Gly Thr Phe Ser Thr Gly Glu Ile Ser Ser Lys Arg
945                 950                 955                 960

Tyr Asn Glu Ile Lys Asp Phe Tyr Leu Ala Leu Glu Gly Lys Ser Ser
                965                 970                 975

Ser Val Thr Glu Ser Asp Ile Ala Phe Ala Ser Phe Lys Leu Ala Met
                980                 985                 990

Leu Asn Arg Tyr Tyr Ile Phe Lys Lys Lys Thr Val Ile Asn Ile Thr
            995                 1000                1005

Glu Pro Ser His Ile Val Ser Gly Val Asn Lys Thr Asp Leu
    1010                1015                1020

Gly Lys Val Leu Met Pro Tyr Phe Ile Thr Asn Asn Met Ile Ile
    1025                1030                1035

Asp Tyr Ser Leu Gly Asn Asn Asp Val Asn Lys Ile Tyr His Phe
    1040                1045                1050

Ile Arg Lys Lys Tyr Ser Pro Ile Lys Pro Ser Val Tyr Leu Val
    1055                1060                1065
```

```
Arg His Asn Ile Ile Asp Asn Pro Met Asp Gly Ile Thr Phe Ser
    1070             1075             1080

Arg Asn Lys Leu Glu Phe Ile Lys Ile Lys Asn Gly Thr Asp Pro
    1085             1090             1095

Lys Val Leu Leu Ile Tyr Lys Ser Pro Glu Lys Ile Phe Tyr Pro
    1100             1105             1110

Phe Tyr Tyr Gln Arg Leu Glu Asn His Asp Tyr Ser Glu Asp Tyr
    1115             1120             1125

Leu Lys Asn Asn Ile Tyr Leu Lys Asp Asn Gly Thr Tyr Leu Leu
    1130             1135             1140

Asp Ser Asn Lys Ile Ile Asn Asp Leu Asn Met Leu Val Asn Ile
    1145             1150             1155

Ser Gly Lys Val
    1160

<210> SEQ ID NO 13
<211> LENGTH: 25
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: RNA1

<400> SEQUENCE: 13
guagaacuuc gucgaguacg cucaa                                       25

<210> SEQ ID NO 14
<211> LENGTH: 23
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: RNA2

<400> SEQUENCE: 14
gcaagucuuc gucgaguacu ugc                                         23

<210> SEQ ID NO 15
<211> LENGTH: 24
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: RNA3

<400> SEQUENCE: 15
ggcaagucuu cgucgaguac uugc                                        24

<210> SEQ ID NO 16
<211> LENGTH: 25
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: RNA4

<400> SEQUENCE: 16
```

```
gggcaagucu ucgucgagua cuugc                                            25

<210> SEQ ID NO 17
<211> LENGTH: 150
<212> TYPE: RNA
<213> ORGANISM: Artificial Sequence
<220> FEATURE:
<223> OTHER INFORMATION: Synthetic construct

<400> SEQUENCE: 17
gggagucuuc gccgagaggg ccaucgccag uugccgcaac cuguggggaau uucucuucca      60 guuuauccgg augcucaacg ugacuuuaa uccgguauc uuucucgaau ucuuaccga        120 cuucagcgag cucgacaaug cucuucccua                                     150

<210> SEQ ID NO 18
<211> LENGTH: 1753
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Sequence of the fluc transcript

<400> SEQUENCE: 18
gggucuagaa auaauuuugu uuaacuuuaa gaaggagaua uaaccaugaa aaucgaagaa       60 gguaaaagguc accaucacca ucaccacgga uccauggaag acgccaaaaa cauaaagaaa    120
ggcccggcgc cauucuaucc ucuagaggau ggaaccgcug gagagcaacu gcauaaggcu    180
augaagagau acgcccuggu uccuggaaca auugcuuuua cagaugcaca uaucgaggug    240
aacaucacgu acgcggaaua cuucgaaaug uccguucggu uggcagaagc uaugaaacga    300
uaugggcuga auacaaauca cagaaucguc guaugcagug aaaacucucu ucaauucuuu    360
augccggugu ugggcgcguu auuuaucgga guugcaguuu cgcccgcgaa cgacauuuau    420
aaugaacgug aauugcucaa caguaugaac auuucgcagc cuaccguagu guuuguuccc    480 aaaaagggu ugcaaaaaau uuugaacgug caaaaaaau uaccaauaau ccagaaaauu      540
auuaucaugg auucuaaaac ggauuaccag ggauuucagu cgauguacac guucgucaca    600
ucucaucuac cucccgguuu uaaugaauac gauuuuguac cagagucuuu gaucgugac     660 aaaacaauug cacugauaau gaauuccucu ggaucuacug gguuaccuaa ggugugggcc    720
cuuccgcaua gaacugccug cgucagauuc ucgcaugcca gagauccuau uuuuggcaau    780
caaaucauuc cggauacugc gauuuuaagu guuguuccau uccaucacgg uuuuggaaug    840
uuuacuacac ucggauauuu gauaugugga uuucgagucg cuuaaugua uagauuugaa    900 gaagagcugu uuuuacgauc ccuucaggau uacaaaauuc aaagugcguu gcuaguacca    960
acccuauuuu cauucuucgc caaaagcacu cugauugaca aauacgauuu aucuaauuua   1020
cacgaaauug cuucugggg cgcaccucuu ucgaagaag ucgggaagc gguugcaaaa      1080 cgcuuccauc uuccagggau acgacaagga uaugggcuca cugagacuac aucagcuauu    1140
cugauuacac ccgagggga ugauaaaccg ggcgcgguucg uaaaguugu uccauuuuuu    1200 gaagcgaagg uuguggaucu ggauaccggg aaaacgcugg gcguuaauca gagaggcgaa    1260 uuaugugucaa gaggaccuau gauuaugucc gguuauguaa acaauccgga agcgaccaac    1320
gccuugauug acaaggaugg auggcuacau ucuggagaca uagcuacug ggacgaagac    1380 gaacacuucu ucauaguuga ccgcuugaag ucuuuaauua aauacaaagg auaucaggug    1440
```

```
gcccccgcug aauuggaauc gauauuguua caacaccccca acaucuucga cgcgggcgug    1500
gcaggucuuc ccgacgauga cgccggugaa cuucccgccg ccguuguugu uuuggagcac    1560
ggaaagacga ugacggaaaa agagaucgug gauuacgucg ccagucaagu aacaaccgcg    1620
aaaaaguugc gcgaggagu uguguuugug gacgaaguac cgaaaggucu uaccggaaaa    1680
cucgacgcaa gaaaaaucag agagauccuc auaaaggcca agaagggcgg aaaguccaaa    1740
cucgaguaag guu                                                       1753
```

<210> SEQ ID NO 19
<211> LENGTH: 44
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Targeting oligo for fluc transcript
<220> FEATURE:
<221> NAME/KEY: misc_feature
<222> LOCATION: (44)..(44)
<223> OTHER INFORMATION: C is TEG-desthiobiotin

<400> SEQUENCE: 19

```
gttaaarcra rarararuru rarururure rurargrarc rcrc                      44
```

<210> SEQ ID NO 20
<211> LENGTH: 1778
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: The amino acid sequence of H3C2:T7 RNA
       polymerase fusion protein

<400> SEQUENCE: 20

```
Met Lys Ile Glu Glu His His His His His His Gly Ala Ser
 1               5                  10                  15

Thr Ala Lys Arg Leu Gln Arg Cys Gln Asp Val Asn Gln Val Cys Glu
            20                  25                  30

Ile Tyr Asn Ser Lys Gly Gly Ile Gly Glu Leu Glu Leu Arg Phe Asp
        35                  40                  45

Lys Leu Pro Gln Asn Leu Phe Ala Gly Val Phe Asp Lys Leu Lys Pro
    50                  55                  60

Asp Gly Glu Ile Gln Thr Thr Met Arg Val Ser Asn Arg Asp Gly Val
65                  70                  75                  80

Ala Arg Glu Ile Thr Phe Gly Gly Gly Val Lys Thr Asn Glu Ile Phe
                85                  90                  95

Val Lys Lys Gln Asn Ile Cys Val Phe Asp Val Val Asp Ile Phe Ser
            100                 105                 110

Tyr Lys Val Ala Val Ser Thr Glu Glu Thr Val Val Glu Lys Pro Thr
        115                 120                 125

Met Glu Thr Thr Ala Gly Val Arg Phe Lys Ile Arg Leu Ser Val Glu
    130                 135                 140

Asp Val Val Lys Asp Trp Arg Ile Asp Leu Thr Ala Val Lys Thr Ala
145                 150                 155                 160

Glu Leu Gly Lys Ile Ala Gln His Thr Ala Ser Ile Val Gln Arg Thr
                165                 170                 175
```

```
Phe Pro Asp Asn Leu Leu Lys Leu Thr Gly Ala Glu Val Ala Lys Leu
                180                 185                 190

Ala Ala Asp Ser Tyr Glu Leu Glu Leu Glu Tyr Thr Gly Lys Ser Pro
            195                 200                 205

Ala Thr Asn Glu Lys Val Asn Val Ala Ala Lys Tyr Ala Val Glu Leu
        210                 215                 220

Leu Ser Ser Val Arg Asn Ala Asn Ser Thr Ala Ala Ala Ser Phe Gly
225                 230                 235                 240

Glu Ser Val Ser Asp Leu Cys Arg Val Ala Lys Ile Ile His Thr His
                245                 250                 255

Glu Tyr Ala Asn Val Val Cys Arg Thr Pro Ser Phe Lys Met Leu Leu
            260                 265                 270

Pro Gln Val Val Ser Leu Thr Lys Ser Ser Tyr Tyr Gly Gly Leu Tyr
        275                 280                 285

Pro Pro Glu Asn Leu Trp Leu Ala Gly Lys Thr Asp Gly Val Arg Ala
    290                 295                 300

Leu Val Val Cys Glu Asp Gly Val Ala Lys Val Ile Thr Ala Glu Ser
305                 310                 315                 320

Val Asp Ile Thr His Gly Val Cys Ser Ala Thr Thr Ile Leu Asp Cys
                325                 330                 335

Glu Leu Asn Val Asp Ala Lys Ile Leu Tyr Val Phe Asp Val Ile Ile
            340                 345                 350

Ser Asn Asn Thr Gln Val Tyr Thr Gln Pro Phe Ser Thr Arg Ile Thr
        355                 360                 365

Thr Asp Ile Ser Asp Ile Lys Ile Asp Gly Tyr Lys Ile Glu Met Lys
    370                 375                 380

Pro Phe Val Lys Val Lys Ala Asp Glu Ala Thr Phe Lys Ser Ala
385                 390                 395                 400

Tyr Lys Ala Pro His Asn Glu Gly Leu Ile Met Ile Glu Asp Gly Ala
                405                 410                 415

Ala Tyr Ala Ala Thr Lys Thr Tyr Lys Trp Lys Pro Leu Ser His Asn
            420                 425                 430

Thr Ile Asp Phe Leu Ile Lys Ala Cys Pro Lys Gln Leu Ile Asn Val
        435                 440                 445

Asp Pro Tyr Lys Pro Arg Ala Gly Tyr Lys Leu Trp Leu Leu Phe Thr
    450                 455                 460

Thr Ile Ser Leu Asp Gln Gln Arg Glu Leu Gly Ile Glu Phe Ile Pro
465                 470                 475                 480

Ala Trp Lys Ile Leu Phe Thr Asp Ile Asn Met Phe Gly Ser Arg Val
                485                 490                 495

Pro Ile Gln Phe Gln Pro Ala Ile Asn Pro Leu Ala Tyr Val Cys Tyr
            500                 505                 510

Leu Pro Glu Asp Val Asn Val Asn Asp Gly Asp Ile Val Glu Met Arg
        515                 520                 525

Ala Val Asp Gly Tyr Asp Thr Ile Pro Lys Trp Glu Leu Val Arg Ser
    530                 535                 540

Arg Asn Asp Arg Lys Asn Glu Pro Gly Phe Tyr Gly Asn Asn Tyr Lys
545                 550                 555                 560

Ile Ala Ser Asp Ile Tyr Leu Asn Tyr Ile Asp Val Phe His Phe Glu
                565                 570                 575

Asp Leu Tyr Lys Tyr Asn Pro Gly Tyr Phe Glu Lys Asn Lys Ser Asp
            580                 585                 590

Ile Tyr Val Ala Pro Asn Lys Tyr Arg Arg Tyr Leu Ile Lys Ser Leu
```

```
                    595                 600                 605
Phe Gly Arg Tyr Leu Arg Asp Ala Lys Trp Val Ile Asp Ala Ala
610                 615                 620

Gly Arg Gly Ala Asp Leu His Leu Tyr Lys Ala Glu Cys Val Glu His
625                 630                 635                 640

Leu Leu Ala Ile Asp Ile Asp Pro Thr Ala Ile Ser Glu Leu Val Arg
                    645                 650                 655

Arg Arg Asn Glu Ile Thr Gly Tyr Asn Lys Ser His Arg Gly Gly Arg
                    660                 665                 670

Asn Met His Ser His Arg Gly Gln Ser His Cys Ala Lys Ser Thr Ser
                675                 680                 685

Leu His Ala Leu Val Ala Asp Leu Arg Glu Asn Pro Asp Val Leu Ile
            690                 695                 700

Pro Lys Ile Ile Gln Ser Arg Pro His Glu Arg Cys Tyr Asp Ala Ile
705                 710                 715                 720

Val Ile Asn Phe Ala Ile His Tyr Leu Cys Asp Thr Asp Glu His Ile
                725                 730                 735

Arg Asp Phe Leu Ile Thr Val Ser Arg Leu Leu Ala Pro Asn Gly Val
                740                 745                 750

Phe Ile Phe Thr Thr Met Asp Gly Glu Ser Ile Val Lys Leu Leu Ala
                755                 760                 765

Asp His Lys Val Arg Pro Gly Glu Ala Trp Thr Ile His Thr Gly Asp
770                 775                 780

Val Asn Ser Pro Asp Ser Thr Val Pro Lys Tyr Ser Ile Arg Arg Leu
785                 790                 795                 800

Tyr Asp Ser Asp Lys Leu Thr Lys Thr Gly Gln Gln Ile Glu Val Leu
                805                 810                 815

Leu Pro Met Ser Gly Glu Met Lys Ala Glu Pro Leu Cys Asn Ile Lys
                820                 825                 830

Asn Ile Ile Ser Met Ala Arg Lys Met Gly Leu Asp Leu Val Glu Ser
                835                 840                 845

Ala Asn Phe Ser Val Leu Tyr Glu Ala Tyr Ala Arg Asp Tyr Pro Asp
850                 855                 860

Ile Tyr Ala Arg Met Thr Pro Asp Asp Lys Leu Tyr Asn Asp Leu His
865                 870                 875                 880

Thr Tyr Ala Val Phe Lys Arg Lys Lys Gly Ala Ser Thr Ala Ser Thr
                885                 890                 895

Asn Thr Ile Asn Ile Ala Lys Asn Asp Phe Ser Asp Ile Glu Leu Ala
                900                 905                 910

Ala Ile Pro Phe Asn Thr Leu Ala Asp His Tyr Gly Glu Arg Leu Ala
                915                 920                 925

Arg Glu Gln Leu Ala Leu Glu His Glu Ser Tyr Glu Met Gly Glu Ala
                930                 935                 940

Arg Phe Arg Lys Met Phe Glu Arg Gln Leu Lys Ala Gly Glu Val Ala
945                 950                 955                 960

Asp Asn Ala Ala Ala Lys Pro Leu Ile Thr Thr Leu Leu Pro Lys Met
                965                 970                 975

Ile Ala Arg Ile Asn Asp Trp Phe Glu Glu Val Lys Ala Lys Arg Gly
                980                 985                 990

Lys Arg Pro Thr Ala Phe Gln Phe Leu Gln Glu Ile Lys Pro Glu Ala
                995                 1000                1005

Val Ala Tyr Ile Thr Ile Lys Thr Thr Leu Ala Cys Leu Thr Ser
        1010                1015                1020
```

```
Ala Asp Asn Thr Thr Val Gln Ala Val Ser Ala Ile Gly Arg
    1025            1030            1035

Ala Ile Glu Asp Glu Ala Arg Phe Gly Arg Ile Arg Asp Leu Glu
    1040            1045            1050

Ala Lys His Phe Lys Lys Asn Val Glu Glu Gln Leu Asn Lys Arg
    1055            1060            1065

Val Gly His Val Tyr Lys Lys Ala Phe Met Gln Val Val Glu Ala
    1070            1075            1080

Asp Met Leu Ser Lys Gly Leu Leu Gly Gly Glu Ala Trp Ser Ser
    1085            1090            1095

Trp His Lys Glu Asp Ser Ile His Val Gly Val Arg Cys Ile Glu
    1100            1105            1110

Met Leu Ile Glu Ser Thr Gly Met Val Ser Leu His Arg Gln Asn
    1115            1120            1125

Ala Gly Val Val Gly Gln Asp Ser Glu Thr Ile Glu Leu Ala Pro
    1130            1135            1140

Glu Tyr Ala Glu Ala Ile Ala Thr Arg Ala Gly Ala Leu Ala Gly
    1145            1150            1155

Ile Ser Pro Met Phe Gln Pro Cys Val Val Pro Pro Lys Pro Trp
    1160            1165            1170

Thr Gly Ile Thr Gly Gly Gly Tyr Trp Ala Asn Gly Arg Arg Pro
    1175            1180            1185

Leu Ala Leu Val Arg Thr His Ser Lys Lys Ala Leu Met Arg Tyr
    1190            1195            1200

Glu Asp Val Tyr Met Pro Glu Val Tyr Lys Ala Ile Asn Ile Ala
    1205            1210            1215

Gln Asn Thr Ala Trp Lys Ile Asn Lys Lys Val Leu Ala Val Ala
    1220            1225            1230

Asn Val Ile Thr Lys Trp Lys His Cys Pro Val Glu Asp Ile Pro
    1235            1240            1245

Ala Ile Glu Arg Glu Glu Leu Pro Met Lys Pro Glu Asp Ile Asp
    1250            1255            1260

Met Asn Pro Glu Ala Leu Thr Ala Trp Lys Arg Ala Ala Ala Ala
    1265            1270            1275

Val Tyr Arg Lys Asp Lys Ala Arg Lys Ser Arg Arg Ile Ser Leu
    1280            1285            1290

Glu Phe Met Leu Glu Gln Ala Asn Lys Phe Ala Asn His Lys Ala
    1295            1300            1305

Ile Trp Phe Pro Tyr Asn Met Asp Trp Arg Gly Arg Val Tyr Ala
    1310            1315            1320

Val Ser Met Phe Asn Pro Gln Gly Asn Asp Met Thr Lys Gly Leu
    1325            1330            1335

Leu Thr Leu Ala Lys Gly Lys Pro Ile Gly Lys Glu Gly Tyr Tyr
    1340            1345            1350

Trp Leu Lys Ile His Gly Ala Asn Cys Ala Gly Val Asp Lys Val
    1355            1360            1365

Pro Phe Pro Glu Arg Ile Lys Phe Ile Glu Glu Asn His Glu Asn
    1370            1375            1380

Ile Met Ala Cys Ala Lys Ser Pro Leu Glu Asn Thr Trp Trp Ala
    1385            1390            1395

Glu Gln Asp Ser Pro Phe Cys Phe Leu Ala Phe Cys Phe Glu Tyr
    1400            1405            1410
```

```
Ala Gly Val Gln His His Gly Leu Ser Tyr Asn Cys Ser Leu Pro
1415                1420                1425

Leu Ala Phe Asp Gly Ser Cys Ser Gly Ile Gln His Phe Ser Ala
1430                1435                1440

Met Leu Arg Asp Glu Val Gly Gly Arg Ala Val Asn Leu Leu Pro
1445                1450                1455

Ser Glu Thr Val Gln Asp Ile Tyr Gly Ile Val Ala Lys Lys Val
1460                1465                1470

Asn Glu Ile Leu Gln Ala Asp Ala Ile Asn Gly Thr Asp Asn Glu
1475                1480                1485

Val Val Thr Val Thr Asp Glu Asn Thr Gly Glu Ile Ser Glu Lys
1490                1495                1500

Val Lys Leu Gly Thr Lys Ala Leu Ala Gly Gln Trp Leu Ala Tyr
1505                1510                1515

Gly Val Thr Arg Ser Val Thr Lys Arg Ser Val Met Thr Leu Ala
1520                1525                1530

Tyr Gly Ser Lys Glu Phe Gly Phe Arg Gln Val Leu Glu Asp
1535                1540                1545

Thr Ile Gln Pro Ala Ile Asp Ser Gly Lys Gly Leu Met Phe Thr
1550                1555                1560

Gln Pro Asn Gln Ala Ala Gly Tyr Met Ala Lys Leu Ile Trp Glu
1565                1570                1575

Ser Val Ser Val Thr Val Val Ala Ala Val Glu Ala Met Asn Trp
1580                1585                1590

Leu Lys Ser Ala Ala Lys Leu Leu Ala Ala Glu Val Lys Asp Lys
1595                1600                1605

Lys Thr Gly Glu Ile Leu Arg Lys Arg Cys Ala Val His Trp Val
1610                1615                1620

Thr Pro Asp Gly Phe Pro Val Trp Gln Glu Tyr Lys Lys Pro Ile
1625                1630                1635

Gln Thr Arg Leu Asn Leu Met Phe Leu Gly Gln Phe Arg Leu Gln
1640                1645                1650

Pro Thr Ile Asn Thr Asn Lys Asp Ser Glu Ile Asp Ala His Lys
1655                1660                1665

Gln Glu Ser Gly Ile Ala Pro Asn Phe Val His Ser Gln Asp Gly
1670                1675                1680

Ser His Leu Arg Lys Thr Val Val Trp Ala His Glu Lys Tyr Gly
1685                1690                1695

Ile Glu Ser Phe Ala Leu Ile His Asp Ser Phe Gly Thr Ile Pro
1700                1705                1710

Ala Asp Ala Ala Asn Leu Phe Lys Ala Val Arg Glu Thr Met Val
1715                1720                1725

Asp Thr Tyr Glu Ser Cys Asp Val Leu Ala Asp Phe Tyr Asp Gln
1730                1735                1740

Phe Ala Asp Gln Leu His Glu Ser Gln Leu Asp Lys Met Pro Ala
1745                1750                1755

Leu Pro Ala Lys Gly Asn Leu Asn Leu Arg Asp Ile Leu Glu Ser
1760                1765                1770

Asp Phe Ala Phe Ala
    1775

<210> SEQ ID NO 21
<211> LENGTH: 5337
<212> TYPE: DNA
```

<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Nucleotide sequence of H3C2:T7 RNA polymerase fusion protein

<400> SEQUENCE: 21

| | | | | | |
|---|---|---|---|---|---|
| atgaagattg | aggagcatca | tcatcatcat | catcatcatg | gcgcgagcac | cgcgaagcgt | 60 |
| ctgcagcgtt | gccaggacgt | gaaccaagtg | tgcgaaatct | acaacagcaa | gggtggcatt | 120 |
| ggcgagctgg | aactgcgttt | cgataaactg | ccgcagaacc | tgttcgcggg | cgttttttgat | 180 |
| aagctgaaac | cggacggcga | gattcaaacc | accatgcgtg | ttagcaaccg | tgacggtgtg | 240 |
| gcgcgtgaaa | tcacctttgg | tggcggtgtt | aagaccaacg | agatcttcgt | gaagaaacag | 300 |
| aacatttgcg | ttttcgacgt | ggttgatatc | tttagctaca | aggtggcggt | tagcaccgag | 360 |
| gaaaccgtgg | ttgaaaagcc | gaccatggag | accaccgcgg | gcgtgcgttt | taaaattcgt | 420 |
| ctgagcgttg | aagacgtggt | taaggattgg | cgtatcgatc | tgaccgcggt | gaagaccgcg | 480 |
| gagctgggta | aaatcgcgca | gcacaccgcg | agcattgttc | aacgtaccct | cccggataac | 540 |
| ctgctgaagc | tgaccggtgc | ggaagtggcg | aaactggcgg | cggacagcta | cgagctggaa | 600 |
| ctggagtata | ccggcaagag | cccggcgacc | aacgaaaagg | tgaacgttgc | ggcgaaatac | 660 |
| gcggttgagc | tgctgagcag | cgtgcgtaac | gcgaacagca | ccgcggcggc | gagctttggt | 720 |
| gaaagcgtta | gcgacctgtg | ccgtgtggcg | aaaatcattc | acacccacga | gtacgcgaac | 780 |
| gtggtttgcc | gtaccccgag | cttcaaaatg | ctgctgccgc | aggtggttag | cctgaccaag | 840 |
| agcagctact | atggcggtct | gtatccgccg | gaaaacctgt | ggctggcggg | caagaccgat | 900 |
| ggcgtgcgtg | cgctggttgt | gtgcgaagac | ggcgtggcga | agttatcac | gcggagagc | 960 |
| gttgatatta | cccacggtgt | gtgcagcgcg | accaccattc | tggattgcga | gctgaacgtt | 1020 |
| gacgcgaaga | tcctgtacgt | gtttgacgtt | atcattagca | caacacccca | ggtgtatacc | 1080 |
| caaccgttca | gcacccgtat | caccaccgac | attagcgata | tcaagatcga | tggttacaag | 1140 |
| atcgaaatga | agccgtttgt | taaggtggtt | aaggcggacg | aggcgacctt | caagagcgcg | 1200 |
| tataaagcgc | cgcacaacga | aggcctgatc | atgattgaag | atggtgcggc | gtacgcggcg | 1260 |
| accaagacct | ataagtggaa | accgctgagc | cacaacacca | tcgatttcct | gattaaggcg | 1320 |
| tgcccgaaac | agctgattaa | cgtggacccg | tacaagccgc | gtgcgggtta | taaactgtgg | 1380 |
| ctgctgttta | ccaccatcag | cctggatcag | caacgtgaac | tgggcatcga | gttcattccg | 1440 |
| gcgtggaaaa | tcctgttcac | cgacattaac | atgtttggta | gccgtgtgcc | gatccagttt | 1500 |
| caaccggcga | ttaacccgct | ggcgtacgtt | tgctatctgc | cggaagacgt | gaacgttaac | 1560 |
| gacggcgata | ttgttgagat | gcgtgcggtg | gacggttacg | ataccatccc | gaaatgggaa | 1620 |
| ctggttcgta | gccgtaacga | tcgtaagaac | gagcccgggtt | tctacggcaa | caactataaa | 1680 |
| atcgcgagcg | acatttacct | gaactatatt | gatgttttcc | actttgaaga | cctgtacaaa | 1740 |
| tataacccgg | gctacttcga | gaagaacaag | agcgatatct | acgtggcgcc | gaacaagtac | 1800 |
| cgtcgttatc | tgatcaaaag | cctgttcggt | cgttacctgc | gtgatgcgaa | gtgggtgatt | 1860 |
| gatgcggcgg | cgggtcgtgg | cgcggacctg | cacctgtata | aagcggaatg | cgttgagcac | 1920 |
| ctgctggcga | tcgacattga | tccgaccgcg | atcagcgaac | tggtgcgtcg | tcgtaacgag | 1980 |
| attaccggct | acaacaagag | ccaccgtggc | ggtcgtaaca | tgcacagcca | ccgtggtcag | 2040 |
| agccactgcg | cgaaaagcac | cagcctgcac | gcgctggttg | cggatctgcg | tgaaaacccg | 2100 |

```
gacgttctga ttccgaagat cattcaaagc cgtccgcacg agcgttgcta cgatgcgatc    2160
gttattaact ttgcgatcca ctatctgtgc gacaccgatg aacacatccg tgacttcctg    2220
attaccgtga gccgtctgct ggcgccgaac ggtgttttca tctttaccac catggatggt    2280
gaaagcattg tgaagctgct ggcggaccac aaagttcgtc cgggtgaagc gtggaccatc    2340
cacaccggtg atgtgaacag cccggacagc accgttccga atacagcat tcgtcgtctg    2400 tatgacagcg ataagctgac caaaaccggc cagcaaatcg aggttctgct gccgatgagc    2460
ggtgaaatga aggcggagcc gctgtgcaac attaaaaaca tcattagcat ggcgcgtaag    2520
atgggtctgg atctggtgga aagcgcgaac tttagcgttc tgtacgaggc gtatgcgcgt    2580
gactacccgg atatctatgc gcgtatgacc ccggacgata agctgtacaa cgacctgcac    2640
acctatgcgg tgttcaagcg taagaaaggc gcgagcaccg cgagcaccaa caccatcaac    2700
attgcgaaga acgactttag cgatatcgag ctggcggcga ttccgttcaa caccctggcg    2760
gaccactacg gtgaacgtct ggcgcgtgag cagctggcgc tggaacacga gagctatgaa    2820
atgggcgagg cgcgtttccg taagatgttt gaacgtcaac tgaaagcggg tgaggttgcg    2880
gataacgcgc cggcgaaacc gctgattacc accctgctgc cgaagatgat cgcgcgtatt    2940
aacgactggt tcgaggaagt taaggcgaaa cgtggtaaac gtccgaccgc gttccagttt    3000
ctgcaagaaa tcaaaccgga ggcggtggcg tacatcacca ttaaaaccac cctggcgtgc    3060
ctgaccagcg cggacaacac caccgtgcag gcggttgcga gcgcgattgg tcgtgcgatt    3120
gaagatgagg cgcgttttgg tcgtatccgt gacctggaag cgaagcactt caagaaaaac    3180
gttgaggaac agctgaacaa acgtgtgggc cacgtttata agaaagcgtt catgcaagtg    3240
gttgaggcgg atatgctgag caagggtctg ctgggcggtg aagcgtggag cagctggcac    3300
aaagaggaca gcatccacgt gggcgttcgt tgcatcgaaa tgctgattga gagcaccggt    3360
atggttagcc tgcaccgtca gaacgcgggt gtggttggcc aagatagcga aaccatcgag    3420
ctggcgccgg aatacgcgga ggcgattgcg acccgtgcgg gtgcgctggc gggtatcagc    3480
ccgatgtttc aaccgtgcgt ggttccgccg aagccgtgga ccggtattac cggcggtggc    3540
tactgggcga acggtcgtcg tccgctggcg ctggtgcgta cccacagcaa gaaagcgctg    3600
atgcgttacg aagacgttta tatgccggaa gtgtataagg cgatcaacat tgcgcaaaac    3660
accgcgtgga aaattaacaa gaaagtgctg gcggttgcga acgtgatcac caagtggaaa    3720
cactgcccgg ttgaagatat cccggcgatt gagcgtgagg aactgccgat gaaaccggaa    3780
gacatcgata tgaacccgga agcgctgacc gcgtggaaac gtgcggcggc ggcggtgtac    3840
cgtaaggaca aagcgcgtaa aagccgtcgt attagcctgg aattcatgct ggagcaggcg    3900
aacaagtttg cgaaccacaa agcgatctgg ttcccgtaca acatggattg gcgtggccgt    3960
gtttatgctg tgagcatgtt caacccgcaa ggcaacgaca tgaccaaggg cctgctgacc    4020
ctggcgaagg gtaaaccgat tggcaaggaa ggctactatt ggctgaaaat ccacggtgcg    4080
aactgcgcgg gcgttgataa agtgccgttc ccggaacgta tcaagtttat tgaggaaaac    4140
cacgagaaca tcatggcgtg cgcgaaaagc ccgctggaaa acacctggtg ggcggagcag    4200
gacagcccgt tctgctttct ggcgttctgc tttgagtacg cgggtgttca acaccacggc    4260
ctgagctata actgcagcct gccgctggcg tttgatggta gctgcagcgg catccagcac    4320
ttcagcgcga tgctgcgtga cgaagttggt ggccgtgcgg tgaacctgct gccgagcgag    4380
accgtgcagg atatctacgg tattgttgcg aagaaagtga acgagatcct gcaagcggat    4440
```

```
gcgattaacg gcaccgacaa cgaagtggtt accgtgaccg acgagaacac cggtgaaatc    4500
agcgagaagg ttaaactggg taccaaagcg ctggcgggcc agtggctggc gtacggtgtt    4560
acccgtagcg tgaccaagcg tagcgttatg accctggcgt atggtagcaa agaattcggc    4620
tttcgtcagc aagtgctgga ggataccatc caaccggcga ttgacagcgg caagggcctg    4680
atgtttaccc agccgaacca agcggcgggt tacatggcga aactgatctg ggaaagcgtg    4740
agcgttaccg tggttgcggc ggttgaggcg atgaactggc tgaagagcgc ggcgaaactg    4800
ctggcggcgg aagtgaaaga taagaaaacc ggcgagattc tgcgtaagcg ttgcgcggtt    4860
cactgggtga ccccggacgg tttcccggtt tggcaggaat ataagaaacc gatccaaacc    4920
cgtctgaacc tgatgttcct gggccagttt cgtctgcaac cgaccatcaa caccaacaaa    4980
gatagcgaaa ttgacgcgca caagcaggag agcggcattg cgccgaactt tgtgcacagc    5040
caagacggta gccacctgcg taaaaccgtg gtttgggcgc acgaaaagta cggcatcgag    5100
agcttcgcgc tgattcacga tagctttggt accattccgg cggatgcggc gaacctgttc    5160
aaggcggttc gtgaaaccat ggtggatacc tacgagagct gcgacgtgct ggcggacttc    5220
tatgatcagt ttgcggatca actgcacgag agccagctgg acaaaatgcc ggcgctgccg    5280
gcgaagggta acctgaacct gcgtgacatt ctggagagcg attttgcgtt tgcgtaa      5337
```

ENZYMATIC RNA CAPPING METHOD

CROSS-REFERENCE TO RELATED APPLICATIONS

This application is a continuation of International Application No. PCT/US20/47521 filed Aug. 21, 2020 and a continuation of International Application No. PCT/US20/47533 filed Aug. 21, 2020. This application also claims priority to U.S. Provisional Application No. 62/890,821 filed Aug. 23, 2019. The contents of all of the above are hereby incorporated in their entirety by reference.

BACKGROUND

The addition of a cap to uncapped synthetic RNA is important for efficient protein expression in many eukaryotic cells. Moreover, uncapped RNAs (at least RNAs that have a 5'-triphosphate) are reported to activate the innate immune response (Pichlmair, et al., Science 2006 314: 997-1001; Diamond, et al., Cytokine & Growth Factor Reviews, 2014 25: 543-550). As such, it is highly desirable to add a cap to synthetic RNA in many therapeutic applications (e.g., protein replacement therapy as well as prophylactic or therapeutic vaccination).

Currently, two methods that are used to cap RNA. In the first method, synthetic RNAs (e.g., RNAs transcribed in vitro) are converted to capped RNAs using an RNA capping enzyme. In the other method (which is generally referred to as "co-transcriptional capping") cap analogs such as anti-reverse cap analog (ARCA) and capped dinucleotides are added to the in vitro transcription reaction. In the co-transcriptional methods, the cap is co-transcriptionally incorporated into RNA molecules during in vitro transcription.

Compared to the co-transcriptional capping method, the enzymatic RNA capping method can achieve higher yields of capped RNA. However, enzymatic RNA capping reactions are quite inefficient and, as such, either large amounts of enzyme are used, or the capped RNA must be purified from the uncapped RNA. Further, the efficiency of enzymatic RNA capping reactions (expressed as a percentage of capped RNA after the completion of a capping reaction) can vary from one RNA sequence to another, a difference that is generally attributed to RNA structure (see, e.g., Fuchs, R N A. 2016 22: 1454-66).

Therefore, there is still a need for a more efficient way to add cap to synthetic RNAs.

SUMMARY

This disclosure provides, among other things, a method for efficiently capping RNA in vitro. In some embodiments, a method may comprise contacting (i) an RNA sample comprising an uncapped target RNA, (ii) an RNA capping enzyme comprising an amino acid sequence that is at least 90% identical to (e.g., at least 95% identical to) SEQ ID NOS:1, 7 or 20, (iii) guanosine triphosphate (GTP) or modified GTP, (iv) a buffering agent, and optionally (v) a methyl group donor at a temperature in the range of 40° C.-60° C., to form (e.g., to efficiently form) a capped target RNA. The efficiency determined by yield of capped RNA (50%)/enzyme concentration (nM) may be improved by at least 2-fold or at least 3-fold compared to the capping efficiency of the enzyme at 37° C. An uncapped target RNA optionally may be free of modified nucleotides or may comprise one or more modified nucleotides (e.g., pseudouridine).

In some embodiments, a method may comprise contacting (i) an RNA sample comprising an uncapped target RNA, (ii) a single-chain RNA capping enzyme that has RNA triphosphatase (TPase), guanylyltransferase (GTase) and guanine-N7 methyltransferase (N7 MTase) activities, (iii) GTP or modified GTP, (iv) a buffering agent, and optionally (v) methyl group donor at a temperature in the range of 37° C.-60° C., to form (e.g., to efficiently form) a capped target RNA. A single-chain RNA capping enzyme (e.g., RNA capping enzymes from of giant viruses such as Faustovirus, Mimivirus or Moumouvirus) may comprise: (a) an amino acid sequence at least 90% identical to (e.g., at least 95% identical to) (x) SEQ ID NO:2, (y) SEQ ID NO:3, and/or (z) SEQ ID NO:4 or (b) an amino acid sequence at least 90% identical to (e.g., at least 95% identical to) (x) SEQ ID NO:5 and/or (y) SEQ ID NO:6. For example, RNA capping enzymes of giant viruses such as Faustovirus, Mimivirus or Moumouvirus may comprise an amino acid sequence at least 90% identical to (e.g., at least 95% identical to) (a) SEQ ID NO:2, (b) SEQ ID NO:3, (c) SEQ ID NO:4, (d) SEQ ID NO:5, and/or (e) SEQ ID NO:6. RNA capping enzymes from Faustovirus (which are examples of single-chain RNA capping enzymes) may comprises an amino acid sequence that is at least 90% identical to (a) SEQ ID NO:7, (b) SEQ ID NO:8, (c) SEQ ID NO:9, (d) SEQ ID NO:10, (e) SEQ ID NO:11 and/or (f) SEQ ID NO:12.

In some embodiments, an uncapped target RNA may be at least 200 nt in length (e.g., at least 300 nt, at least 500 nt or at least 1,000 nt) and may encode a polypeptide such as a therapeutic protein or vaccine. Target RNA having secondary structure including therapeutic RNA can be capped more efficiently using method of this disclosure. Efficiency may be defined as yield of capped RNA (50%)/enzyme concentration (nM). In any embodiment, a method may comprise contacting at a first temperature (e.g., 37° C.-60° C.) and increasing or decreasing the temperature (e.g., to 37° C.-60° C.) wherein the second temperature differs from the first temperature. For example, a method may include contacting at a first temperature of 37° C. for 1 to 120 minutes and increasing the temperature to 45° C. or 50° C. for 1 to 120 minutes. A method, in some embodiments, may include increasing or decreasing the temperature to a third temperature of 37° C.-60° C. for 1 to 120 minutes. A capping method, in some embodiments, may produce (e.g., may co-transcriptionally produce) more than 70% Cap0 RNA in vitro in one hour or less.

In some embodiments, the components and/or combinations thereof may be RNase-free and contacting may optionally further comprise (v) one or more RNase inhibitors.

The uncapped RNA may be synthesized using solid-phase oligonucleotide synthesis chemistry or by transcribing a DNA template using a polymerase (e.g., T7 RNA polymerase or Hi-T7 RNA polymerase) in an in vitro transcription reaction, for example, by contacting a DNA template encoding the uncapped target RNA and the polymerase.

In any embodiment, contacting may further comprise contacting SAM and/or a cap 2'O methyltransferase enzyme (2'OMTase).

Contacting, in any embodiment, may comprise contacting (i), (ii), (iii), (iv) and (v) in a single location, for example, in a single microfluidics surface, a single reaction tube or other reaction vessel.

Also provided herein is a composition comprising an uncapped target RNA, a single-chain RNA capping enzyme that has TPase, GTase and N7 MTase activities, GTP and a buffering agent. In some embodiments, a composition may have a temperature in the range of 37° C.-60° C. In some embodiments, a composition may be RNase-free and may optionally comprise one or more RNase inhibitors. In some embodiment, a single-chain RNA capping enzyme may comprise: (a) amino acid sequences that are at least 90% identical to (x) SEQ ID NO:2, (y) SEQ ID NO:3, and/or (z) SEQ ID NO:4 or (b) an amino acid sequence that is at least 90% identical to (x) SEQ ID NO:5 and/or (y) SEQ ID NO:6. A single-chain RNA capping enzyme may comprise an amino acid sequence that is at least 90% identical to the RNA capping enzyme of Faustovirus D5b (SEQ ID NO:7), Faustovirus E12 (SEQ ID NO:8), Faustovirus ST1 (SEQ ID NO:9), Faustovirus LC9 (SEQ ID NO:10), mimivirus (SEQ ID NO:11) or moumouvirus (SEQ ID NO:12). In some embodiments, a composition may further comprise a DNA template, a polymerase (e.g., a bacteriophage polymerase) and ribonucleotides, for transcribing the DNA template to form the uncapped target RNA. In some embodiments, a composition may further comprise SAM and/or a cap 2'OMTase. In some embodiments, a single uncapped target RNA may be at least 200 nt in length (at least 300 nt, at least 500 nt or at least 1,000 nt) and may encode a polypeptide such as a therapeutic protein or vaccine.

Also provided is a kit. In some embodiments, a kit may comprise a single-chain RNA capping enzyme that has TPase, GTase and N7 MTase activities, wherein the enzyme is in a storage buffering agent; and a concentrated reaction buffering agent. In some embodiments, a kit may further include a DNA template, a polymerase and ribonucleotides, for transcribing the RNA. In some embodiments, a kit may further include SAM and/or a cap 2'OMTase. Examples of the methods, compositions and kits that utilize methyl transferases may also include SAM in the reaction mix. A single-chain RNA capping enzyme may comprise: (a) an amino acid sequence at least 90% identical to (x) SEQ ID NO:2, (y) SEQ ID NO:3, and/or (z) SEQ ID NO:4 or (b) an amino acid sequence at least 90% identical to (x) SEQ ID NO:5 and/or (y) SEQ ID NO:6. The single-chain RNA capping enzyme may comprises an amino acid sequence that is at least 90% identical to the RNA capping enzyme of Faustovirus D5b (SEQ ID NO:7), Faustovirus E12 (SEQ ID NO:8), Faustovirus ST1 (SEQ ID NO:9), Faustovirus LC9 (SEQ ID NO:10), mimivirus (SEQ ID NO:11) or moumouvirus (SEQ ID NO:12).

In some embodiments, an RNA capping enzyme may an amino acid sequence that is at least 90% identical to SEQ ID NO:20. In some embodiments, an RNA capping enzyme fusion may comprise (a) an amino acid sequence that is at least 90% identical to SEQ ID NO:7 and (b) an amino acid sequence that is at least 90% identical to positions 1419 to 1587 of SEQ ID NO:20.

BRIEF DESCRIPTION OF THE FIGURES

FIG. 3A shows activity of VCE. FIG. 3B shows activity of H3C2. See Table 1 for a quantitative comparison of the capping activity under each condition.

FIG. 4A shows capping activity at 37° C. FIG. 4B shows capping activity at 45° C. FIG. 4C shows capping activity at 50° C. FIG. 4D shows capping activity at 55° C. FIG. 4E shows capping activity at 60° C.

FIG. 5 shows the conserved regions that exhibit 90% or higher sequence identity among the Faustovirus D5b, E12, ST1 and LC9 (SEQ ID NOS: 7-10) capping enzyme amino acid sequences mapped to AMH83561 (H3C2). The conserved regions are designated as Fausto_CR01, Fausto_CR_03 and Fausto_CR_05. Functional domains of H3C2 capping enzyme, namely TPase, GTase and N7 MTase, are indicated FIG. 6 shows the conserved regions that exhibit 90% or higher sequence identity among the *Acanthanomeba polyphaga* mimivirus (AAV50651, SEQ ID NO:11) and *Acanthanomeba polyphaga* moumouvirus capping enzyme amino acid sequences mapped to YP_007354410 (*Acanthanomeba polyphaga* moumouvirus capping enzyme; moumou CE) (SEQ ID NO:12). The conserved regions are designated as moumou_CR_03 (SEQ ID NO:6) and moumou_CR_04 (SEQ ID NO:7). Functional domains of moumou CE, namely TPase, GTase and N7 MTase. are indicated in this alignment with dashed lines above the aligned sequences. The conserved regions are highlighted.

DETAILED DESCRIPTION

Figure 1:
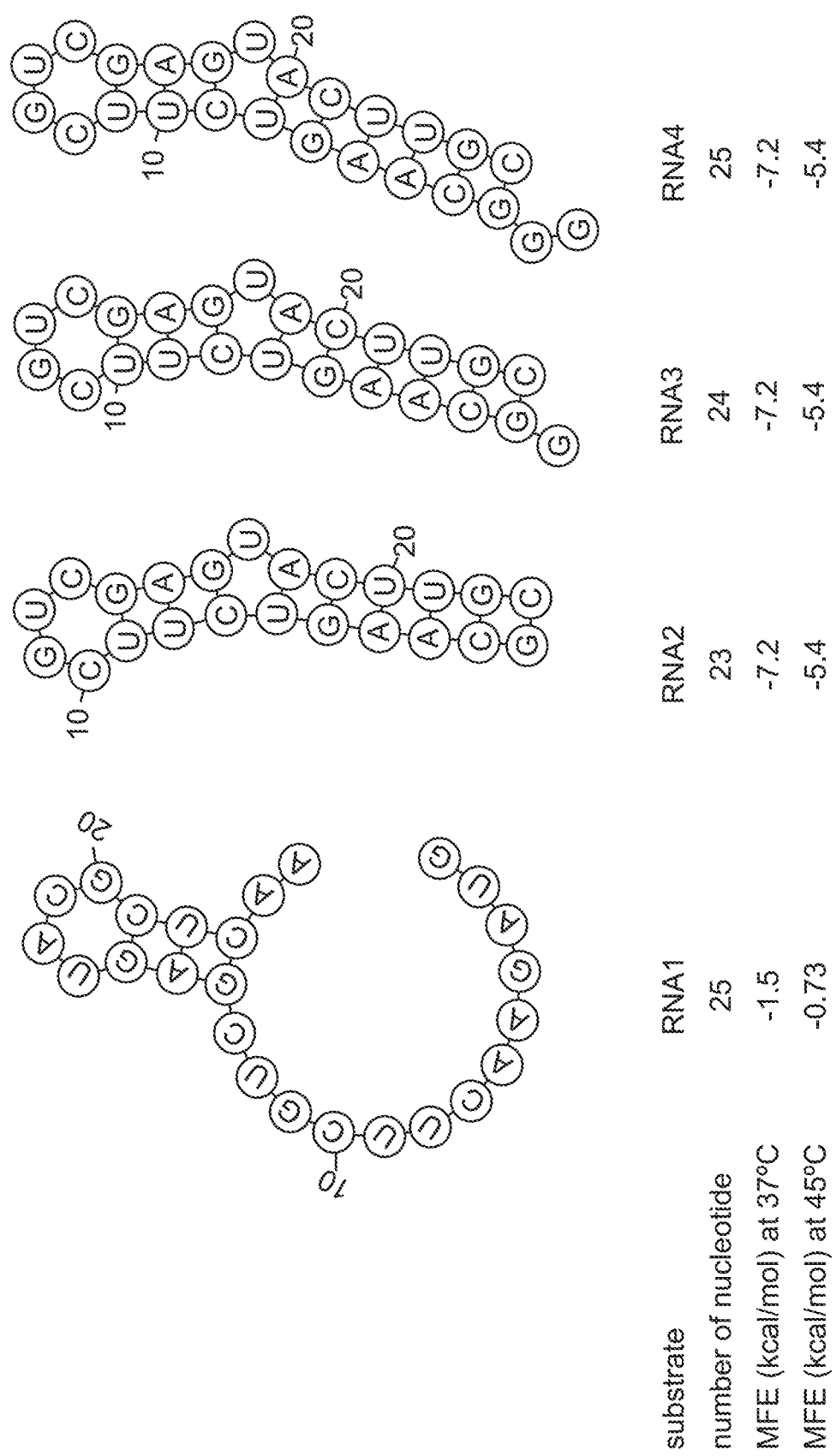
FIG. 1 shows the predicted secondary structure of the model RNA molecules used. RNA1 was designed to have the least secondary structure at the 5' end. RNA2, RNA3 and RNA4 were designed to exhibit the same predicted minimum free energy of unfolding (MFE) while containing a blunt end, one-base or two-base overhang at their 5' ends. The secondary structures and minimum free energy of unfolding at 37° C. and 45° C. were calculated using the RNAFold webserver (Vienna University, Wien, Austria). The modeled RNA molecules have the following sequences: RNA1: SEQ ID NO:13, RNA2: SEQ ID NO:14, RNA3: SEQ ID NO:15, RNA4: SEQ ID NO:16.

Aspects of the present disclosure can be further understood in light of the embodiments, section headings, figures, descriptions and examples, none of which should be construed as limiting the entire scope of the present disclosure in any way. Accordingly, the claims set forth below should be construed in view of the full breadth and spirit of the disclosure.

Each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible. Disclosed reaction conditions may be varied, including, but not limited to, reaction temperature, reaction duration, reaction components (e.g., enzymes, substrates) and/or reactant concentrations.

Unless otherwise defined, all technical and scientific terms used herein have the same meaning as commonly understood by one of ordinary skill in the art to which this disclosure belongs. Still, certain terms are defined herein with respect to embodiments of the disclosure and for the sake of clarity and ease of reference.

Sources of commonly understood terms and symbols may include: standard treatises and texts such as Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Singleton, et al., Dictionary of Microbiology and Molecular biology, 2d ed., John Wiley and Sons, New York (1994), and Hale & Markham, the Harper Collins Dictionary of Biology, Harper Perennial, N.Y. (1991) and the like.

As used herein and in the appended claims, the singular forms "a" and "an" include plural referents unless the context clearly dictates otherwise. For example, the term "a protein" refers to one or more proteins, i.e., a single protein and multiple proteins. It is further noted that the claims can be drafted to exclude any optional element. As such, this statement is intended to serve as antecedent basis for use of such exclusive terminology as "solely," "only" and the like in connection with the recitation of claim elements or use of a "negative" limitation.

Numeric ranges are inclusive of the numbers defining the range. All numbers should be understood to encompass the midpoint of the integer above and below the integer i.e., the number 2 encompasses 1.5-2.5. The number 2.5 encompasses 2.45-2.55 etc. When sample numerical values are provided, each alone may represent an intermediate value in a range of values and together may represent the extremes of a range unless specified. e.g.

In the context of the present disclosure, "buffering agent", refers to an agent that allows a solution to resist changes in pH when acid or alkali is added to the solution. Examples of suitable non-naturally occurring buffering agents that may be used in the compositions, kits, and methods of the invention include, for example, Tris, HEPES, TAPS, MOPS, tricine, or MES.

In the context of the present disclosure, "capping" refers to the enzymatic addition of a Nppp-moiety onto the 5' end of an RNA, where N a nucleotide such as is G or a modified G. A modified G may have a methyl group at the N7 position of the guanine ring, or an added label at the 2 or 3 position of the ribose, and, in some embodiments, the label may be an oligonucleotide, a detectable label such as a fluorophore, or a capture moiety such as biotin or desthiobiotin, where the label may be optionally linked to the ribose of the nucleotide by a linker, for example. See, e.g., WO 2015/085142. A cap may have a Cap-0 structure, a Cap-1 structure or a cap 2 structure (as reviewed in Ramanathan, Nucleic Acids Res. 2016 44: 7511-7526), depending on which enzymes and/or whether SAM is present in the capping reaction.

In the context of the present disclosure, "DNA template" refers to a double stranded DNA molecule that is transcribed in an in vitro transcription reaction. DNA templates have a promoter (e.g., a T7, T3 or SP6 promoter) recognized by the RNA polymerase upstream of the region that is transcribed.

In the context of the present disclosure, "fusion" refers to two or more polypeptides, subunits, or proteins covalently joined to one another (e.g., by a peptide bond). For example, a protein fusion may refer to a non-naturally occurring polypeptide comprising a protein of interest covalently joined to a reporter protein. Alternatively, a fusion may comprise a non-naturally occurring combined polypeptide chain comprising two proteins or two protein domains joined directly to each other by a peptide bond or joined through a peptide linker.

In the context of the present disclosure, "in vitro transcription" (IVT) refers to a cell-free reaction in which a double-stranded DNA (dsDNA) template is copied by a DNA-directed RNA polymerase (typically a bacteriophage polymerase) to produce a product that contains RNA molecules copied from the template.

In the context of the present disclosure, "Faustovirus RNA capping enzyme" refers to a single-chain RNA capping enzyme capable of capping RNA (e.g., having detectable TPase, GTase and N7 MTase activity) including, for example, enzymes having at least 90% identity to faustovirus D5b (SEQ ID NO:7), Faustovirus E12 (SEQ ID NO:8), Faustovirus ST1 (SEQ ID NO:9), or Faustovirus LC9 (SEQ ID NO:10). "H3C2 RNA capping enzyme", "H3C2 capping enzyme" or "H3C2" refers to the RNA capping enzyme from faustovirus D5b (SEQ ID NO:7). Unless expressly stated otherwise, Faustovirus RNA capping enzymes may be interchangeable with one another for purposes of illustrations and examples disclosed herein with similar properties, effects, and/or benefits.

In the context of the present disclosure, "H3C2 fusion" refers to a bifunctional enzyme capable of synthesizing an RNA from a template polynucleotide and capable of capping RNA, the fusion comprising an RNA polymerase (e.g., T7 RNA polymerase, T3 RNA polymerase, SP6 RNA polymerase and a Faustovirus RNA capping enzyme arranged on the N-terminal end or the C-terminal end relative to the polymerase. An H3C2 fusion may further comprise a leader and/or a linker (e.g., between the polymerase and the H3C2). An H3C2 fusion may have, for example, an amino acid sequence having at least 80%, at least 85%, at least 90%, at least 93%, at least 96%, at least 97%, at least 98% or at least 99% identity to SEQ ID NO:20. An H3C2:T7 RNA polymerase fusion is an example of an H3C2 fusion.

In the context of the present disclosure, "H3C2 variant" refers to H3C2, H3C2 fusions, and enzymes capable of capping RNA, in each case, comprising an amino acid sequence having at least 80%, at least 85% at least 90%, at least 93%, at least 96%, at least 97%, at least 98% or at least 99% identity to SEQ ID NO:7, 8, 9, 10, 11, and/or 12.

In the context of the present disclosure, "modified nucleotides" (including references to modified NTP, modified ATP, modified GTP, modified CTP, and modified UTP) refers to any noncanonical nucleoside, nucleotide or corresponding phosphorylated versions thereof. Modified nucleotides may include one or more backbone or base modifications. Examples of modified nucleotides include dI, dU, 8-oxo-dG, dX, and THF. Additional examples of modified nucleotides include the modified nucleotides disclosed in U.S. Patent Publication Nos. US20170056528A1, US20160038612A1, US2015/0167017A1, and US20200040026A1. Modified nucleotides may include naturally or non-naturally occurring nucleotides.

In the context of the present disclosure, "non-naturally occurring" refers to a polynucleotide, polypeptide, carbohydrate, lipid, or composition that does not exist in nature. Such a polynucleotide, polypeptide, carbohydrate, lipid, or composition may differ from naturally occurring polynucleotides polypeptides, carbohydrates, lipids, or compositions in one or more respects. For example, a polymer (e.g., a polynucleotide, polypeptide, or carbohydrate) may differ in the kind and arrangement of the component building blocks (e.g., nucleotide sequence, amino acid sequence, or sugar molecules). A polymer may differ from a naturally occurring polymer with respect to the molecule(s) to which it is linked. For example, a "non-naturally occurring" protein may differ from naturally occurring proteins in its secondary, tertiary, or quaternary structure, by having a chemical bond (e.g., a covalent bond including a peptide bond, a phosphate bond, a disulfide bond, an ester bond, and ether bond, and others) to a polypeptide (e.g., a fusion protein), a lipid, a carbohydrate, or any other molecule. Similarly, a "non-naturally occurring" polynucleotide or nucleic acid may contain one or more other modifications (e.g., an added label or other moiety) to the 5'-end, the 3' end, and/or between the 5'- and 3'-ends (e.g., methylation) of the nucleic acid. A "non-naturally occurring" composition may differ from naturally occurring compositions in one or more of the following respects: (a) having components that are not combined in nature, (b) having components in concentrations not found in nature, (c) omitting one or components otherwise found in naturally occurring compositions, (d) having a form not found in nature, e.g., dried, freeze dried, crystalline, aqueous, and (e) having one or more additional components beyond those found in nature (e.g., buffering agents, a detergent, a dye, a solvent or a preservative). All publications, patents, and patent applications mentioned in this specification are herein incorporated by reference to the same extent as if each individual publication, patent, or patent application was specifically and individually indicated to be incorporated by reference.

In the context of the present disclosure, "RNA sample" or "sample" refers to a composition that may or may not comprise a target RNA. For example, an RNA sample may be known to include or suspected of including such target RNA and/or an RNA sample may be a composition to be evaluated for the presence of a target RNA. An RNA sample may comprise a naturally occurring target RNA (e.g., extracted from a cell, tissue, or organism), a target RNA produced by in vitro transcription, and/or a chemically synthesized RNA.

In the context of the present disclosure, "single-chain RNA capping enzyme" refers to a capping enzyme in which a single polypeptide chain includes the TPase, GTase and N7 MTase activities. Faustovirus, mimivirus and moumouvirus capping enzymes are examples of single-chain RNA capping enzymes. H3C2 fusions are additional examples of single-chain RNA capping enzymes. VCE is a heterodimer and, as such, is not a single-chain RNA capping enzyme.

In the context of the present disclosure, "single uncapped RNA target species" refers to a mixture of target RNA molecules that have essentially the same sequence. Transcripts made by in vitro transcription and RNA oligonucleotides made by solid-phase synthesis are examples single uncapped RNA target species. It is recognized that a certain amount of the RNA products in such a mixture may be truncated. Single uncapped RNA target species may sometimes contain modified nucleotides (e.g., noncanonical nucleotides that are not found in nature). Preparations of RNA from a cell contain a complex mixture of naturally occurring RNA molecules having different sequences; such preparations do not contain only targeted uncapped RNA species but also contain a wide variety of non-target RNAs. In some embodiments, the targeted uncapped RNA species is a single species of RNA.

In the context of the present disclosure, "target RNA" refers to a polyribonucleotide of interest. A polyribonucleotide may be or comprise a therapeutic RNA or precursor thereof (e.g., an uncapped precursor of a capped therapeutic RNA). A target RNA may arise from cellular transcription or in vitro transcription. A target RNA may be present in a mixture, for example, an in vitro transcription reaction mixture, a cell, or a cell lysate. A target RNA may be uncapped. If desired or required, a target RNA may be contacted with a decapping enzyme, for example, as a co-treatment with or pre-treatment before capping.

In the context of the present disclosure, "uncapped" refers to an RNA (a) that does not have a cap and (b) that can be used as a substrate for a capping enzyme. Uncapped RNA typically has a tri- or di-phosphorylated 5' end. RNAs transcribed in vitro have a triphosphate group at the 5' end.

In the context of the present disclosure, "variant" refers to a protein that has an amino acid sequence that is different from a naturally occurring amino acid sequence (i.e., having less than 100% sequence identity to the amino acid sequence of a naturally occurring protein) but that is at least 80%, at least 85%, at least 90%, at least 95%, at least 97%, at least 98% or at least 99% identical to the naturally occurring amino acid sequence.

Provided herein are a variety of in vitro RNA capping methods. Some embodiments of the method are based, in part, on the discovery that VCE of SEQ ID NO:1 is significantly more active at 45° C. as compared to 37° C. (see FIG. 2 and Tables 1 and 2, below), particularly for RNAs that have secondary structure. For example, when used to add a cap to an in vitro transcribed RNA that encodes a protein, the same amount of capped product can be produced at 45° C. using less than a thirtieth ($\frac{1}{30}^{th}$) of the amount of enzyme, as compared to 37° C. (see Table 6). In addition, incubation at the reaction at 45° C. allows the VCE to efficiently add a cap to uncapped RNA oligonucleotides that have secondary structure at the 5' end (e.g., a 5' end that is predicted to base pair with another sequence in the molecule to produce a blunt end or a 3' or 5' overhang of 1 or 2 nucleotides, as exemplified in FIG. 1). Such RNAs are very inefficiently capped using the VCE at 37° C. (see FIG. 9). In some embodiments therefore, the method may comprise incubating a reaction mix comprising RNA, VCE or a variant thereof, GTP or modified GTP, SAM and a buffering agent at a temperature in the range of 42° C.-47° C., e.g., 44° C.-46° C. to efficiently add a cap structure to the uncapped RNA target. These embodiments of the method are particularly useful for RNAs having or predicted to have secondary structure, such as RNAs over 200 nt in length transcribed in vitro, and RNA oligonucleotides that have secondary structure at the 5' end.

Other embodiments of the method are based in part on the discovery that the RNA capping enzyme from faustovirus D5b (SEQ ID NO:7, an example of an H3C2 capping enzyme and referenced here by the shorthand "H3C2") is capable of capping RNA significantly more efficiently than the VCE at almost all temperatures tested (see FIG. 2 and Tables 1 and 6, below) and, like the VCE, can be used to efficiently add a cap to an in vitro transcribed RNA at 45° C. For example, the same amount of capped product can be produced at 45° C. using less than a thirtieth ($\frac{1}{30}^{th}$) of the amount of faustovirus D5b (H3C2), as compared to 37° C. (see Table 6). In addition, incubating the reaction at 45° C. allows the faustovirus D5b (H3C2) to efficiently add a cap to uncapped RNA oligonucleotides that have secondary structure at the 5' end. Such RNAs are very inefficiently capped using the faustovirus D5b (H3C2) 37° C. (see FIG. 9). Capping enzymes from other giant viruses of the amoebas, including faustovirus ST1, faustovirus LC9, faustovirus E12, mimivirus, and moumouvirus were also tested and found to be active at higher temperatures. As such, in some embodiments, the method may comprise incubating a reaction mix comprising a sample comprising RNA, a single-chain capping enzyme, GTP or modified GTP and a buffering agent at a temperature in the range of 37° C.-60° C., e.g., 37° C.-42° C., 42° C.-47° C., 47° C.-52° C. or 52° C.-60° C. to efficiently add a cap structure to the uncapped RNA target. in vitro These embodiments of the method are particularly useful for RNAs that have or predicted to have secondary structure such as RNAs over 200 nt in length transcribed in vitro, and RNA oligonucleotides that have secondary structure at the 5' end.

More efficient capping of the RNA substrate may support capping with less enzyme added to a capping reaction, producing more capped RNA (as a percentage of the RNA in the reaction) using the same amount of enzyme, terminating the reaction earlier, and/or capping RNAs that have secondary structure at the 5' end more efficiently.

Disclosed reaction conditions may be varied, including, without limitation, reaction temperature, reaction duration, reaction component concentrations (e.g., SAM, inorganic pyrophosphatase, NTPs, transcript template), and enzymes (e.g., capping enzymes, polymerases, and fusions thereof). For example, an H3C2:T7 RNA polymerase fusion protein may further improve the efficiency of Cap-0 RNA synthesis in terms of fraction of Cap-0 transcripts and transcription output. In addition, inclusion of a cap 2'O methyltransferase, such as Vaccinia cap 2'O methyltransferase, in the reactions can generate Cap-1 transcript at high efficiency. Depending on which enzyme is used and the other components in the reaction mix, disclosed methods may be used to make RNAs that have a Gppp cap, a 7-methylguanylate cap (i.e., a m7Gppp cap, or "cap-0"), or an RNA that has an m7Gppp cap that has addition modifications in the first and/or second nucleotides in the RNA (i.e., "cap-1" and "cap-2"; see Fechter J. Gen. Vir. 2005 86: 1239-49). For example, if there is no SAM in the reaction mix then RNAs that have a Gppp cap may be produced. If the reaction mix comprises SAM in addition to the capping enzyme, then cap-0 RNA may be produced. If the reaction mix comprises other enzymes, e.g., cap 2'OMTase in addition to SAM, then cap-1 and/or cap-2 RNA may be produced. A reaction mix may comprise other components in addition to those explicitly described above.

In some embodiments, uncapped RNA in the reaction mix may be prepared by solid-phase oligonucleotide synthesis chemistry (see, e.g., Li, et al J. Org. Chem. 2012 77: 9889-9892), in which case the RNA in the sample may be may have a length in the range of 10-500 bases, e.g., 20-200 bases). In other embodiments, uncapped RNA in the reaction mix may be prepared in a cell free in vitro transcription (IVT) reaction in which a double-stranded DNA template that contains a promoter for an RNA polymerase (e.g., a T7, T3 or SP6 promoter) upstream of the region that is transcribed is copied by a DNA-directed RNA polymerase (typically a bacteriophage polymerase) to produce a product that contains RNA molecules copied from the template. In either embodiment, the RNA sample that is capped in the present method contains a single species of RNA (either the synthetic oligonucleotide or the transcript). In addition, the reaction mix may be RNase-free and may optionally comprise one or more RNase inhibitors. The RNA in the sample may contain a non-natural sequence of nucleotides and in some embodiments, may contain non-naturally occurring nucleotides. In some embodiments, the in vitro transcription reaction may employ a thermostable variant of the T7, T3 and SP6 RNA polymerase (see, e.g., PCT/US2017/013179 and U.S. application Ser. No. 15/594,090). In these embodiments, the RNAs may be transcribed at a temperature of greater than 44° C. (e.g., a temperature of at least 45° C., at least 50° C., at least 55° C. or at least 60° C., up to about 70° C. or 75° C.) in order to reduce the immunogenicity of the RNA (see, e.g., WO 2018/236617). In some cases, the uncapped RNA may be capped immediately after it is made, e.g., by adding an RNA capping enzyme and GTP/modified GTP, as needed to the in vitro transcription reaction after the reaction has run its course. In some embodiments, the RNA made in an in vitro transcription reaction may purified prior to capping.

In some embodiments, the RNA in the sample may be a therapeutic RNA. In these embodiments, the product of the present method may be used without purification of the capped RNA from the uncapped RNA. In these embodiments, the product of the present reaction may be combined with a pharmaceutical acceptable excipient to produce a formulation, where "pharmaceutical acceptable excipient" is any solvent that is compatible with administration to a living mammalian organism via transdermal, oral, intravenous, or other administration means used in the art. Examples of pharmaceutical acceptable excipients include those described for example in US 2017/0119740. The formulation may be administered in vivo, for example, to a subject, examples of which include a human or any non-human animal (e.g., mouse, rat, rabbit, dog, cat, cattle, swine, sheep, horse or primate). Depending on the subject, the RNA (modified or unmodified) can be introduced into the cell directly by injecting the RNA or indirectly via the surrounding medium. Administration can be performed by standardized methods. The RNA can either be naked or formulated in a suitable form for administration to a subject, e.g., a human. Formulations can include liquid formulations (solutions, suspensions, dispersions), topical formulations (gels, ointments, drops, creams), liposomal formulations (such as those described in: U.S. Pat. No. 9,629,804 B2; US 2012/0251618 A1; WO 2014/152211; US 2016/0038432 A1). The cells into which the RNA product is introduced may be in vitro (i.e., cells that cultured in vitro on a synthetic medium). Accordingly, the RNA product may be transfected into the cells. The cells into which the RNA product is introduced may be in vivo (cells that are part of a mammal). Accordingly, the introducing may be done by administering the RNA product to a subject in vivo. The cells into which the RNA product is introduced may be present ex vivo (cells that are part of a tissue, e.g., a soft tissue that has been removed from a mammal or isolated from the blood of a mammal).

Synthesis of large amounts of uniformly capped mRNA transcripts in a cost-effective and streamlined manner that is scalable to support multi-gram synthesis may be desired or required to manufacture mRNA for therapeutic applications. Current approaches to mRNA manufacturing use costly mRNA cap analogs in in vitro transcription reactions. Alternatively, separate reactions are required to produce 5'-triphosphate RNA by in vitro transcription followed by mRNA capping using enzymes—a more complex process that is harder to scale. A single-step in vitro synthesis of capped RNA using T7 RNA polymerase and a capping enzyme may streamline the manufacturing process. Single-vessel reactions with both enzymes may reduce or remove otherwise prohibitive costs of synthetic mRNA cap analogs and may reduce the complexity of scaling this workflow to support multi-gram (and beyond) synthesis.

Methods

Provided herein are methods for efficiently producing capped RNA. In some embodiments, methods include thermoactive Hi-T7 RNA polymerase and H3C2 RNA capping enzyme and unexpectedly thermoactive Vaccinia mRNA cap 2'O methyltransferase. Surprisingly, reaction temperatures substantially higher than 37° C. enable single reaction capped mRNA synthesis. In some embodiments, RNA transcription and capping activities may be performed in a single reaction at higher temperatures (e.g., 40° C. to 60° C.). For example, RNA polymerases and individual capping enzymes with or without Vaccinia cap 2'O methyltransferase may be used simultaneously in capped RNA synthesis reactions. Combining RNA transcription and capping activities may be achieved, for example, with fusion proteins comprising H3C2, a single-subunit RNA capping enzyme, and T7 RNA polymerase or Hi-T7 RNA polymerase. Methods described herein can achieve high levels of Cap-0 or Cap-1 RNA synthesis.

A capping method, in some embodiments, may comprise contacting an RNA polymerase (e.g., a T7 RNA polymerase, a thermoactive Hi-T7 RNA polymerase and/or an H3C2 fusion), a polynucleotide (e.g., DNA or RNA) encoding a target RNA, a capping enzyme (e.g., VCE, H3C2, an H3C2 fusion), NTPs, a buffering agent, optionally in the presence or absence of SAM. Nucleoside triphosphates (NTPs) may include unmodified ATP, modified ATP (m6ATP, m1ATP), unmodified CTP, modified CTP (e.g. m5CTP), unmodified GTP, modified GTP, unmodified UTP, modified UTP (e.g., pseudouridine triphosphate, m1pseudouridin triphosphate), NTPs containing 2'O methylation, and/or combinations thereof. In some embodiments, a capping method may comprise contacting a capping enzyme (e.g., VCE, H3C2, an H3C2 fusion), a target RNA, and guanosine triphosphate (GTP), and/or modified GTP. A capping method may comprise, in some embodiments, contacting a capping enzyme (e.g., VCE, H3C2, an H3C2 fusion), a target RNA, and guanosine triphosphate (GTP) and/or modified GTP, an O-methyl transferase (e.g., thermoactive Vaccinia mRNA cap 2'O methyltransferase), in the presence or absence of SAM.

Contacting, according to some embodiments, may be performed in a single location (e.g., in a single step), for example, on any surface (e.g., plate or bead) or in any vessel (e.g., tube, flask, vial, column, container, bioreactor or other space). In some embodiments, contacting may comprise contacting some or all the subject elements in any desired order or concurrently. Contacting, in some embodiments, may comprise contacting some or all the subject elements in the presence of a buffering agent. For example, contacting may include contacting, in any order or concurrently, a capping enzyme (e.g., VCE, H3C2, an H3C2 fusion), a target RNA, GTP, and a buffering agent in the presence or absence of SAM. In some embodiments, contacting may further comprise contacting at a temperature of 40° C. to 60° C. (e.g., at 40° C., 42° C., 44° C., 45° C., 46° C., 48° C., 50° C., 52° C., 54° C., 55° C., 56° C., 58° C., or 60° C.) for any desired period of time, for example, 1 minute to 120 minutes (e.g., 1 minute, 5 minutes, 10 minutes, 15 minutes, 20 minutes, 25 minutes, 30 minutes, 45 minutes, 60 minutes, 75 minutes, 90 minutes, 105 minutes, or 120 minutes). In any of the embodiments disclosed herein, contacting may further comprise contacting at a first temperature of 25° C. to 60° C. and cooling or warming to a second temperature of 25° C. to 60° C., different from the first temperature, wherein, optionally, at least one of the first temperature or second temperature is not less than 40° C. A first temperature may be selected to produce, stabilize and/or retain a desired amount of uncapped target RNA and a second temperature may be selected to produce, stabilize and/or retain a desired amount capped target RNA. Each temperature may be maintained for any desired period of time (e.g., 1 minute to 120 minutes). For example, a first temperature may be 37° C. for a first period of 1 to 30 minutes and a second temperature may be 28° C., 32° C., 37° C., 45° C., or 50° C. for a second period of 1 to 30 minutes. Contacting, in any of the disclosed embodiments, may include placing one item in direct contact with another, placing two items together on a surface or in a vessel in sufficient proximity that they may physically and/or chemically interact with or without further agitation or mixing. Contacting may include the initial act of placing one item in direct contact with or proximity to another and/or maintaining conditions that permit or favor the two items to contact each other.

A method, in some embodiments, may comprise synthesizing RNA (e.g., directed or undirected by a template) in vitro to produce an uncapped target RNA and capping the target RNA (e.g., in single-step reactions). Synthesizing RNA from a template may comprise, for example, contacting an RNA polymerase (e.g., a T7 RNA polymerase, a thermoactive Hi-T7 RNA polymerase and/or an H3C2 fusion) with the template (e.g., an RNA template or a DNA template) and one or more NTPs to produce an uncapped target RNA, a buffering agent, and optionally in the presence or absence of SAM. Nucleoside triphosphates (NTPs) may include unmodified ATP, modified ATP (m6ATP, m1ATP), unmodified CTP, modified CTP (e.g. m5CTP), unmodified GTP, modified GTP, unmodified UTP, modified UTP (e.g., pseudouridine triphosphate, m1pseudouridin triphosphate), NTPs containing 2'O methylation, and/or combinations thereof. Capping a target RNA may comprise, for example, contacting H3C2 (e.g., H3C2 or an H3C2 fusion) with a target RNA and guanosine triphosphate (GTP) and/or a modified GTP to produce a capped target RNA. In some embodiments, a capping method may comprise contacting a target RNA with an H3C2 fusion at a temperature of 25° C. to 60° C., A capping method may comprise, in some embodiments, contacting a target RNA with a decapping enzyme to remove an existing cap and/or assure that it is uncapped.

Capping may comprise, for example, contacting a capping enzyme (e.g., VCE, H3C2, an H3C2 fusion) with a target RNA, an O-methyltransferase (e.g., thermoactive Vaccinia mRNA cap 2'O methyltransferase), SAM, guanosine triphosphate (GTP), modified GTP, and/or a buffering agent. For example, capping may comprise contacting a capping enzyme, a target RNA, GTP (optionally, with or without modified GTP), and optionally a buffering agent. Capping may comprise contacting, in a single vessel (e.g., in a single step), a capping enzyme, a target RNA, GTP (optionally, with or without modified GTP), an O-methyltransferase, SAM, and optionally a buffering agent. Capping may comprise capping a pre-existing target RNA and/or synthesizing and capping a target RNA in a single vessel (e.g., in a single step), for example, by contacting a target RNA template (DNA or RNA) encoding the target RNA, a polymerase (e.g., a T7 RNA polymerase, a thermoactive Hi-T7 RNA polymerase and/or an H3C2 fusion), NTPs (optionally including or excluding one or more modified NTPs), a capping enzyme (e.g., VCE, H3C2, an H3C2 fusion), and/or a buffering agent.

Compositions

A variety of compositions related to the disclosed methods are also provided. In some embodiments, a composition (e.g., a reaction mix) may comprise a target RNA (e.g., in an RNA sample) and/or a DNA template encoding a target RNA. In some embodiments, a composition may comprise a single-chain RNA capping enzyme having TPase, GTase and N7 MTase activities, GTP, SAM and a buffering agent. A composition may have a temperature in the range of 37° C.-60° C., e.g., 37° C.-42° C., 42° C.-47° C., 47° C.-52° C. or 52° C.-60° C. In some embodiments, a composition may be free of RNase activity as a result of RNases being inhibited, inactivated or absent. For example, an RNase-free composition may comprise one or more RNase inhibitors. In some embodiments, a composition may further comprise a DNA template operably linked to a promoter, a bacteriophage polymerase that initiates transcription at the promoter, and NTPs, for transcribing the RNA. In some embodiments, a composition may include a cap 2'OMTase. A single-chain RNA capping enzyme may comprise (a) an amino acid sequence at least 90% identical to SEQ ID NO:2, 3, or 4, or (b) an amino acid sequence at least 90% identical to SEQ ID NO:5 or 6. A composition, according to some embodiments, may comprise an H3C2 fusion comprising, in N-terminal to C-terminal order, (a) Faustovirus RNA capping enzyme (e.g., an H3C2 RNA capping enzyme) and an RNA polymerase or (b) an RNA polymerase and an H3C2 RNA capping enzyme, wherein the H3C2 fusion optionally may further comprise a leader (e.g., operably positioned within the fusion) and/or a linker positioned between the H3C2 and the RNA polymerase. In some embodiments, any or all of the components referenced in this paragraph may be combined or otherwise included in a single container. Components, for example, components in a single container, may be present in dry (e.g., anhydrous and/or lyophilized) form. A container with one or more of the referenced components may also contain an aqueous medium.

Kits

Also provided by this disclosure are kits for practicing the subject method, as described above. In some embodiments, the kit may contain any one or more of the components listed above. For example, a kit may contain a single-chain RNA capping enzyme that has TPase, GTase and N7 MTase activities, wherein the enzyme is in a storage buffering agent and a reaction buffering agent (e.g., which may be a 5× or 10× concentrated reaction buffering agent). In some embodiments, the kit may comprise a bacteriophage polymerase and NTPs, for transcribing the RNA from a DNA template. The kit may additionally comprise SAM and a cap 2'OMTase. As would be apparent from the discussion above, the enzyme may comprise (a) an amino acid sequences that are at least 90% identical to SEQ ID NOS: 2, 3, or 4, or (b) an amino acid sequence that is at least 90% identical to SEQ ID NOS: 5 or 6.

The various components of the kit may be present in separate containers or certain compatible components may be pre-combined into a single container, as desired. In addition to above-mentioned components, the subject kits may further include instructions for using the components of the kit to practice the subject methods, i.e., to instructions for capping an RNA.

EXAMPLES

All reagents are available from New England Biolabs (Ipswich, MA) and/or the indicated supplier.

Figure 2:
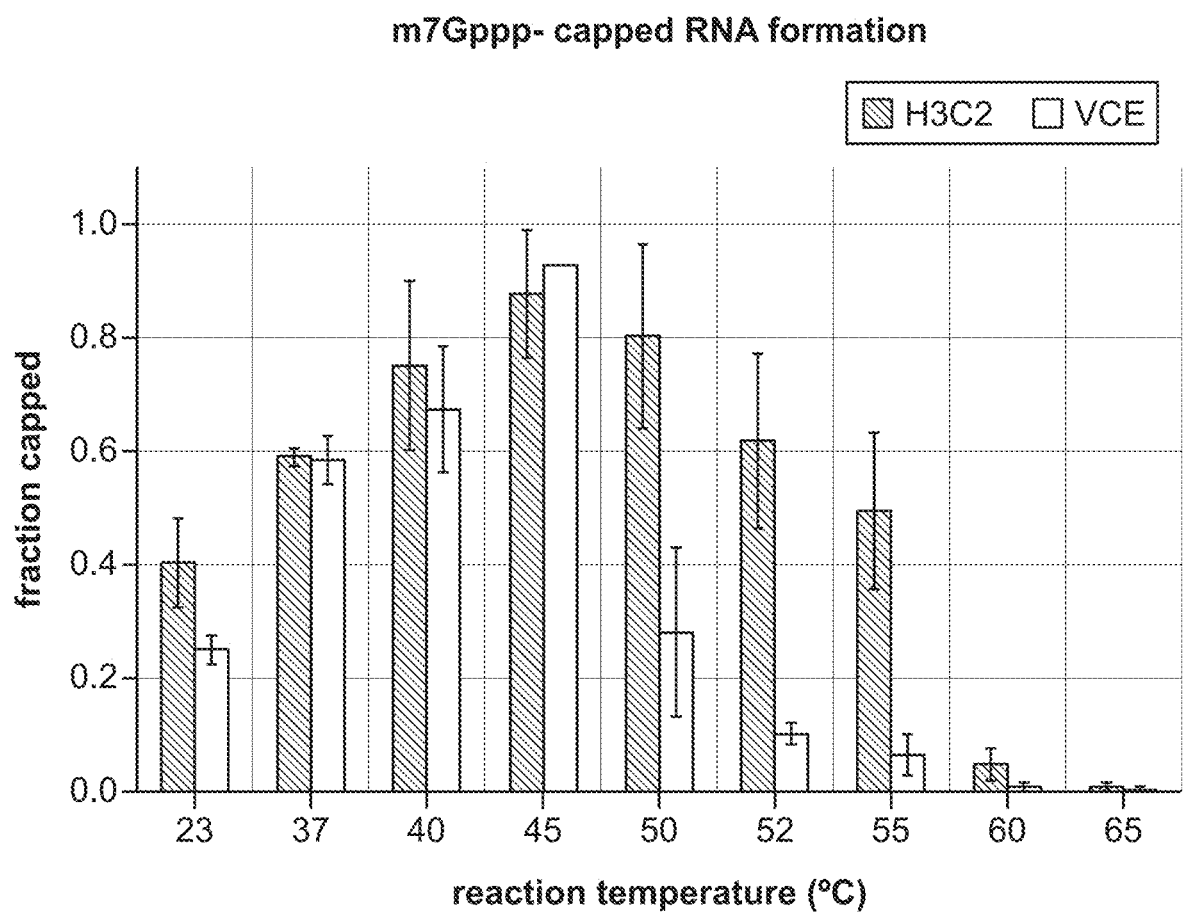
FIG. 2 shows the RNA capping activity of H3C2 and VCE on RNA1 at different reaction temperatures. The amount of m7Gppp-capped RNA is a measure of RNA capping activity of the enzymes. Each bar represents the result of an average of 4 independent experiments, with the error bars indicating the standard deviation. As shown in the figure, both H3C2 and VCE exhibit maximum RNA capping activity at 45° C. While VCE capping activity dropped precipitously at 50° C. and higher, H3C2 retained significant capping activity at 50° C., 52° C. and 55° C.

Example 1: RNA Capping Activity of H3C2 and VCE at High Temperatures 10 nM of purified VCE or H3C2 RNA capping enzyme was incubated with 500 nM RNA1 (FIG. 1) containing a fluorescent group (FAM) at its 3' end in the presence of 0.5 mM GTP and 0.1 mM SAM in 10 µL of 1×RNA capping buffering agent (50 mM Tris-HCl, 5 mM KCl, 1 mM MgCl$_2$, 1 mM DTT, pH 8.0) at temperatures ranged from 23° C. to 65° C. for 30 minutes. The reactions were quenched by adding 1 µL 50 mM EDTA followed by heat-inactivation at 70° C. for 10 minutes. The quenched reactions were analyzed by capillary electrophoresis using an Applied Biosystems 3730xl Genetic Analyzer. The peak area corresponding to the m7Gppp-, unmethylated Gppp-, uncapped pp- and ppp-RNA1 were quantified and used to calculate fraction of m7Gppp- at the end of the 30-minute capping reaction. In FIG. 2, each bar represents an average of 4 independent experiments. Error bars represent the standard deviation of the 4 replicates. It is clear that at low enzyme concentration (10 nM), both H3C2 and VCE exhibited highest capping activity at 45° C. whereas H3C2 retains higher capping activity than VCE at 50° C. and 55° C.

Figure 3A:
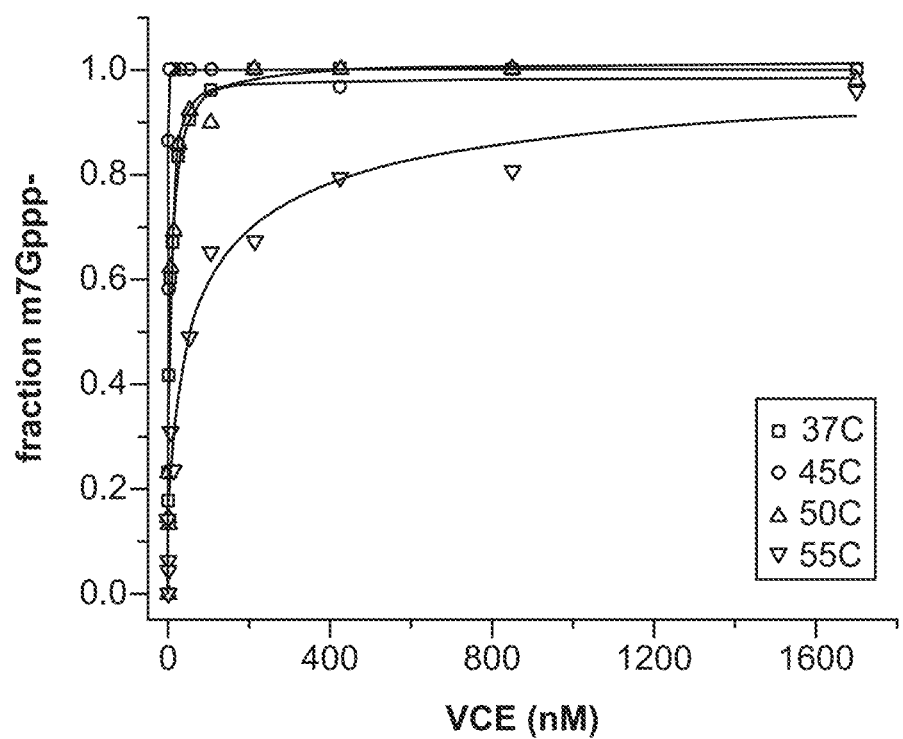
FIGS. 3A-3B shows the RNA capping activity at 37° C., 45° C., 50° C. and 55° C. as a function of capping enzyme concentration.
Figure 3B:
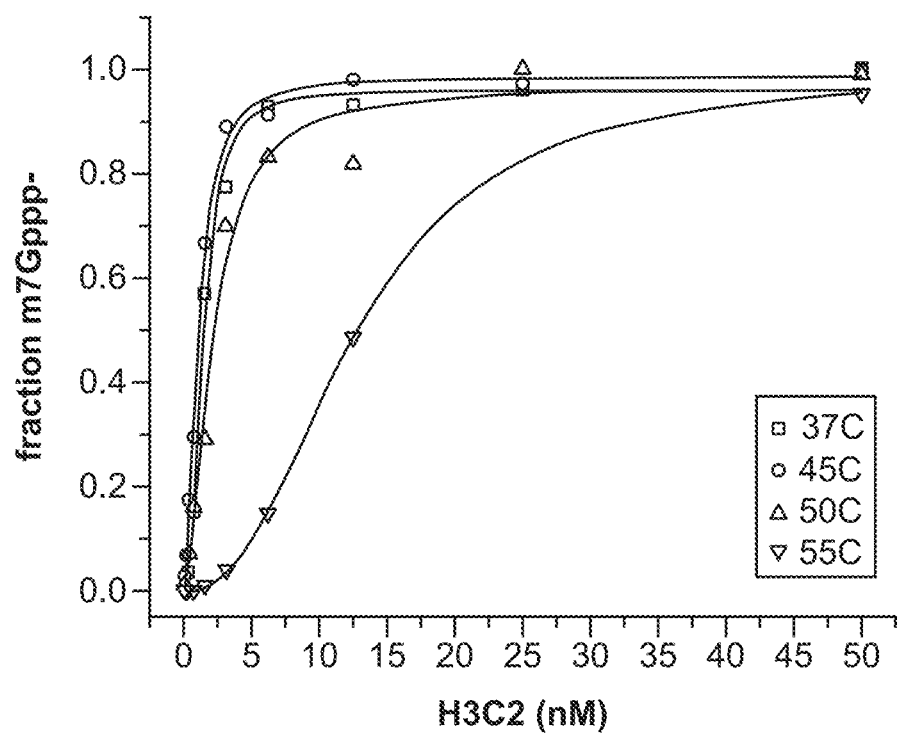
Figure 4A:
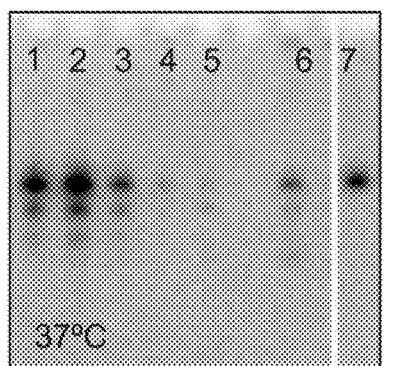
FIGS. 4A-4E RNA capping activity of putative RNA capping enzymes on a 150 nt RNA at various temperatures. Lanes 1 through 6 show capping reactions using products of in vitro translation of AMN83561 (H3C2) (lane 1), AIB52055 (lane 2), SME65026 (lane 3), SMH63629 (lane 4), AAV50651 aa 1-668 (mimivirus capping enzyme N-terminal region) (lane 5), or VP_007354410 (Moumouvirus capping enzyme) (lane 6). In lane 7, purified H3C2 (20 nM) was used. The ribonucleotide sequence of the 150 nt RNA used in these experiments is: GGGAGUCUUCGCCG AGAGGGCCAUCGCCAGUUGCCGCAACCUGUGGG AAUUUCUCUUCCAGUUU AUCCGGAUGCUCAACG-GUGACUUUAAUUCCGGUAUCUUUCUCGAAUUUC-UUACCGACUUCAGCG AGCUCGACAAUGCUCUUC CCUA (SEQ ID NO:17).
Figure 4B:
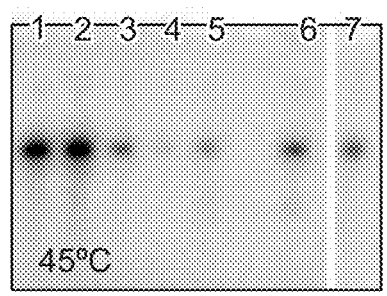
Figure 4C:
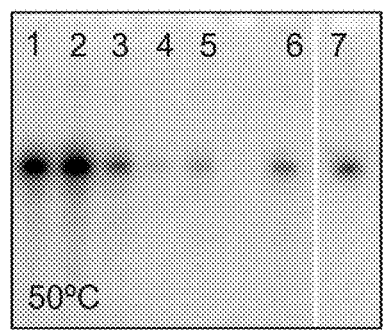
Figure 4D:
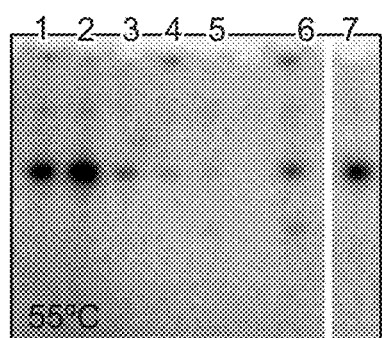
Figure 4E:
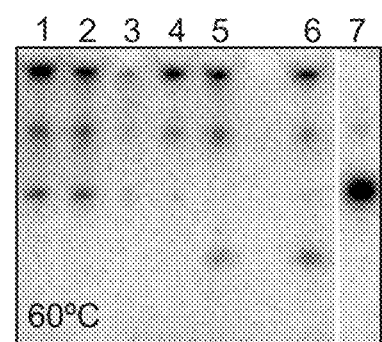

To better quantify the RNA capping activity of VCE and H3C2 at different reaction temperatures, dilutions of the enzymes were incubated under the same reaction conditions at 37° C., 45° C., 50° C. or 55° C., respectively, for 30 minutes. The calculated values of fraction m7Gppp-RNA1 were graphed against enzyme concentration and fitted to a Hill equation derivative to derive the enzyme concentration at which 50% capping was achieved (Cap50). As showed in FIGS. 3A-3B and Table 1, it requires 3.06 nM, 0.94 nM, 4.08 nM and 30.00 nM of VCE to convert 50% of 0.5 uM of ppp-RNA1 to m7Gppp-RNA1 at 37° C., 45° C., 50° C. or 55° C., respectively, in 30 minutes. Furthermore, at 50° C. and below, 400 nM or more VCE caps >90% of 0.5 uM RNA in 30 min. For H3C2, 0.69 nM, 0.67 nM, 2.15 nM or 21.3 nM of enzyme can convert 50% of ppp-RNA1 into m7Gppp-RNA1 at 37° C., 45° C., 50° C. or 55° C., respectively, in 30 minutes. In addition, 50 nM of H3C2 effectively caps >90% of ppp-RNA1 at up to 55° C. in 30 minutes.

2× Master Mix (New England Biolabs, Ipswich, MA) according to manufacturer's recommendations. The amplified T7 expression cassettes were purified using the Monarch® PCR & DNA cleanup kit (New England Biolabs, Ipswich, MA) according to manufacturer's instructions. The purified T7 express cassettes were subjected to in vitro transcription/translation using PURExpress® in vitro Protein Synthesis Kit (New England Biolabs, Ipswich, MA) according to manufacturer's instructions. The PURExpress reaction products, containing the gene products with the indicated Genbank accession numbers (FIGS. 4A-4E), were used in RNA capping assays. Briefly, 50 μL RNA capping reactions made up of 2 μL of PURExpress product, 0.4 μM of a 150 nt in vitro transcript RNA, 4 μM GTP, 0.1 mM SAM, and a trace amount of $^{32}P$-α-GTP in 1×RNA capping buffering agent (50 mM Tris-HCl, 5 mM KCl, 1 mM $MgCl_2$, 1 mM DTT, pH 8.0) were assembled on ice. The reactions were divided into 5 equal parts, each of which were incubated at the indicated temperatures for 30 minutes. The reactions were stopped by adding 10 μL of 2×RNA Loading Dye (New England Biolabs, Ipswich, MA) to the reactions and analyzed by denaturing polyacrylamide electrophoresis and autoradiography. Capping activity is indicated by radiographic signal that migrates at the position of the substrate RNA as indicated. As shown in FIGS. 4A-4E, putative RNA capping enzymes from faustovirus ST1 (Genbank accession SME65026; lanes 3) and faustovirus LC9 (SMH63629;

TABLE 1

RNA capping activity of VCE and H3C2 at various temperatures expressed in Cap50 values in nM (A) or milli-unit per μl of reaction (B).

A

| Reaction temperature | Cap50 (nM) | | | | Fold improvement |
| --- | --- | --- | --- | --- | --- |
| | 37° C. | 45° C. | 50° C. | 55° C. | 45° C. vs 37° C. |
| VCE | 3.06 | 0.94 | 4.08 | 30.00 | 3.24 |
| H3C2 | 0.69 | 0.67 | 2.15 | 21.30 | 1.03 |
| Fold improvement H3C2 vs VCE | 4.46 | 1.42 | 1.90 | 1.41 | |

B

| Reaction temperature | Cap50 (mU/μL) | | | | Fold improvement |
| --- | --- | --- | --- | --- | --- |
| | 37° C. | 45° C. | 50° C. | 55° C. | 45° C. vs 37° C. |
| VCE | 15.30 | 4.72 | 20.40 | 149.98 | 3.24 |
| H3C2 | 3.43 | 0.67 | 10.75 | 1.03 | 1.03 |
| Fold improvement H3C2 vs VCE | 4.46 | 1.42 | 1.90 | 1.41 | |

Example 2: Identification and Testing of H3C2 Orthologs

Purified RNA capping enzyme H3C2 from faustovirus D5b (Genbank® accession AMN83561) was active up to 60° C. under in vitro conditions. By sequence homology, several putative orthologs in other faustovirus strains were identified. It was found that the gene product of the putative RNA capping enzymes from other faustovirus strains and related giant virus *Acanthanomeba polyphaga* mimivirus and *Acanthanomeba polyphaga* moumouvirus were active in RNA capping up to 55-60° C. The ORF of the identified orthologous genes were synthesized and inserted into a T7 expression vector such that the expression of the target genes was under the control of T7 promoter. The T7 expression cassettes were amplified by PCR using Q5® High Fidelity lanes 4), the N-terminal fraction of mimivirus capping enzyme (aa 1-668 of Genbank accession AAV50651; Benarroch et al, 2008; lanes 5) and moumouvirus capping enzyme (Genbank accession YP 007354410; lanes 6) cap the 150 mer RNA at temperatures up to 55° C., whereas RNA capping enzyme from Faustovirus D5b (Genbank accession AMN83561; H3C2; lanes 1), Faustovirus E12 (Genbank accession AIB52055; lanes 2) and purified H3C2 (lanes 7) cap the 150 mer RNA at temperatures up to 60° C.

Example 3: Sequence Analysis

Sequence alignment analysis revealed that three 60 aa- or 111 aa-long regions exhibit 90% or higher amino acid sequence identity among the four Faustovirus RNA capping enzymes that are active up to 55° C. (FIG. 5). Conserved region Fausto_CR_01 spans 60 aa within the TPase domain of H3C2. Fausto_CR_03 spans 111 aa at the N-terminal of the guanosine N7 methyltransferase domain. Fausto_CR_05 spans 60 aa at the C-terminal side of the guanosine N7 methyltransferase domain of H3C2. The amino acid sequence of Fausto_CR_01 (which corresponds to amino acids 43-102 of the H3C2 sequence) is FDKLKPDGEITTTMRVSNADGMAREITFGGGVKTGEMFVKKQNIC VFDVVDIFSYKVAVS (SEQ ID NO:2). The amino acid sequence of Fausto_CR_03 (which corresponds to amino acids 537-647 of the H3C2 sequence) is GFYGNNYKI-ASDIYLNYI DVFNFDDLWKYNPGYFEKNKSDIYIA PNKYRRYLIKSLFNKYIKNAKWVID AAAGRGADLH-LYKAECVENLLAIDIDPTAISELIRRRNEITG (SEQ ID NO:3). The amino acid sequence of Fausto_CR_05 (which corresponds to amino acids 778-873 of the H3C2 sequence) is KYSIKRLYDSDKLTKTGQKIAVLLPMSG EMKEEP-LCNIKNIISMARKMGLDLVESANFSV (SEQ ID NO:4).

The following tables summarize the sequence identities between the amino acid sequences of Faustovirus capping enzymes.

TABLE 2

|  | AMN83561 Faustovirus D5b | AIB52055 Faustovirus E12 | SME65026 Faustovirus ST1 | SMH63629 Faustovirus LC9_partial |
|---|---|---|---|---|
| AMN83561 Faustovirus D5b | 100% | 71% | 71% | 77% |
| AIB52055 Faustovirus E12 | 71% | 100% | 97% | 70% |
| SME65026 Faustovirus ST1 | 71% | 97% | 100% | 69% |
| SMH63629 Faustovirus LC9_partial | 77% | 70% | 69% | 100% |

TABLE 3

|  | AMN83561 Faustovirus D5b | AIB52055 Faustovirus E12 | SME65026 Faustovirus ST1 | SMH63629 Faustovirus LC9_partial |
|---|---|---|---|---|
| Fausto_CR_01 | 92% | 98% | 98% | 92% |
| Fausto_CR_03 | 90% | 99% | 99% | 90% |
| Fausto_CR_05 | 93% | 97% | 97% | 92% |

FIG. 6 shows an alignment of the various Faustovirus RNA capping enzyme sequences, showing the conserved domains as well as the sequences of the TPase, GTase and MTase regions.

Figure 7:
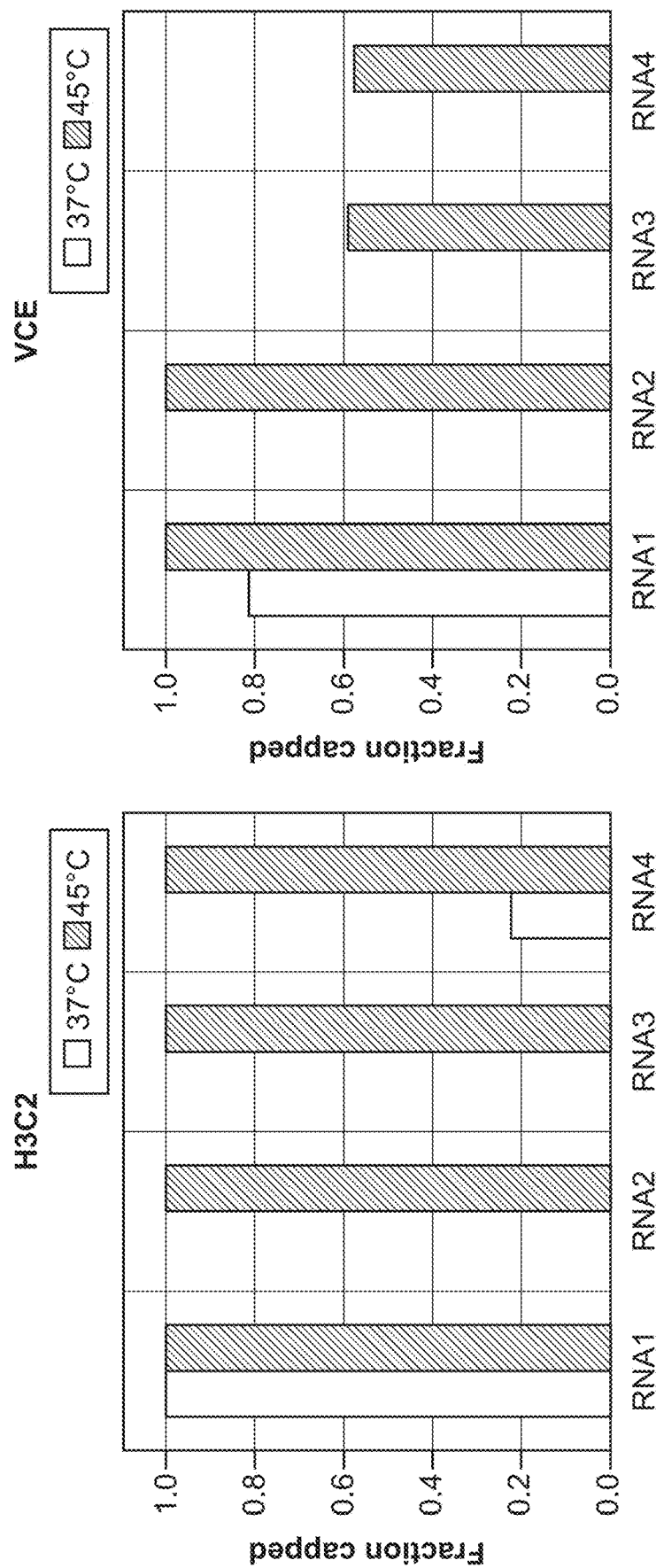
FIG. 7 shows that RNA capping reactions performed at 45° C. facilitate efficient capping of hairpin RNAs. At 37° C. (white bars), both H3C2 and VCE efficiently capped RNA1, which has the least 5' secondary structure (see FIG. 1). RNA2, RNA3 and RNA4, which have stable 5' secondary structures at 37° C. (see FIG. 1), were either not capped or capped to a low extent at 37° C. (white bars). At 45° C. (grey bars), however, H3C2 capped all four RNAs efficiently. VCE efficiently capped RNA1 and RNA2 and partially capped RNA3 and RNA4 at 45° C. (grey bars).

Sequence alignment analysis also revealed that two 67 aa- or 111 aa-long regions exhibit 90% or higher sequence identity between *Acanthanomeba polyphaga* mimivirus and *Acanthanomeba polyphaga* moumouvirus RNA capping enzymes that are active up to 55° C. (FIG. 7). Conserved region moumou_CR_03 (which corresponds to amino acids 576-642 of the moumouvirus sequence) spans 67 aa between the GTase and guanosine N7 methyltransferase domains. Moumou_CR_04 (which corresponds to amino acids 672-782 of the moumouvirus sequence) spans 111 aa at the N-terminal of the guanosine N7 methyltransferase domain. The amino acid sequence of moumou_CR_03 is IND NTVVEFIFDNFKIDMDDPYKWIP IRTRYDKTESVQK YHKKYGNNL HIANRIWKTITNPITEDII (SEQ ID NO:5). The amino acid sequence of moumou_CR_04 is YYQKNTSNAAGMRAFNNFIKSNMITTYCKDGDKVL-DIGCGRGGDLIKFIHAGIEEYV GIDIDNNGLYVINDSA FNRYKNLKKTIKNIPPMTFINADARGLFNLEAQEKILP (SEQ ID NO:6).

The following tables summarize the sequence identities between the amino acid sequences of the mimivirus and moumouvirus RNA capping enzymes.

TABLE 4

|  | AAV50651.1 mimivirus | YP_007354410 Moumouvirus |
|---|---|---|
| AAV50651.1 mimivirus | 100% | 61% |
| YP_007354410 Moumouvirus | 61% | 100% |

TABLE 5

|  | AAV50651.1 mimivirus | YP_007354410 Moumouvirus |
|---|---|---|
| Moumou_CR_03 | 91% | 90% |
| Moumou_CR_04 | 91% | 92% |

Figure 8:
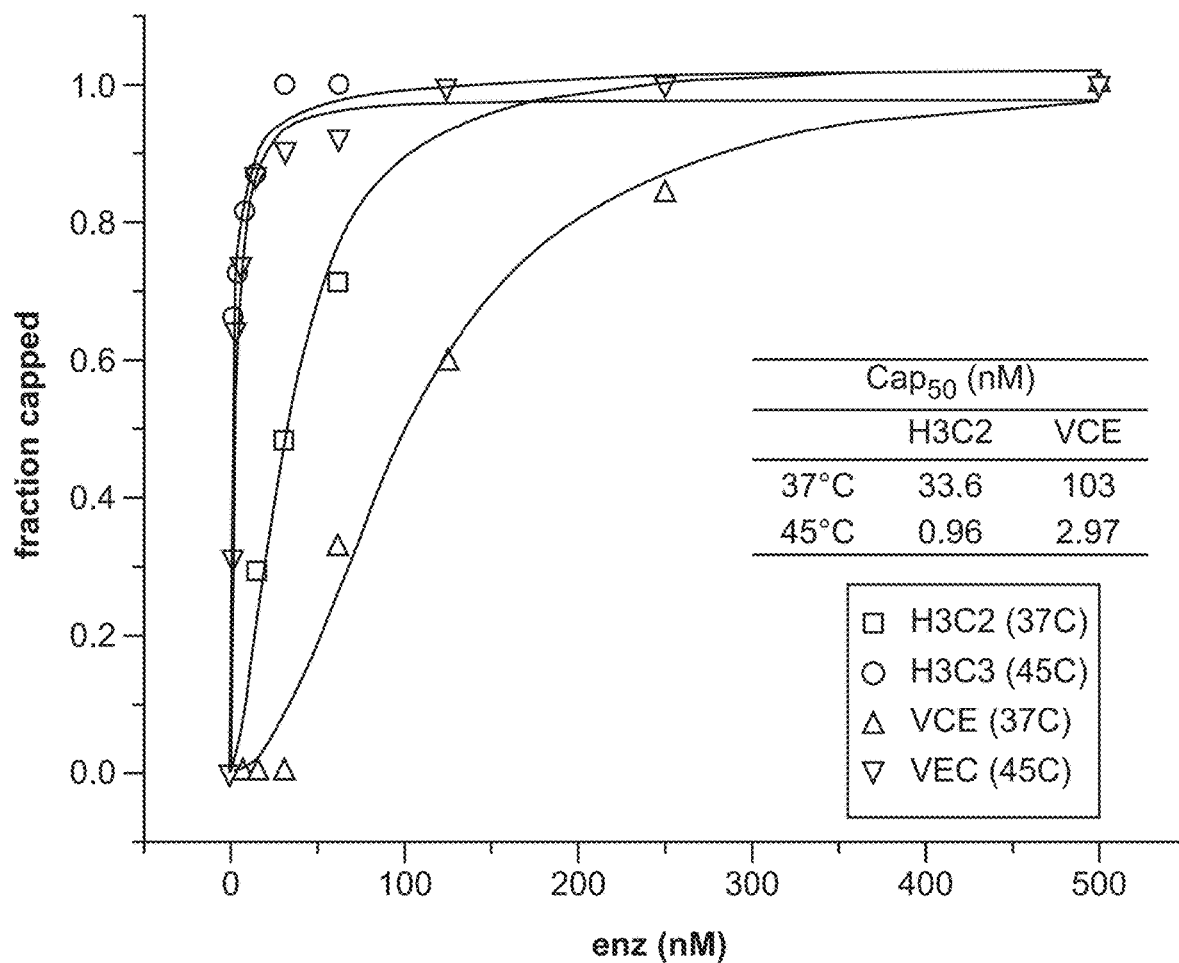
FIG. 8 shows that RNA capping reactions performed at 45° C. facilitate efficient capping of long RNA. Increasing concentrations of H3C2 or VCE were incubated with 400 nM of fluc RNA (1.7 kb) in the presence of 0.5 mM GTP and 0.1 mM SAM in 10 μL of 1×RNA capping buffering agent (50 mM Tris-HCl, 5 mM KCl, 1 mM MgCl$_2$, 1 mM DTT, pH 8) at 37° C. or 45° C. for 30 minutes. The first 24 nt of fluc RNA was then cleaved off by oligo-guided RNase H cleavage. The extent of capping in the cleaved 24 nt fragments was analyzed by electrophoresis over 15% urea polyacrylamide gels. The band intensity was quantified and used to calculate the fraction capped under each condition. The calculated values were graphed against enzyme concentration and fitted to a modified Hill equation to derive the enzyme concentration at which 50% capping was achieved (Cap$_{50}$). For H3C2, the Cap$_{50}$ values were 33.6 nM and 0.96 nM at 37° C. or 45° C., respectively. For VCE, the Cap$_{50}$ values were 103 nM and 2.97 nM at 37° C. or 45° C., respectively. For both H3C2 and VCE, reacting at 45° C. substantially decreased the quantity of enzyme needed to cap 50% of the substrate RNA than at 37° C.

FIG. 8 shows an alignment of the mimivirus and moumou virus sequences, showing the conserved domains as well as the sequences of the TPase, GTase and MTase regions.

Figure 9:
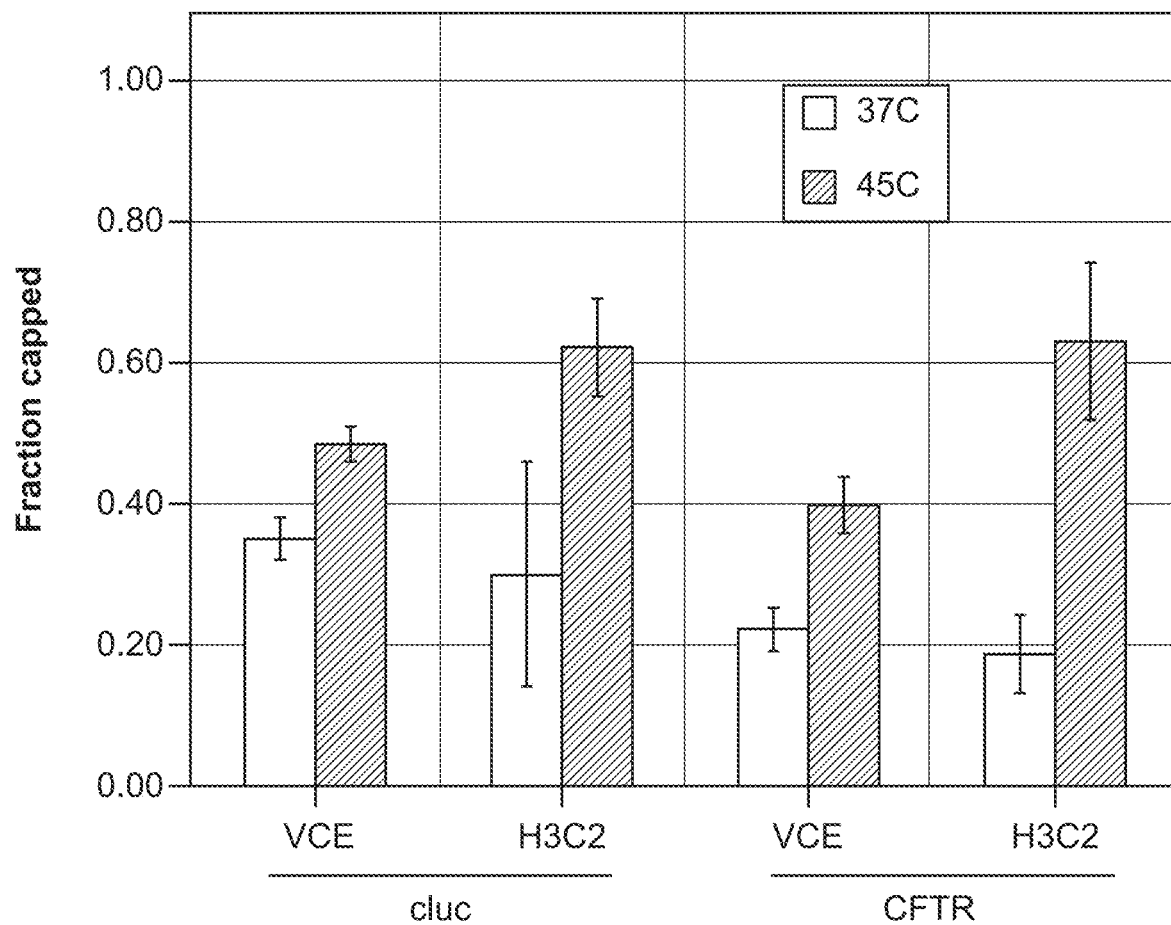
FIG. 9 shows that RNA capping reactions performed at 45° C. facilitate more efficient capping of long RNA other than fluc RNA than at 37° C. 100 nM of H3C2 or VCE was incubated with 500 nM of cluc RNA (1.8 kb) or CFTR RNA (4.0 kb) in the presence of 0.5 mM GTP and 0.1 mM SAM in 10 μL of 1×RNA capping buffering agent (50 mM Tris-HCl, 5 mM KCl, 1 mM MgCl$_2$, 1 mM DTT, pH 8) at 37° C. or 45° C. for 30 min. Defined 5' fragments were cleaved by using Thermostable RNase H (New England Biolabs, Ipswich, MA) and purified using a combination of AMPure® XP Beads (Beckman Coulter, Indianapolis, IN) and streptavidin Dynabeads® (Thermo Fisher Scientific, Waltham, MA). Intact mass analysis of the purified 5' fragments were carried out by Novatia LLC (Newtown, PA) using a high-resolution LC/MS workflow. The fraction of capped RNA was calculated using the mass intensity of capped and uncapped species.

Example 4: RNA Capping Reactions at 45° C. Enhance Capping Efficiency on Short Model Hairpin RNAs The short RNAs illustrated in FIG. 1 were designed as described here to evaluate capping efficiency. A control RNA (RNA1) was designed to have a shorter hairpin structure and an unstructured 5' end with a MFE of −1.5 kcal/mol at 37° C. or −0.73 kcal/mol at 45° C. (FIG. 1). RNA2, RNA3 and RNA4 were designed to form a stable hairpin structure with a theoretical minimum free energy of unfolding (MFE) of −7.2 kcal/mol at 37° C. or −5.4 kcal/mol at 45° C. (RNAFold server rna.tbi.univie.ac.at). RNA2, RNA3 and RNA4 were further designed to have a blunt end, a one-base or a two-base overhang at their 5' end of the respective minimum free energy structure (FIG. 1). The RNAs were produced by in vitro transcription using T7 RNA polymerase. For capping reactions, 50 nM of H3C2 or VCE was incubated with 500 nM of RNA substrates in the presence of 0.5 mM GTP and 0.1 mM SAM in 10 μL of 1×RNA capping buffering agent (50 mM Tris-HCl, 5 mM KCl, 1 mM MgCl$_2$, 1 mM DTT, pH 8.0) at 37° C. or 45° C. for 30 min. At 37° C., H3C2 capped 100% of RNA1, which is predicted to have an unstructured 5' end, and 22% of RNA4, which is predicted to have a two-base overhang structure at the 5' end (FIG. 9). H3C2 was unable to cap RNA2 and RNA3 under these conditions. At 45° C., H3C2 capped 100% of all four RNA substrates. VCE was only able to cap 80% of RNA1 at 37° C. At 45° C., VCE capped 100% of RNA1 and RNA2 and approximately 60% of RNA3 and RNA4.

Figure 10:
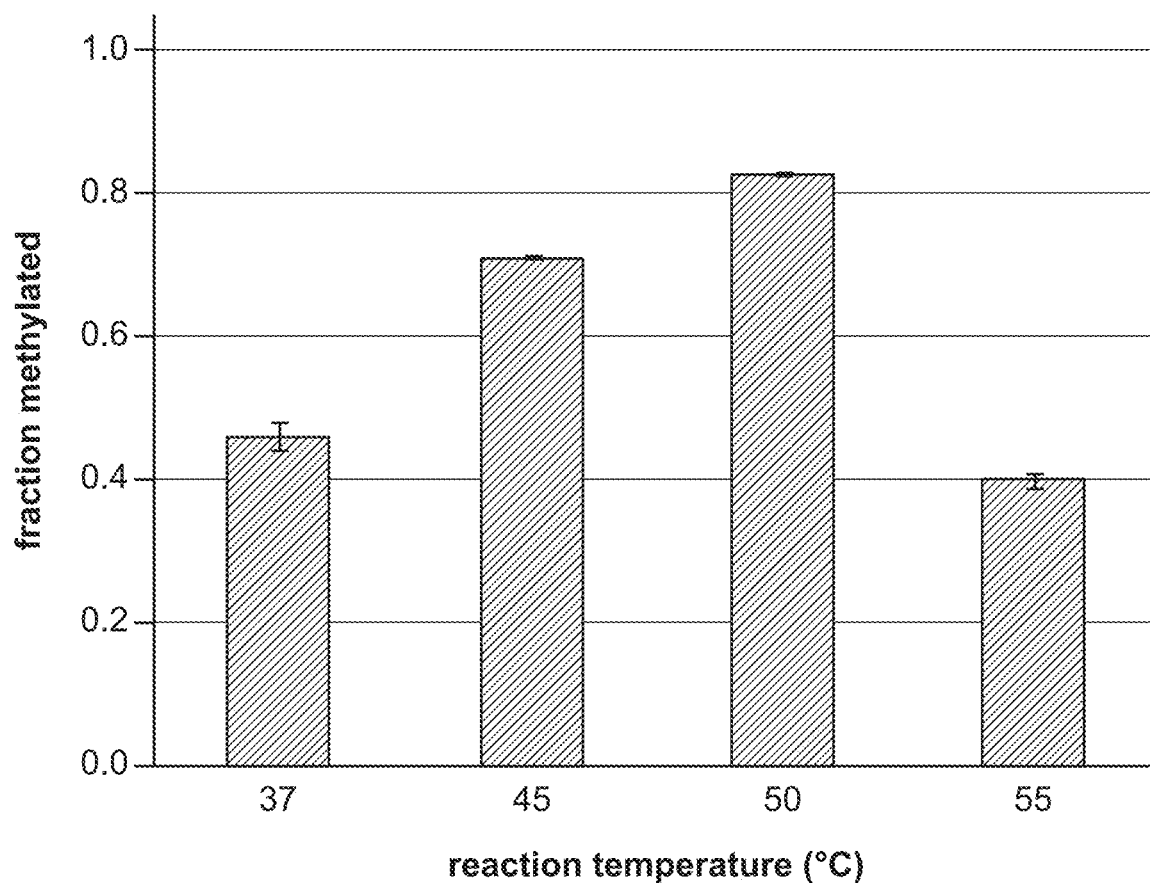
FIG. 10 shows that high reaction temperatures enhance enzymatic activity of Vaccinia virus RNA cap 2'O methyltransferase (MTase). 5 μM of chemically synthesized Cap-0 25-nt RNA (m7Gppp25mer) was allowed to react with 200 μM of SAM in the presence of 100 U of VacciniaVaccinia cap 2'O MTase (New England Biolabs, Ipswich MA) in 20 μL of 1×RNA capping buffering agent at the designated temperature for 30 minutes. The reactions were stopped by heating at 70° C. for 10 minutes. The RNA was purified from the reaction components, digested into nucleosides and cap structures and analyzed by UPLC. More Cap-1 RNA can be generated by carrying out the reaction at 45° C. and 50° C. than at 37° C.

Example 5: RNA Capping Reactions at 45° C. Enhance Capping Efficiency on Long RNAs A 1766 nt RNA containing the firefly luciferase gene (flucfluc) was produced by in vitro transcription using T7 RNA polymerase. 400 nM of fluc RNA was incubated with the indicated concentrations of H3C2 or VCE in the presence of 0.5 mM GTP and 0.1 mM SAM in 10 μL of 1×RNA capping buffering agent (50 mM Tris-HCl, 5 mM KCl, 1 mM MgCl$_2$, 1 mM DTT, pH 8) at 37° C. or 45° C. for 30 minutes. A final concentration of 2.5 μM of targeting oligo (TO) designed to direct RNase H to cleave out a 5' fragment of 25 nt was then added to each capping reaction, which was then heated at 80° C. for 30 s to inactivate the capping enzymes and then cooled slowly to room temperature. Thermostable RNase H (New England Biolabs, Ipswich, MA) was added to each reaction at a final concentration of 0.5 U/4, followed by incubation at 37° C. for 1 hour. The RNase H reactions were then analyzed by electrophoresis through 15% urea polyacrylamide gels. The gels were stained using SYBR® Gold (Thermo Fisher Scientific, Waltham, MA) (according to manufacturer's instructions, and then scanned using an Amersham® Typhoon® RGB (GE Healthcare, Marlborough, MA) scanner using the Cy2 channel. The intensity of the capped and uncapped bands was normalized to that of the TO of the same lane. The normalized values were used to calculate the fraction of RNA capped under each condition. The calculated values were graphed against enzyme concentration and fitted to a Hill equation derivative to derive the enzyme concentration at which 50% capping was achieved (Cap50). For H3C2, the Cap50 values were 33.6 nM and 0.96 nM at 37° C. or 45° C., respectively. For VCE, the Cap50 values were 103 nM and 2.97 nM at 37° C. or 45° C., respectively (FIG. 10 and Table 6 below). For both enzymes, substantially less enzyme was needed to achieve 50% capping when capping reactions were carried out at 45° C.

TABLE 6

RNA capping activity of VCE and H3C2 on 1.7 kb fluc in vitro transcript at 37° C. and 45° C. expressed in Cap50 values.

| Reaction temperature | Cap50 (nM) | | Fold improvement |
|---|---|---|---|
| | 37° C. | 45° C. | 45° C. vs 37° C. |
| H3C2 | 33.60 | 0.96 | 35.00 |
| VCE | 103.14 | 2.97 | 34.73 |
| Fold improvement H3C2 vs VCE | 3.07 | 3.09 | |

The activity of these enzymes can be expressed in milli-unit per μL of reaction, as shown below:

| Reaction temperature | Cap50 (mU/μL) | | Fold improvement |
|---|---|---|---|
| | 37° C. | 45° C. | 45° C. vs 37° C. |
| H3C2 | 168.00 | 4.80 | 35.00 |
| VCE | 515.70 | 14.85 | 34.73 |
| Fold improvement H3C2 vs VCE | 3.07 | 3.09 | |

To show that the temperature-enhanced capping efficiency can be achieved on other long RNA molecules, the capping efficiency of H3C2 and VCE were studied using in vitro transcripts of cypridina luciferase (cluc; 1823 nt) and cystic fibrosis transmembrane receptor (CFTR; 4712 nt) by a mass spectrometry readout. Briefly, 0.5 μM of cluc or CFTR in vitro transcripts were incubated with 100 nM of H3C2 or VCE in the presence of 0.1 mM SAM and 0.5 mM GTP in a reaction volume of 100 μL at 37° C. or 45° C. for 30 minutes. The reactions were stopped by heating at 80° C. for 30 seconds in the presence of 2.5 μM of targeting oligo composed of 5' deoxynucleotides and 3' ribonucleotides and a TEG-desthiobiotin group. The reactions were allowed to cool down to 25° C. at a rate of 0.1° C./s. The reactions were then subjected to RNase H cleavage by incubation with thermostable RNase H (New England Biolabs, Ipswich, MA) at a final concentration of 0.5 U/μL at 37° C. for 1 hour. The 5' fragments of the RNase H cleavage reactions were then purified using size selection using AMPure® XP Beads and target selection using streptavidin magnetic beads. Briefly, 100 μL of RNase H cleavage reactions were added to 200 μL of AMPure® XP Beads and incubated at room temperature for 5 minutes. The beads were then subjected to a magnetic field, and the clarified supernatant was retrieved and added to pre-cleared AMPure® XP beads derived from 200 μL of beads suspension. After incubating at room temperature for 5 min, the beads were subjected to a magnetic field. The clarified supernatant was added to pre-cleared beads derived from 200 μL of Dynabeads® MyOne Streptavidin C1. After washing 4 times with 200 μL of wash buffering agent (5 mM Tris, pH 7.5, 0.5 mM EDTA, 1 M NaCl), the bound RNA was eluted by incubating the clarified beads with 50 μL of biotin elution buffering agent (1 mM biotin, 5 mM Tris, pH 7.5, 0.1 M NaCl, 0.1 M NaCl) at 37° C. for 1 hour. The eluted RNA was then analyzed by LC/MS to determine the relative quantity of the target masses, performed by external contractor Novatia LLC. The extent of RNA capping was assessed by the ratio of the mass intensity of the capped and uncapped RNA species.

Figure 11:
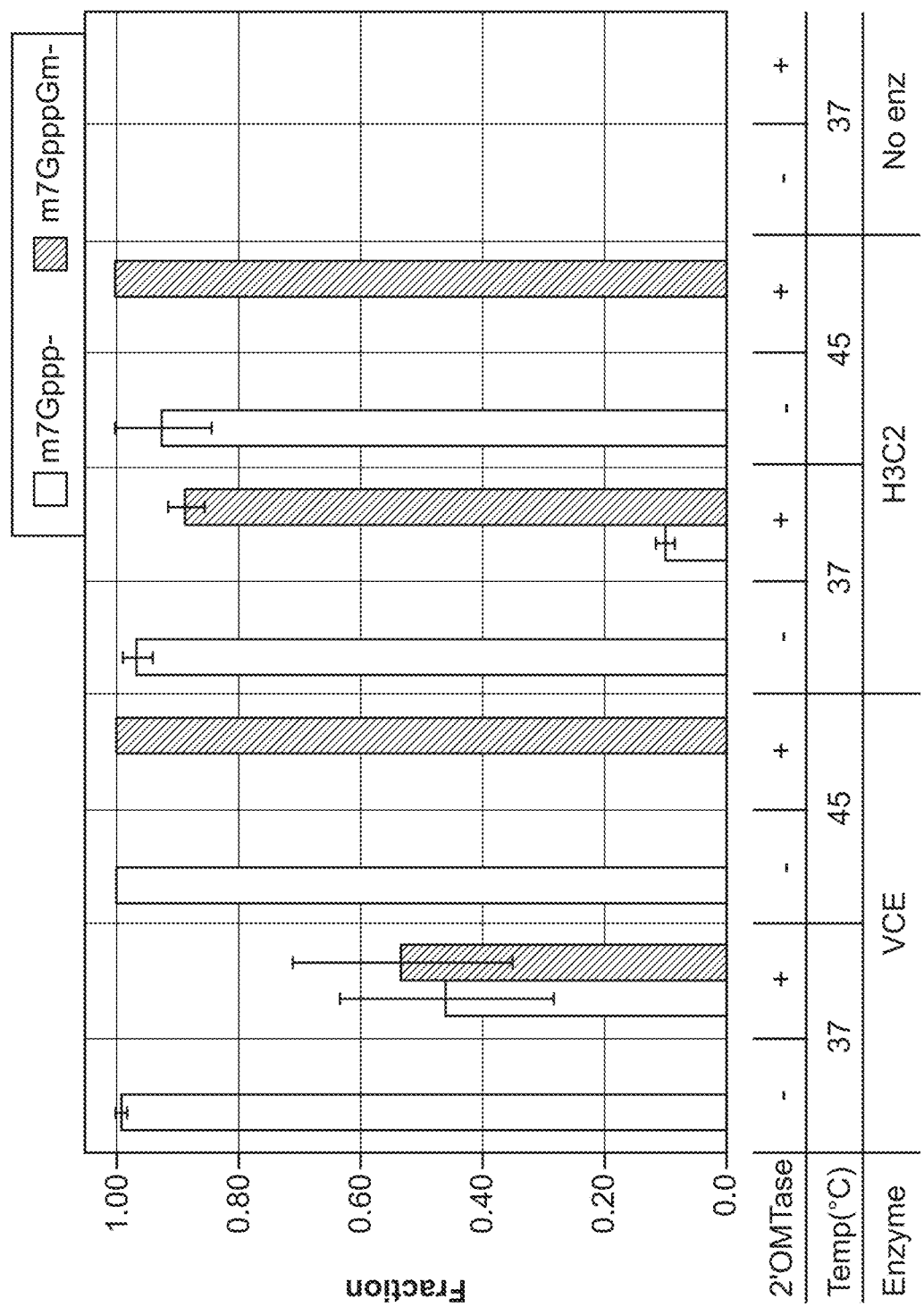
FIG. 11 shows that "one-pot" generation of Cap-1 structure is more efficient at 45° C. than at 37° C. In this experiment, 5 μM of a chemically synthesized 5' triphosphate ribonucleotide oligo (ppp25mer) was incubated with 200 U of Vaccinia virus cap 2'OMTase in the presence of 50 nM H3C2 or VCE, 1 mM GTP and 0.2 mM SAM in 40 μL of 1×RNA capping buffering agent at 37° C. or 45° C. for 30 minutes. The relative quantity of the reactants and products were derived from direct LC/MS analysis. As shown here, performing the one-pot enzymatic reaction at 45° C. generates more Cap-1 structured RNA than at 37° C.

As shown in FIG. 11, both H3C2 and VCE exhibit more capping activity on cluc RNA and CFTR RNA at 45° C. than at 37° C.

Figure 12:
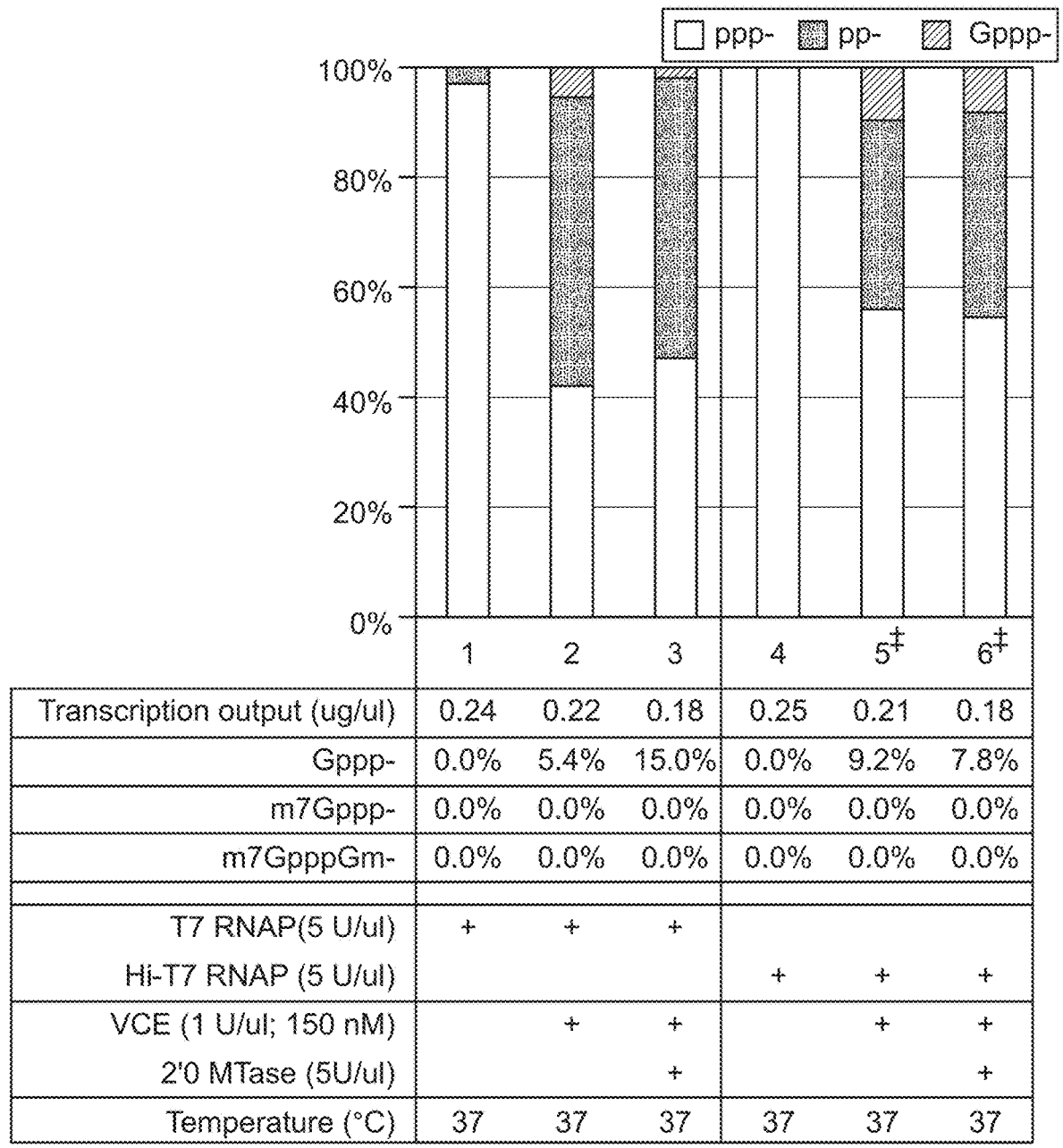
FIG. 12 shows that single-step capped RNA synthesis for a 1.7 kb fluc transcript using commercially available enzymes and recommended reaction temperature does not generate significant amount of Cap-0 or Cap-1 RNA. Reactions were carried out at 37° C. for 1 hour using the indicated components at recommended enzyme concentrations (see Example 7 for details). Transcription output was measured using Qubit RNA BR kit after DNase I treatment. Products of capped RNA synthesis reactions were analyzed by LC/MS. Fraction of transcript containing different 5' groups were estimated using mass intensity of the corresponding masses. Datapoints are average of triplicate experiments unless indicated otherwise.

Example 6: Efficient One-Pot Enzymatic Synthesis of Cap-1 Structure on Triphosphate RNA at Increased Temperature To verify if Vaccinia virus cap 2'OMTase is active at elevated temperatures, a reaction containing 5 µM of a chemically synthesized Cap-0 RNA1 (25 nt) and 200 µM SAM in 20 µL of 1×RNA capping buffering agent (50 mM Tris-HCl, 5 mM KCl, 1 mM $MgCl_2$, 1 mM DTT, pH 8.0) were preheated at 37° C., 45° C. or 50° C. for 1 minute before 100 U of Vaccinia virus cap 2'OMTase (New England Biolabs, Ipswich, MA) was added. The reactions were allowed to proceed at the pre-heat temperature for 30 minutes and then were stopped by heating at 70° C. for 10 minutes. The RNA was purified from the reaction components using the Oligo Clean-up and Concentration Kit (Norgen Biotek, Thorold, Canada). The purified RNA was then digested into nucleosides and cap structures by incubating with 2 µL of nucleotide digestion mix (New England Biolabs, Ipswich, MA) in 20 µL reactions containing nucleoside digestion mix reaction buffering agent (50 mM sodium acetate, pH 5.4, 1 mM $ZnCl_2$) at 37° C. for 1 hour. The nucleoside digestion reactions were then analyzed with Agilent 1290 Infinity II UHPLC (Agilent Technologies, Santa Clara, CA) on a Waters XSelect™ HSS T3 XP column (Waters Corporation, Milford, MA) (2.1×100 mm, 2.5 µm) with a gradient mobile phase consisting of methanol and 10 mM potassium phosphate buffering agent (pH 7.0). As shown in FIG. 12, more Cap-0 RNA was methylated at 45° C. and 50° C. than at 37° C.

Figure 13:
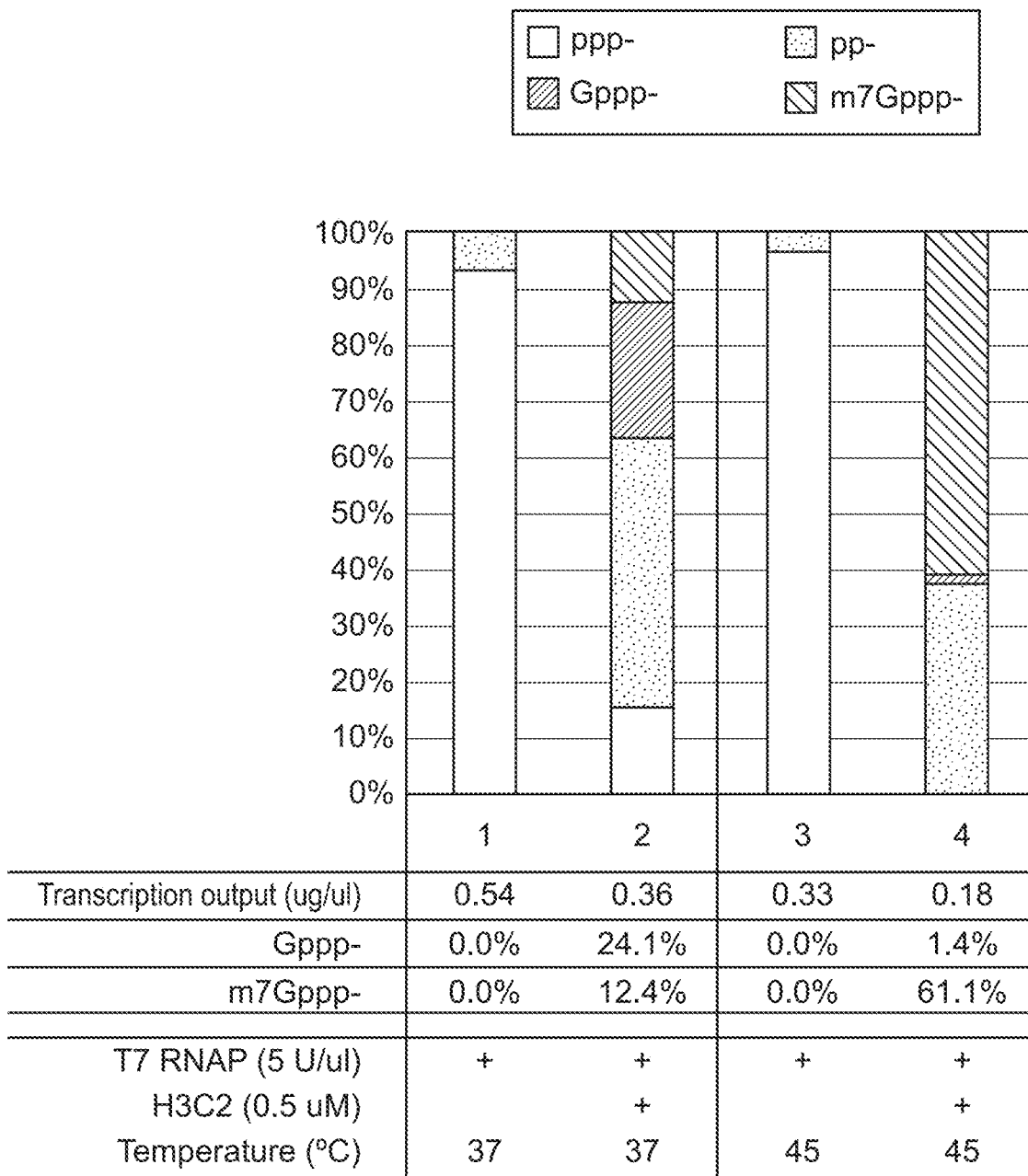
FIG. 13 shows a single-step method to synthesize capped fluc transcript using high concentration of H3C2 capping enzyme and increased temperature. Single-step capped RNA synthesis were carried out at 37 or 45° C. for 1 hour using T7 RNA polymerase with 0.5 μM H3C2 RNA capping enzyme. Fraction of ppp-, pp-, Gppp- and m7Gppp-capped RNA was estimated using capillary electrophoresis. Datapoints are average of duplicate experiments.

To demonstrate one-pot enzymatic synthesis of Cap-1 structure on 5' triphosphate RNA at increased temperature, 5 µM of a chemically synthesized 5' triphosphate RNA1 was incubated with 200 U of Vaccinia virus cap 2'OMTase (final concentration of 5 U/4) in the presence of 50 nM H3C2 or VCE, 1 mM GTP and 0.2 mM SAM in 40 µL reactions containing 1×RNA capping buffering agent (50 mM Tris-HCl, 5 mM KCl, 1 mM $MgCl_2$, 1 mM DTT, pH 8.0) at 37° C. or 45° C. for 30 minutes. The reactions were directly analyzed by LC/MS to determine the mass and the relative quantity of the masses. When paired with 50 nM of VCE, while 5 U/4 of 2'OMTase only generated ~50% of the Cap-01 RNA at 37° C., it generated 100% Cap-1 RNA at 45° C. (FIG. 13). When paired with 50 nM of H3C2, 5 U/4 Vaccinia 2'OMTase generated ~90% Cap-1 RNA at 37° C. and 100% Cap-1 RNA at 45° C. (FIG. 13). Therefore, performing the reactions at 45° C. approximately doubled the yield of Cap-1 RNA in the presence of VCE and increased the yield of Cap-1 RNA in the presence of H3C2.

Example 7: Single-Step Cap-0 and Cap-1 RNA Synthesis Using Individual RNA Polymerase, RNA Capping Enzymes and Cap 2'O Methyltransferase Cap-0Cap-1

A. Single Step Capped RNA Synthesis with Vaccinia Capping Enzyme is Inefficient

As recommended by the manufacturer for the respective reactions, 5 U/µl of T7 RNA polymerase (New England Biolabs; Cat. No. M0251), Hi-T7 RNA polymerase (New England Biolabs; Cat. No. M0658), 1 U/µl of Vaccinia capping enzyme (New England Biolabs; Cat. No. M2080) and 5 U/µl of Vaccinia mRNA cap 2'O methyltransferase (New England Biolabs; Cat. No. M0366) were used as indicated for the transcription and capping of a 1.7 kb fluc transcript (SEQ ID NO:18). The reactions contained 1×T7 RNA polymerase buffering agent (40 mM Tris-HCl, pH 7.9, 10 mM NaCl, 1 mM DTT, 2 mM spermidine) when T7 RNA polymerase was used or 1×Hi-T7 RNA polymerase buffering agent (40 mM Tris-HCl, pH 7.9, 60 mM NaCl, 1 mM DTT, 2 mM spermidine) when Hi-T7 RNA polymerase was used. The reactions were supplemented with 19 mM $MgCl_2$ and 5 mM each of ATP, UTP, GTP, CTP and 0.5 mM SAM. The reactions were carried out at 37° C. for 1 hour, the recommended reaction temperature and duration for T7 RNA polymerase and Vaccinia capping enzyme.

To assess the yield of in vitro transcription, after the 1-hour incubation, for each reaction, 1 µL of the reaction mix was added to a 4-4 solution containing 1×DNase I reaction buffering agent (10 mM Tris-HCl, pH 7.6, 2.5 mM $MgCl_2$, 0.5 mM $CaCl_2$)) and 0.5 U/µl DNase I (New England Biolabs) and incubated at 37° C. for 30 min. The DNase I reactions were then analyzed for total RNA concentration using Qubit RNA Broad Range kit (Thermo Fisher) according to manufacturer's instruction. To verify the transcript sizes and integrity, the DNase I reactions were analyzed using 2% E-Gel (Thermo Fisher) with images taken using a Typhoon RGB scanner (GE Healthcare). Results are shown as transcription output in FIG. 14.

To analyze the extent of RNA capping, single-step capped RNA synthesis reactions were analyzed by RNase H cleavage followed by intact LC/MS analysis. Briefly, the single-step capped RNA synthesis reactions stopped by heating at 80° C. for 30s in the presence of 2.5 µM of targeting oligo (TO-1) composed of 5' deoxynucleotides and 3' ribonucleotides and a TEG-desthiobiotin group (SEQ ID NO:19). The reactions were allowed to cool down to 25° C. at a rate of 0.1° C./s. The reactions were then subjected to RNase H cleavage by incubation with thermostable RNase H (New England Biolabs; Cat. No. M0523) at a final concentration of 0.5 U/µL at 37° C. for 1 h. To facilitate the analysis of the 5' group using capillary electrophoresis, a FAM-labeled nucleotide was added to the 3' end of the RNase H cleavage fragment. Briefly, 5 µL of the RNase H reaction was retrieved and added to 5 µl of a solution containing 2×NEBuffer 2, 0.5 mM dATP, 0.05 mM FAM-12-dCTP (Perkin Elmer) and 0.25 U/µL DNA polymerase I large (Klenow) fragment (New England Biolabs). The reactions were incubated at 37° C. for 1 hour. In some instances, a small fraction of the Klenow reactions were analyzed on urea PAGE to verify the success of capping. Briefly, 2 µL of the Klenow reactions were retrieved and added to 8 µL of 2×RNA loading dye (New England Biolabs). The mixtures were then analyzed by electrophoresis through a urea-15% polyacrylamide gel. Gel images were acquired by a Typhoon RGB scanner (GE Healthcare) using the Cy2 channel.

To analyze the 5' group status of the coupled transcription/capping reaction products using capillary electrophoresis or mass spectrometry, the Klenow reaction products (RNase H-cleavage products still annealed to the desthiobiotinylated targeting oligo) were then purified by size selection using AMPure® XP Beads (Thermo Fisher) and then selected using streptavidin magnetic beads. Briefly, 45 µL of nuclease-free water was added to 5 µL of RNase H cleavage reactions, which was then added to 100 µL of NEBNext® Sample Purification Beads (New England Biolabs) and incubated at room temperature for 5 minutes. The beads were then placed next to a magnet for 2 minutes at room temperature. The clarified supernatant was retrieved and added to pre-cleared NEBNext® Sample Purification Beads derived from 100 µL of beads suspension. After incubating at room temperature for 5 min, the beads were then placed next to a magnet for 2 minutes at room temperature. The clarified supernatant was added to pre-cleared beads derived from 50 µL of Dynabeads® MyOne Streptavidin C1 (Thermo Fisher). After washing 4 times with 50 µL of low salt wash buffering agent (5 mM Tris, pH 7.5, 0.5 mM EDTA, 60 mM NaCl), the bound RNA was eluted by incubating the clarified beads in 10 µL of nuclease-free water. The eluted RNA was then analyzed by capillary electrophoresis on an Applied Biosystems 3130xl Genetic Analyzer (16 capillary array) or an Applied Biosystems 3730xl Genetic Analyzer (96 capillary array) using Gene Scan® 120 LIZ dye Size Standard (Applied Biosystems). Reaction products were analyzed using PeakScanner software (Thermo Fisher Scientific) and an in-house software suite. Areas of peaks corresponding to the m7Gppp-, unmethylated Gppp-, uncapped pp- and ppp-RNaseH-cleaved transcript were quantified and used to calculate fraction of ppp-, pp-, Gppp- and m7Gppp-transcript in the capped RNA synthesis reactions.

To determine the relative quantity of m7GpppGm- (Cap-1), m7G- (Cap-0), unmethyl-G-capped and uncapped RNA using mass spectrometry, intact mass of the relevant species was determined using LC/MS performed by external contractor Novatia LLC (Newtown, PA) or an in-house facility. The extent of RNA capping was assessed by the ratio of the mass intensity of the relevant RNase H-cleaved products.

Figure 14:
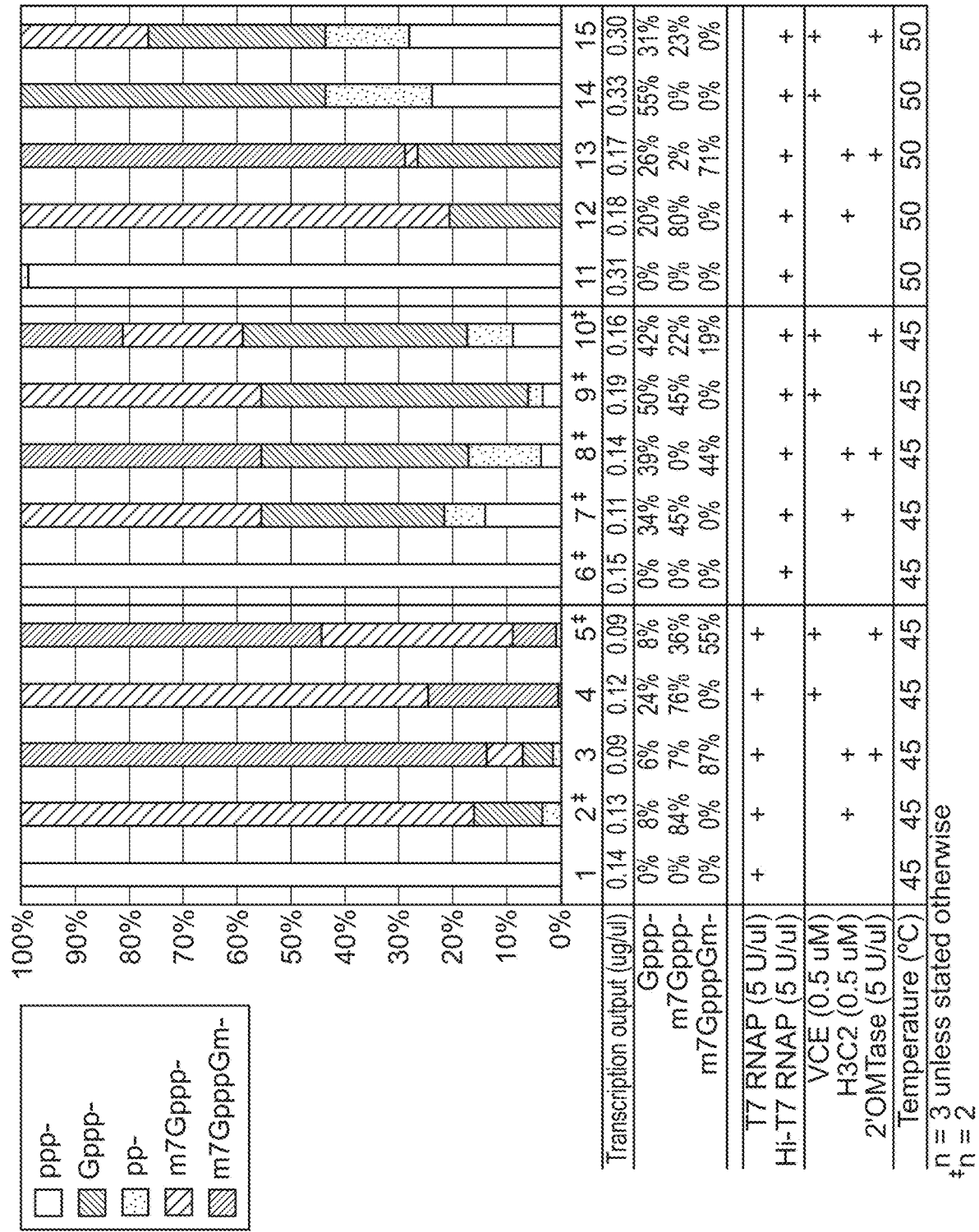
FIG. 14 shows a single-step Cap-0 or Cap-1 RNA synthesis using high capping enzyme concentration at 45 or 50° C. Products of capped RNA synthesis reactions were analyzed by LC/MS. Fraction of transcript containing different 5' group was estimated using mass intensity of the corresponding masses. Datapoints are average of triplicate experiments unless indicated otherwise.

FIG. 14 shows the results of single-step transcription using currently commercially available reaction conditions. Comparing bar 1 and bar 2, the presence of VCE did not significantly affect the transcription output of T7 RNA polymerase but did not generate detectible m7GpppG- (Cap-0) transcript. A small fraction (5.4%) of unmethylated-G capped RNA, an undesired capping reaction intermediate, was detected. Also, about 50% of the transcript contains a 5' diphosphate group, another capping reaction intermediate. As shown in bar 3, when Vaccinia cap 2'O methyltransferase was included in the reaction, transcription output was not significantly affected and no m7GpppGm- (Cap-1) transcript was detected. Approximately 50% of the transcript had a 5' diphosphate group and ~15% had the unmethyl-G capped intermediate. When Hi-T7 RNA polymerase was used instead of T7 RNA polymerase, results similar to T7 RNA polymerase reactions were observed—the presence of VCE did not impact transcription of Hi-T7 RNA polymerase significantly but did not generate detectible level of Cap-0 transcript. Addition of Vaccinia cap 2'O methyltransferase in the reaction did not produce any Cap-1 transcript. From these results, enzyme reagents and reaction conditions that are the current standard for in vitro mRNA synthesis (i.e. RNA synthesis followed by mRNA capping) do not support the in vitro production of capped mRNA in single reactions (i.e., single-step capped RNA synthesis).

B. Faustovirus RNA Capping Enzyme H3C2 Efficiently Caps Transcripts in a Single-Step Reaction In Vitro Since the reagents and conditions of Example 7A were ineffective to produce capped transcripts in a single-step reaction in vitro, new enzymes and reaction conditions were tested for their ability to synthesize single-step capped RNA synthesis in vitro. FIG. 13 shows the results of single-step capped RNA synthesis using high concentration of H3C2 capping enzyme at 37° C. or 45° C.

At 37° C., 0.5 µM of H3C2 capping enzyme generated 12% m7Gppp-capped transcript with as much as 24.1% unmethylated-G capped transcript as measured by capillary electrophoresis. At 45° C., on the other hand, as much as 61% of the transcripts had the m7Gppp-cap and only 1.4% of the transcripts had the unmethylated-G cap. At both temperatures, the transcription output was 50-60% of those without H3C2 capping enzyme. Hence, increasing H3C2 concentration and reaction temperature improved the yield of Cap-0 transcription production in single-step capped RNA synthesis using T7 RNA polymerase and H3C2 RNA capping enzyme.

The impact of further expanding the range of enzyme reagents and reaction temperature was tested by performing the single-step capped RNA synthesis at 45° C. and 50° C. Cap-0 using different combinations of T7 RNA polymerase, Hi-T7 RNA polymerase, VCE, H3C2 and Vaccinia cap 2'O methyltransferase. Specifically, single-step capped RNA synthesis reactions were carried out as described in Examples 7A using 0.5 µM VCE or H3C2 capping enzyme in the presence of absence of 5 U/µL Vaccinia mRNA cap 2'O methyltransferase in conjunction with 5U/4 T7 RNA polymerase or Hi-T7 RNA polymerase in their respective reaction buffering agents as indicated. Reactions were carried out at 45 or 50° C. for 1 hour.

FIG. 14 summarizes the results of this expanded survey. In bars 1-5, capped RNA synthesis reactions were carried out at 45° C. using T7 RNA polymerase. In the presence of H3C2 capping enzyme, 84% of the transcript was m7Gppp-capped (Cap-0) and 8% was unmethylated-G capped (bar 2). In the presence of both H3C2 and cap 2'O methyltransferase, 87% of the transcript had the m7GpppGm-cap (Cap-1), 6% had the unmethylated-G capped and no Cap-0 was detected (bar 3). When VCE was used, 76% of the transcript had the Cap-0 structure with 24% had the unmethylated-G cap structure (bar 4). In the presence of both VCE and cap 2'O methyltransferase, 55% of the transcript had the Cap-1 structure, 36% had the Cap-0 structure and 8% had the unmethylated-G cap structure. RNA yield was not significantly affected when H3C2 or VCE was present in reaction at 45° C. However, RNA yield decreased from 0.14 µg/µL to 0.09 µg/µL when cap 2'O methyltransferase and either of the capping enzymes were present. In capped RNA synthesis reactions using Hi-T7 RNA polymerase at 45° C. (bars 6-10), a smaller fraction of transcript was capped compared to those using T7 RNA polymerase (bars 1-5). H3C2 capping enzyme and VCE generated 45% (bar 7) and 50% Cap-0 transcript (bar 9), respectively. H3C2 in conjunction with cap 2'O methyltransferase generated 44% Cap-1 transcript, 39% unmethylated-G capped transcript and no detectable Cap-0 transcript (bar 8). VCE in conjunction with cap 2'O methyltransferase generated 19% Cap-1 transcript, 22% Cap-0 transcript and 42% unmethylated-G capped transcript (bar 10). Interestingly, the transcription output of the reactions carried out at 45° C. using Hi-T7 RNA polymerase was not significantly affected in the presence of capping enzyme or cap 2'O methyltransferase (bars 6-10). When the capped RNA synthesis reactions were carried out at 50° C. using Hi-T7 RNA polymerase, H3C2 capping enzyme generated 80% Cap-0 transcript and 20% unmethylated-G capped transcript (bar 12). In the presence of both H3C2 and cap 2'O methyltransferase, 71% of the transcript contained Cap-1 structure, 2% contained Cap-0 structure and 26% contained the unmethylated-G cap structure (bar 13). When VCE was used, 55% of the transcript had the unmethylated-G capped structure and no Cap-0 transcript was detected. When both VCE and cap 2'O methyltransferase were present, 23% of the transcript had the Cap-0 structure and 31% had the unmethylated-G cap structure.

To summarize, this example provides single-step reaction conditions that produce in vitro Cap-0 RNA at up to 80% efficiency using H3C2 RNA capping enzyme in conjunction with T7 RNA polymerase or Hi-T7 RNA polymerase (Table 7). The example also describes single-step reaction conditions that can generate Cap-1 RNA at 70-80% efficiency using H3C2 RNA capping enzyme, Vaccinia mRNA cap 2'O methyltransferase in conjunction with T7 RNA polymerase or Hi-T7 RNA polymerase (Table 8).

TABLE 7

| Cap 0 yield | RNAP | CE | Temp (° C.) |
|---|---|---|---|
| ≥80% | T7 | H3C2 | 45° C. |
|  | Hi-T7 | H3C2 | 50% |

TABLE 8

| Cap 1 yield | RNAP | CE | 2'O MTase | Temp(° C.) |
|---|---|---|---|---|
| 40-50% | Hi-T7 | H3C2 or VCE | Vaccinia 2'O MTase | 45° C. |
| ≥70% | T7 | H3C2 | Vaccinia 2'O MTase | 45° C. |
|  | Hi-T7 | H3C2 | Vaccinia 2'O MTase | 50° C. |

Example 8: Single-Step Cap-0 RNA Synthesis Using a H3C2:T7 RNA Polymerase Fusion Protein A fusion construct was prepared to produce protein composed of H3C2 RNA capping enzyme and T7 RNA polymerase linked by a putatively flexible linker sequence (SEQ ID NO:20). The fusion protein was encoded by DNA sequence (SEQ ID NO:21) under the control of T7 promoter or tac promoter, expressed in E. coli and purified using standard chromatographic techniques.

Single-step capped RNA synthesis reactions for the 1.7 kb fluc transcript were performed as indicated in Example 7 in 1×T7 RNA polymerase buffering agent supplemented with 19 mM $MgCl_2$ and 5 mM each of ATP, UTP, GTP, CTP and 0.1 mM SAM in the presence of 0.5 μM H3C2:T7 RNA polymerase fusion. Reactions containing 5 U/4 T7 RNA polymerase with or without 0.5 μM H3C2 capping enzyme were done for comparison. The reactions were carried out at 37 or 45° C. for 1 hour. The RNA yield and fraction of capped and uncapped transcription were measured and analyzed as indicated in Example 7.

Figure 15:
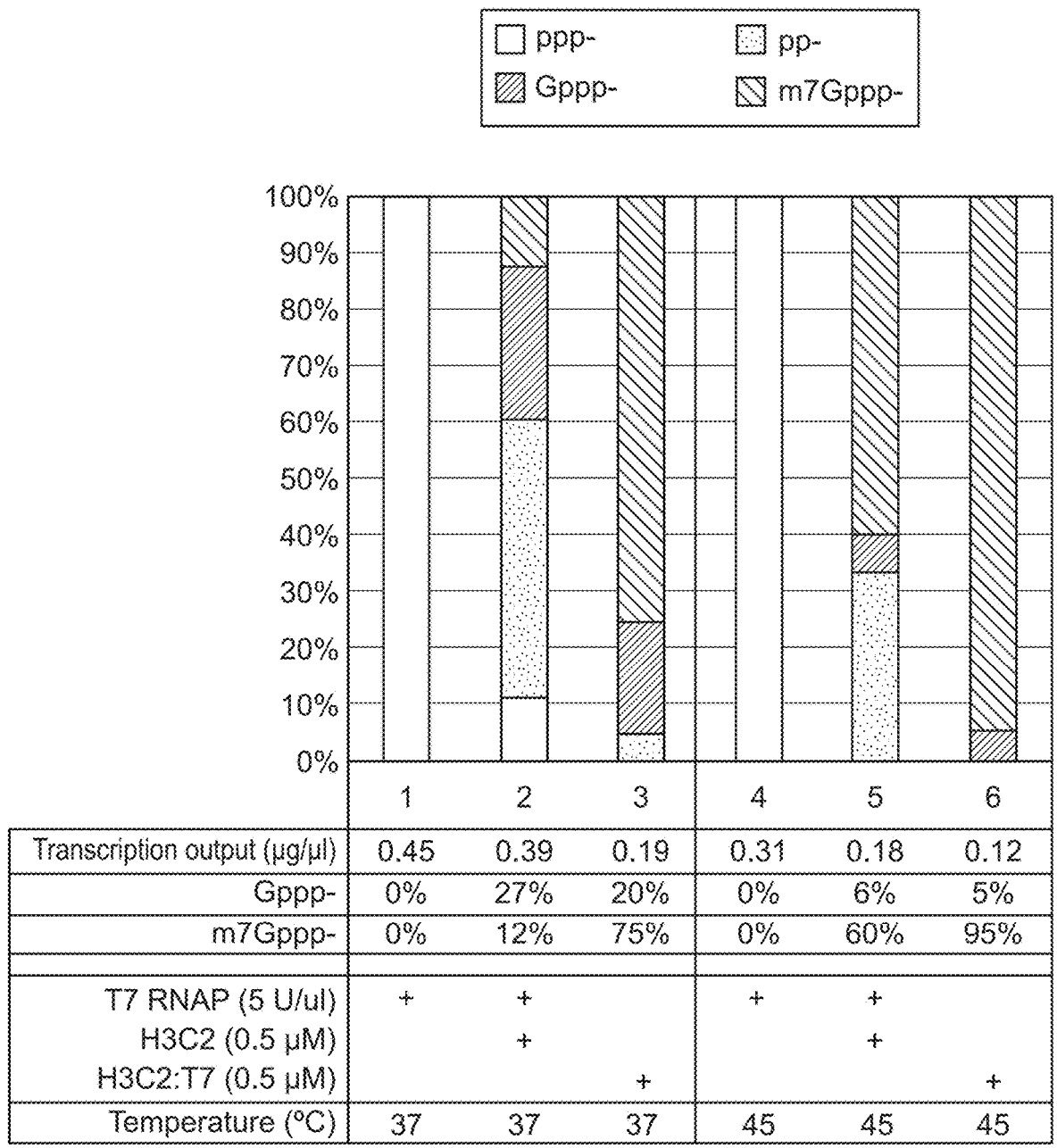
FIG. 15 shows a single-step Cap-0 RNA synthesis using H3C2:T7 fusion protein at 37° C. or 45° C. The fusion protein generated 98% Cap-0 transcript at 45° C. in 1 hour. Products of capped RNA synthesis reactions were analyzed by LC/MS. Fraction of transcript containing different 5' group was estimated using mass intensity of the corresponding masses. Datapoints are average of duplicate experiments unless indicated otherwise.

Results are shown in FIG. 15. When the reactions were performed at 37° C., the H3C2:T7 fusion protein generated 75% m7Gppp-capped (Cap-0) transcript and 20% unmethylated-G capped transcript (bar 1). Under the same conditions, separate enzymes H3C2 and T7 RNA polymerase only generated 12% Cap-0 transcript and 27% unmethylated-G capped transcript (bar 2). The transcription output decreased from 0.45 μg/μL when only T7 RNA polymerase was present (bar 3) to 0.39 μg/μL when H3C2 was added and further to 0.19 μg/μL when H3C2:T7 fusion was used for transcription. At 45° C., the H3C2:T7 RNA polymerase fusion generated 95% Cap-0 transcript and 5% unmethylated-G capped transcript (bar 4), compared to 60% Cap-0 and 6% unmethyl-G capped transcript when individual enzymes were used (bar 5). Similar to reactions performed at 37° C., the transcription output decreased from 0.31 μg/μL when only T7 RNA polymerase was present (bar 6) to 0.18 μg/μL when H3C2 was added or to 0.12 μg/μL when H3C2:T7 fusion was used for transcription.

Thus, under the reaction conditions described, this example demonstrates efficient (e.g., as high as 98%), single-step in vitro Cap-0 RNA synthesis using an H3C2:T7 RNA polymerase fusion protein.

Figure 16:
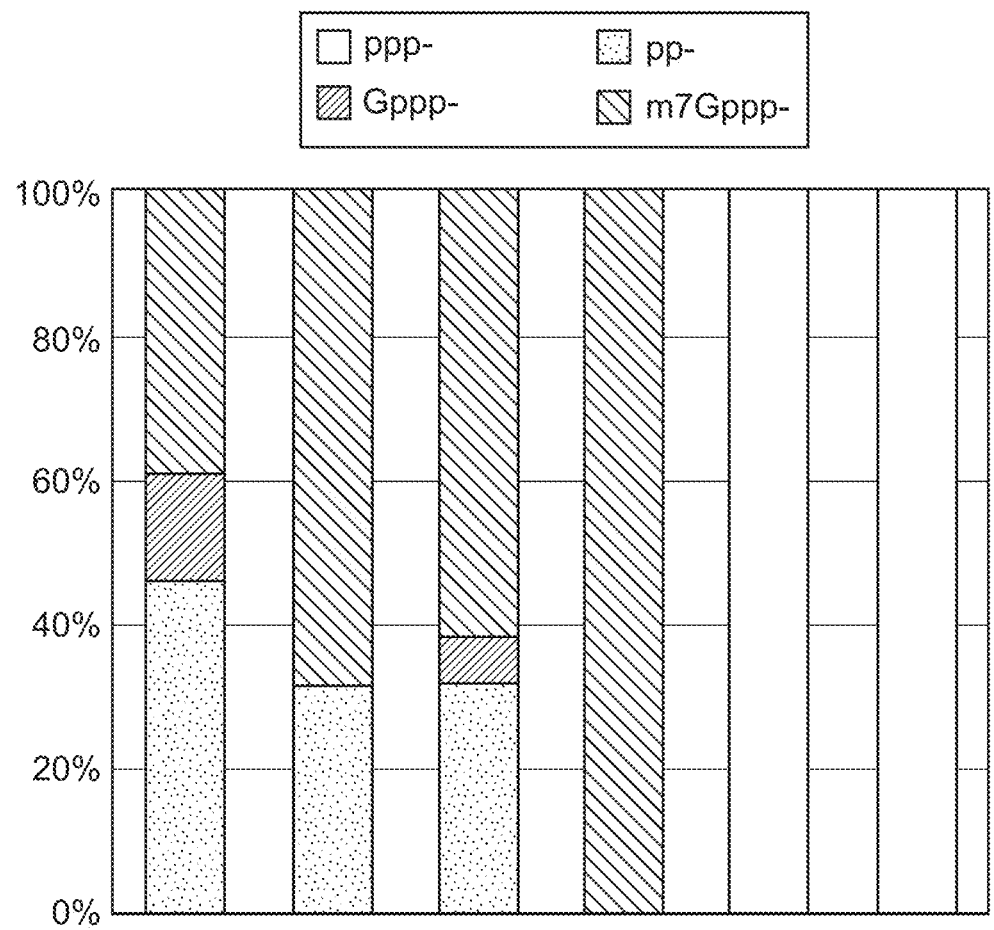
FIG. 16 shows that VCE and H3C2 capping enzyme efficiently cap the 1.8 kb cluc/A120 transcript. 500 nM of unmodified or pseudouridine cluc/A120 transcript was incubated with 100 nM of H3C2 or VCE in the presence of 0.5 mM GTP and 0.1 mM SAM in 10 mL of 1×RNA capping buffering agent (50 mM Tris-HCl, 5 mM KCl, 1 mM MgCl$_2$, 1 mM DTT, pH 8) at 37° C. for 30 min. The capping reactions were analyzed by the RNase H/intact LC/MS workflow as described in EXAMPLE 9. VCE and H3C2 generated 68.4% or 100% m7Gppp-capped cluc/A120 transcript containing pseudouridine, respectively. Notably, both capping enzymes cap a larger fraction of the pseudouridine-containing cluc/A120 transcript than the uridine counterpart.

Example 9: RNA Capping Enzymes Efficiently Caps In Vitro Transcripts Containing Pseudo-Uridine A ~1800 nt RNA encoding the cypridina luciferase protein with a 120 nt poly(A) tail (cluc/A120) was synthesized with in vitro transcription using T7 RNA polymerase (New England Biolabs Inc.) in the presence of pseudouridine triphosphate (Trilink Biotechnologies) or unmodified uridine triphosphate (New England Biolabs Inc.). 500 nM of unmodified or pseudouridine cluc/A120 transcript was incubated with 100 nM of H3C2 or VCE in the presence of 0.5 mM GTP and 0.1 mM SAM in 10 mL of 1×RNA capping buffering agent (50 mM Tris-HCl, 5 mM KCl, 1 mM $MgCl_2$, 1 mM DTT, pH 8) at 37° C. for 30 min. A targeting oligo (TO) designed to direct RNase H to cleave out a 5' fragment was then added to each capping reaction to achieve a final TO concentration of 2.5 μM. Each reaction was then heated at 80° C. for 30 s to anneal the TO to the transcript and inactivate the capping enzymes and cooled slowly to room temperature. Thermostable RNase H (New England Biolabs) was added to each reaction at a final concentration of 0.5 U/mL and incubated at 37° C. for 1h. Reaction products were then purified and analyzed by intact LC/MS as described in Example 7. As shown in FIG. 16, VCE and H3C2 m7Gppp-capped 68.4% or 100% of the cluc/A120 transcript containing pseudouridine, respectively. Notably, both capping enzymes cap a larger fraction of the pseudouridine-containing cluc/A120 transcript than the uridine counterpart.

Example 10: Scaled-Up Cap-1 Capping and Functional Assay

Figure 17:
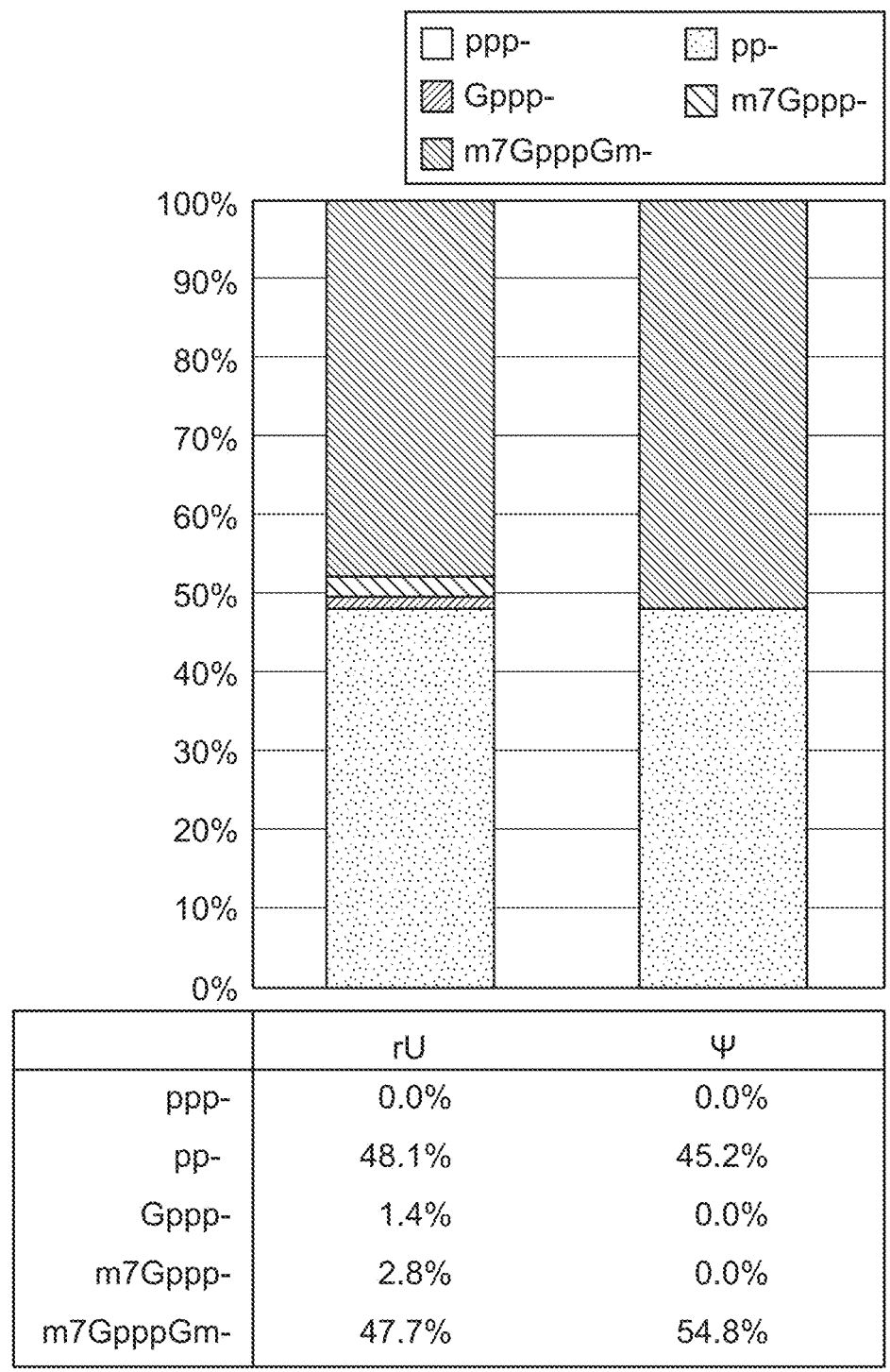
FIG. 17 shows the Cap-1 formation efficiency of a larger RNA quantity. A total of 250 pmol (145 μg) of ~1800 nt cluc/A120 in vitro transcript was capped in a 500 μL reaction containing 1×RNA capping buffering agent (50 mM Tris-HCl, pH 8.0, 5 mM KCl, 1 mM MgCl$_2$, 1 mM DTT), 0.5 mM GTP, 0.1 mM SAM, 10 U/μL of Vaccinia cap 2'O methyltransferase and 500 nM of H3C2 at 45° C. for 1 h. The efficiency of Cap-1 formation was assessed by the RNase H/intact LC/MS as described in Example 10. Under these reaction conditions, 54.8% of the pseudouridine containing cluc/A120 transcript was Cap-1 whereas 47.7% of the uridine counterpart was Cap-1. Optimization of reaction conditions (as described in EXAMPLE 10) may improve the yield of Cap-1 formation. Results are average of duplicate experiments.
Figure 18:
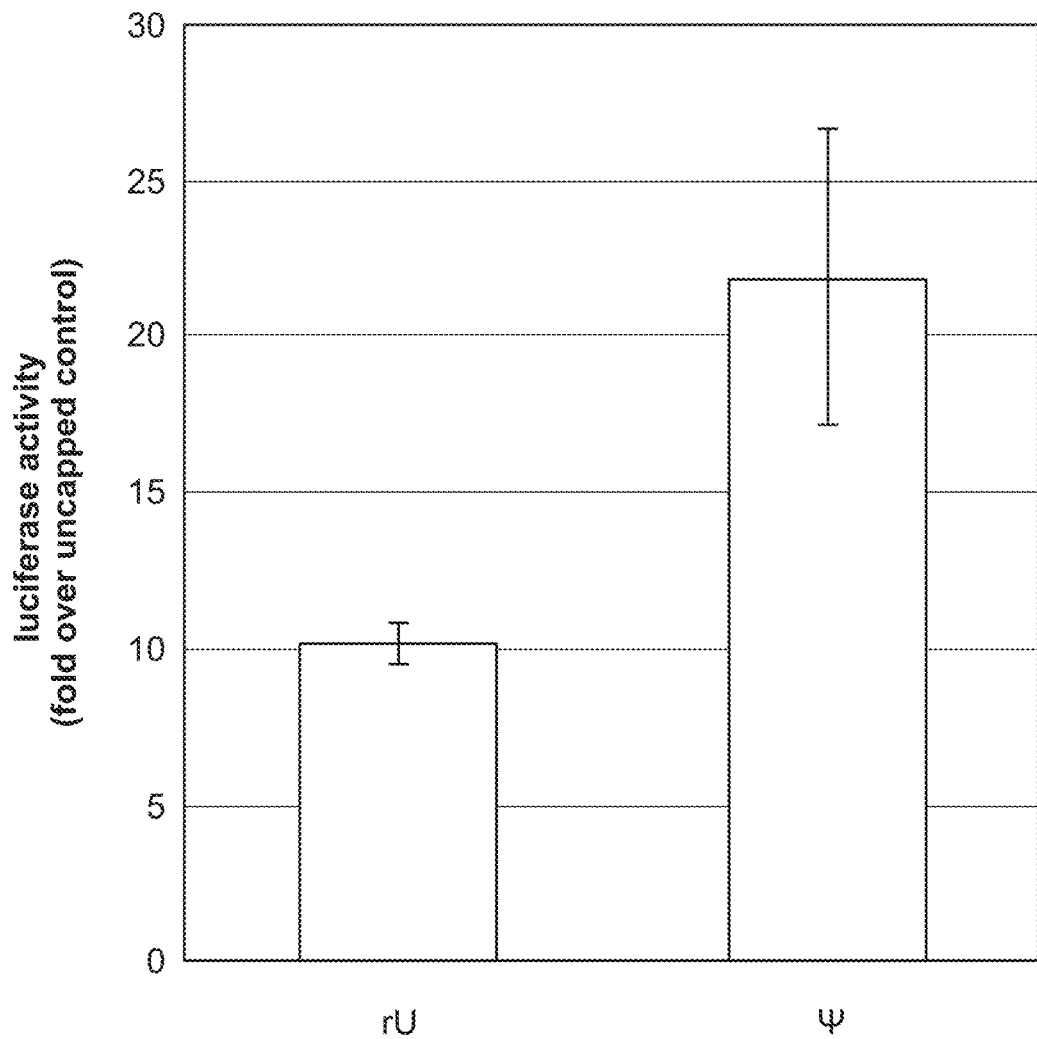
FIG. 18 shows that the Cap-1 cluc/A120 transcript are functionally active in vivo. The Cap-1 cluc/A120 transcript containing uridine or pseudouridine and transfected to HEK293 cells. The translation efficiency of the capped cluc/A120 transcript was measured as relative luciferase activity from HEK293 cells transfected with the capped cluc/A120 transcript in relation to uncapped cluc/A120 transcript four hours after transfection. The luciferase assay shows that the capped transcripts containing rU and pseudouridine exhibited luciferase activity 10 or 20-fold, respectively, over uncapped controls, indicating that the RNAs capped with H3C2 and Vaccinia 2'O methyltransferase at 45° C. were functionally active.

A total of 250 pmol (145 μg) of ~1800 nt cluc/A120 in vitro transcript was capped in a 500 μL reaction containing 1×RNA capping buffering agent (50 mM Tris-HCl, pH 8.0, 5 mM KCl, 1 mM $MgCl_2$, 1 mM DTT), 0.5 mM GTP, 0.1 mM SAM, 10 U/μL of Vaccinia cap 2'O methyltransferase (NEB M0366) and 500 nM of H3C2 at 45° C. for 1 h. The efficiency of Cap-1 formation was assessed by the RNase H/intact LC/MS as described in Example 7. The RNA was purified using acidic phenol and chloroform, followed by ethanol precipitation, and rehydrated in nuclease-free water. The RNA concentration was estimated by Qubit RNA (Broad Range) kit (ThermoFisher). The translation efficiency of the capped cluc/A120 transcript was measured as relative luciferase activity from HEK293 cells transfected with the capped cluc/A120 transcript in relation to uncapped cluc/A120 transcript. HEK293 cells were transfected with 250 ng of Purified cluc/A120 transcript\using Lipofectamine MessengerMax transfection reagent (ThermoFisher). Luciferase activity was assayed four hours post-transfection on 10 μL of culture medium supernatant using the BioLux® Cypridina Luciferase Assay Kit (New England Biolabs Inc. Ipswich). Luminescence was measured using Centro LB960 microplate luminometer from Berthold technologies. As shown in FIG. 17, the scale-up capping reaction achieved 47.7% and 54.8% Cap-1 formation on cluc/A120 containing rU and pseudouridine, respectively, consistent to the results in Example 5 and FIG. 11. The luciferase assay results in triplicate showed that the translation efficiency from the purified capped transcripts containing rU and pseudouridine exhibited high luciferase activity (FIG. 18), indicating that the RNAs capped with H3C2 at 45° C. were functionally active. It should be noted that modifications to reaction conditions such as reaction volume, concentration of enzymes and reaction components, reaction time and reaction temperature may improve the Cap-1 formation efficiency of a larger quantity of RNA and the translation efficiency of the resultant Cap-1 RNA.

Figure 19:
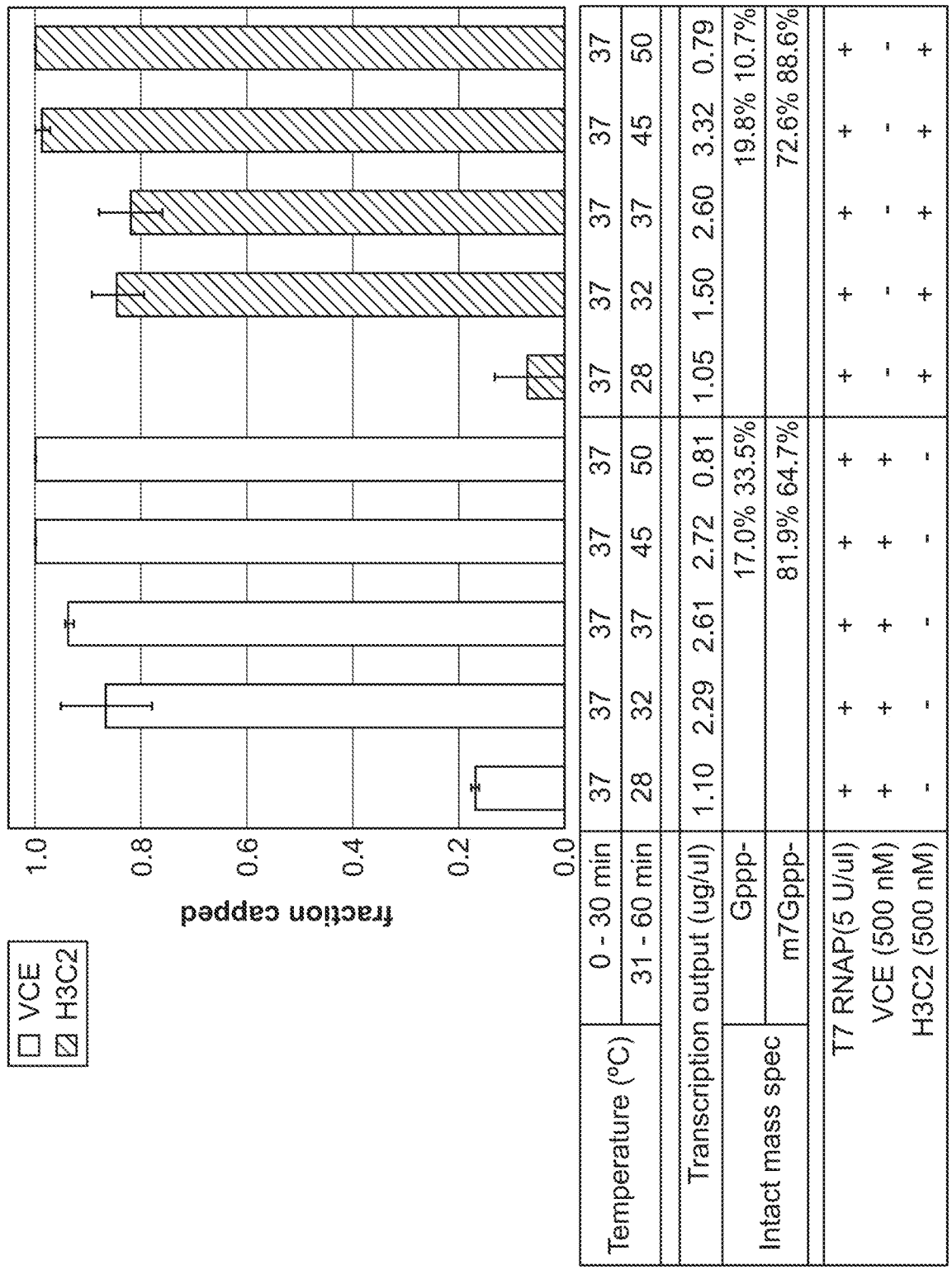
FIG. 19 shows that multiple temperature steps can improve the transcription output and capping efficiency of single-vessel capped RNA synthesis. Single-vessel capped RNA synthesis reactions using T7 RNA polymerase paired with VCE or H3C2 capping enzyme were performed for a 1.7 kb fluc transcript as described in Example 11, where reactions were incubated at 37° C. for 30 min, followed by a second 30-minute incubation at temperatures between 28° C. and 50° C. The transcription output was evaluated using DNase I/Qubit method. Fraction capped was estimated by the RNase H/Klenow fill-in and urea PAGE method. Samples that showed the highest fraction capped were subjected to intact LC/MS analysis. For VCE, the m7Gppp-transcript forming efficiency peaked at second reaction temperature of 45° C., whereas for H3C2, the m7Gppp-forming efficiency peaked at second reaction temperature of 50° C. T7 RNAP transcription output, on the other hand, peaked at 45° C. when paired with either VCE or H3C2, reflecting the low transcription activity at the lower and upper ends of the tested temperatures (28° C. and 50° C., respectively). Hence, tandem temperature steps of 37° C. for 30 min followed by 45° C. for 30 min yielded the optimal balance of transcription output and capping efficiency in this example. Modifications to reaction conditions such as the reaction time, reaction temperature and the number of temperature steps may further improve the transcription yield and fraction of m7G-capped transcript.

Example 11: Single-Vessel Capped RNA Synthesis with Multiple Temperature Steps Single-vessel capped RNA synthesis reactions for the 1.7 kb fluc transcript were performed as indicated in Example 7, namely, 5 U/ul of T7 RNA polymerase (New England Biolabs; Cat. No. M0251) was incubated with or without 500 nM of Vaccinia capping enzyme (New England Biolabs; Cat. No. M2080) or H3C2 capping enzyme for 37° C. for 30 min, followed by another 30-min incubation at 28° C., 32° C., 37° C., 45° C., or 50° C. The reactions contained 1×T7 RNA polymerase buffering agent (40 mM Tris-HCl, pH 7.9, 10 mM NaCl, 1 mM DTT, 2 mM spermidine) and were supplemented with 19 mM $MgCl_2$ and 5 mM each of ATP, UTP, GTP, CTP and 0.5 mM SAM. The transcription output was analyzed by DNase I/Qubit quantitation as described in Example 7. The capping efficiency of the reactions were evaluated by RNase H cleavage followed by Klenow fill-in with FAM-dCTP and urea-PAGE as indicated in Example 7. Selected reactions were further analyzed by intact mass spectrometer. As shown in FIG. 19, for VCE, the m7Gppp-forming efficiency peaked at second reaction temperature of 45° C., whereas for H3C2, the m7Gppp-forming efficiency peaked at second reaction temperature of 50° C. T7 RNAP transcription output, on the other hand, peaked at 45° C. when paired with either VCE or H3C2, reflecting the low transcription activity at the lower and upper end of the tested temperatures (28° C. and 50° C., respectively). Hence, tandem temperature steps of 37° C. for 30 min followed by 45° C. for 30 min yielded the optimal balance of transcription output and capping efficiency in this example. Modifications to reaction conditions such as the reaction time, reaction temperature and the number of temperature steps may further improve the transcription yield and fraction of m7G-capped transcript.

---

What is claimed is:

1. A composition comprising:
   (i) a polynucleotide;
   a single-chain RNA capping enzyme that has RNA triphosphatase (TPase), guanylyltransferase (GTase) and guanine-N7 methyltransferase (N7 MTase) activities and comprises an amino acid sequence at least 90% identical to (a) SEQ ID NO:7, (b) SEQ ID NO:8, (c) SEQ ID NO:9, and/or (d) SEQ ID NO:10;
   (iii) guanosine triphosphate (GTP);
   (iv) a buffering agent; and
   (v) a methyl group donor.

2. The composition of claim 1, wherein the composition has a temperature in the range of 23° C.-60° C.

3. The composition of claim 1, wherein the composition is RNase-free and optionally comprises (vi) one or more RNase inhibitors.

4. The method of claim 1, wherein the single-chain RNA capping enzyme comprises an amino acid sequence at least 90% identical to (a) SEQ ID NO:2, (b) SEQ ID NO:3, and/or (c) SEQ ID NO:4.

5. The composition of claim 1, wherein the polynucleotide comprises a DNA template and the composition further comprises a bacteriophage polymerase and ribonucleotide triphosphates for transcribing the DNA template to form an uncapped target RNA.

6. The composition of claim 1, wherein the composition optionally comprises (vii) S-adenosyl methionine (SAM) and (viii) a cap 2'O methyltransferase enzyme.

7. The composition of claim 1, wherein the polynucleotide comprises an uncapped target, the uncapped target RNA comprising one or more pseudouridines and/or one or more m1pseudouridines.

8. The composition of claim 1 further comprising one or more detergents, dyes, solvents and/or preservatives.

9. The composition of claim 1, wherein the single-chain RNA capping enzyme comprises an amino acid sequence at least 95% identical to (a) SEQ ID NO:7, (b) SEQ ID NO:8, (c) SEQ ID NO:9, and/or (d) SEQ ID NO: 10.

10. A kit comprising:
    a single-chain RNA capping enzyme that has RNA triphosphatase (TPase), guanylyltransferase (GTase) and guanine-N7 methyltransferase (N7 MTase) activities and comprises an amino acid sequence at least 90% identical to (a) SEQ ID NO:7, (b) SEQ ID NO:8, (c) SEQ ID NO:9, and/or (d) SEQ ID NO:10, wherein the enzyme is in a storage buffering agent; and a reaction buffering agent.

11. The kit of claim 10, wherein the kit further comprises a bacteriophage polymerase and ribonucleotides, for transcribing a template polynucleotide encoding a target RNA.

12. The kit of claim 10, wherein the kit further comprises S-adenosyl methionine (SAM), cap 2'O methyltransferase enzyme (2'OMTase), or both SAM and 2'OMTase.

13. The kit of claim 10, wherein the single-chain RNA capping enzyme comprises an amino acid sequence at least 90% identical to (a) SEQ ID NO:2, (b) SEQ ID NO:3, and/or (c) SEQ ID NO:4.

14. The kit of claim 10, wherein the kit further comprises one or more detergents, dyes, solvents and/or preservatives.

15. The kit of claim 10, wherein the single-chain RNA capping enzyme comprises an amino acid sequence that is at least 95% identical to (a) SEQ ID NO:7, (b) SEQ ID NO:8, (c) SEQ ID NO:9, and/or (d) SEQ ID NO:10.

16. A method for efficiently capping RNA in vitro, comprising:
    contacting:
    (i) an RNA sample comprising an uncapped target RNA;
    a single-chain RNA capping enzyme that has RNA triphosphatase (TPase), guanylyltransferase (GTase) and guanine-N7 methyltransferase (N7 MTase) activities and comprises an amino acid sequence at least 90% identical to (a) SEQ ID NO:7, (b) SEQ ID NO:8, (c) SEQ ID NO:9, and/or (d) SEQ ID NO: 10;
    (iii) guanosine triphosphate (GTP) or modified GTP
    (iv) a buffering agent; and
    (v) a methyl group donor,
    at a temperature of 23° C.-60° C., to form a capped target RNA.

17. The method of claim 16, wherein the single-chain RNA capping enzyme comprises an amino acid sequence at least 90% identical to (a) SEQ ID NO:2, (b) SEQ ID NO:3, and/or (c) SEQ ID NO:4.

18. The method according to claim 16, further comprising detecting capped target RNA.

* * * * *